(12) United States Patent
Patel et al.

(10) Patent No.: US 8,993,619 B2
(45) Date of Patent: Mar. 31, 2015

(54) CYCLIC BRIDGEHEAD ETHER DGAT1 INHIBITORS

(71) Applicants: Sejal Patel, Lexington, MA (US); Justin Mao, North Reading, MA (US); Qian Liu, Malden, MA (US); Rui Zheng, Chestnut Hill, MA (US); Tyler Harrison, Somerville, MA (US); Rohit Duvadie, Arlington, MA (US); Xin Chen, Lexington, MA (US); Frederic Zecri, Brookline, MA (US); Jay Larrow, Cambridge, MA (US); Xuchun Zheng, Changshu (CN); Yizong Zhou, Changshu (CN); Jiong Ye, Changshu (CN); Yiping Ding, Changshu (CN); Yu Gai, Changshu (CN)

(72) Inventors: Sejal Patel, Lexington, MA (US); Justin Mao, North Reading, MA (US); Qian Liu, Malden, MA (US); Rui Zheng, Chestnut Hill, MA (US); Tyler Harrison, Somerville, MA (US); Rohit Duvadie, Arlington, MA (US); Xin Chen, Lexington, MA (US); Frederic Zecri, Brookline, MA (US); Jay Larrow, Cambridge, MA (US); Xuchun Zheng, Changshu (CN); Yizong Zhou, Changshu (CN); Jiong Ye, Changshu (CN); Yiping Ding, Changshu (CN); Yu Gai, Changshu (CN)

(73) Assignee: Novartis AG, Basel (CH)

( * ) Notice: Subject to any disclaimer, the term of this patent is extended or adjusted under 35 U.S.C. 154(b) by 43 days.

(21) Appl. No.: 13/871,586

(22) Filed: Apr. 26, 2013

(65) Prior Publication Data

US 2013/0289058 A1   Oct. 31, 2013

Related U.S. Application Data

(60) Provisional application No. 61/639,341, filed on Apr. 27, 2012, provisional application No. 61/787,695, filed on Mar. 15, 2013.

(51) Int. Cl.

| | |
|---|---|
| *A01N 43/08* | (2006.01) |
| *A61K 31/34* | (2006.01) |
| *A01N 43/16* | (2006.01) |
| *A61K 31/35* | (2006.01) |
| *A61K 31/505* | (2006.01) |
| *A01N 43/40* | (2006.01) |
| *A61K 31/44* | (2006.01) |
| *A01N 43/82* | (2006.01) |
| *A61K 31/41* | (2006.01) |
| *A01N 43/76* | (2006.01) |
| *A61K 31/42* | (2006.01) |
| *C07D 401/00* | (2006.01) |
| *C07D 403/00* | (2006.01) |

(Continued)

(52) U.S. Cl.
CPC ............ *C07D 493/08* (2013.01); *A61K 31/422* (2013.01); *A61K 31/4245* (2013.01); *A61K 31/433* (2013.01); *A61K 31/4439* (2013.01); *A61K 31/506* (2013.01); *A61K 45/06* (2013.01); *C07D 413/12* (2013.01); *C07D 417/12* (2013.01)
USPC ........... 514/469; 514/456; 514/275; 514/337; 514/363; 514/364; 514/374; 514/377; 544/331; 546/268.7; 546/269.1; 546/271.4; 548/138; 548/143; 548/234; 548/236

(58) Field of Classification Search
CPC ............ A61K 31/422; A61K 31/4245; A61K 31/433; A61K 31/4439; A61K 31/506; A61K 45/06; C07D 413/12; C07D 417/12; C07D 493/08
USPC ................. 514/275, 337, 363, 364, 374, 377; 544/331; 546/268.7, 269.1, 271.4; 548/138, 143, 234, 236
See application file for complete search history.

(56) References Cited

U.S. PATENT DOCUMENTS

2014/0275173 A1 * 9/2014 Zhang et al. .................. 514/337

FOREIGN PATENT DOCUMENTS

| WO | 2007/126957 | 11/2007 |
|---|---|---|
| WO | 2009/081195 | 7/2009 |
| WO | 2012/047948 | 4/2012 |

OTHER PUBLICATIONS

Birch et al., Journal of medicinal Chemistry, 52:1558-1568 (2009).
(Continued)

*Primary Examiner* — Kendra D Carter
(74) *Attorney, Agent, or Firm* — Joshua Roth

(57) ABSTRACT

The invention relates to compounds of formula (I):

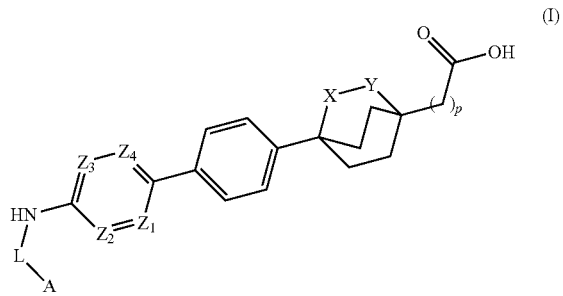

useful for treating disorders mediated by acyl coA-diacylglycerol acyl transferase 1 (DGAT1), e.g. metabolic disorders. The invention also provides methods of treating such disorders, and compounds and compositions etc. for their treatment.

18 Claims, No Drawings

(51) Int. Cl.

| | | | |
|---|---|---|---|
| C07D 405/00 | (2006.01) | A61K 31/433 | (2006.01) |
| C07D 411/00 | (2006.01) | A61K 31/4439 | (2006.01) |
| C07D 413/00 | (2006.01) | A61K 31/506 | (2006.01) |
| C07D 417/00 | (2006.01) | A61K 45/06 | (2006.01) |
| C07D 419/00 | (2006.01) | C07D 413/12 | (2006.01) |
| C07D 285/12 | (2006.01) | C07D 417/12 | (2006.01) |
| C07D 285/14 | (2006.01) | | |
| C07D 513/00 | (2006.01) | | |
| C07D 271/10 | (2006.01) | | |
| C07D 271/12 | (2006.01) | | |
| C07D 498/00 | (2006.01) | | |
| C07D 263/00 | (2006.01) | | |
| C07D 263/34 | (2006.01) | | |
| C07D 493/08 | (2006.01) | | |
| A61K 31/422 | (2006.01) | | |
| A61K 31/4245 | (2006.01) | | |

(56) References Cited

OTHER PUBLICATIONS

Adcock et al., Journal of the American Chemical Society, 100(25):7799-7810 (1978).

* cited by examiner

CYCLIC BRIDGEHEAD ETHER DGAT1 INHIBITORS

RELATED APPLICATIONS

This application claims priority to U.S. Provisional Application No. 61/639,341 filed on Apr. 27, 2012, U.S. Provisional Application No. 61/787,695 filed Mar. 15, 2013, and International Application No. PCT/CN2013/072735 filed Mar. 15, 2013, the contents of which are incorporated herein by reference in their entireties.

TECHNICAL FIELD

This invention relates to compounds useful for treating disorders mediated by acyl coA-diacylglycerol acyl transferase 1 (DGAT1), e.g. metabolic disorders. The invention also provides methods of treating such disorders, and compounds and compositions etc. for their treatment.

BACKGROUND ART

Although triglycerides (also known as "triacylglycerides") are essential for normal physiology, excess triglyceride accumulation results in obesity and, particularly when it occurs in nonadipose tissues, is associated with insulin resistance. Obesity increases the risk of many common and serious conditions, including coronary heart disease, hypertension, dyslipidemia, atherosclerosis, type-II diabetes, stroke, osteoarthritis, restrictive pulmonary disease, sleep apnoea, certain types of cancers and inflammatory disorders. The standard treatment for obesity is calorific restriction and increase of physical exercise. However, such approaches are rarely successful and pharmaceutical treatments are required to correct these metabolic disorders.

A potential therapy for these conditions therefore involves inhibiting triglyceride synthesis.

Diacylglycerol acyl-transference (DGAT) is an enzyme that catalyzes the last step in triacylglycerol biosynthesis. DGAT catalyzes the coupling of a 1,2-diacylglycerol with a fatty acyl-CoA resulting in Coenzyme A and triacylglycerol. Two enzymes that display DGAT activity have been identified: DGAT1 (acyl coA-diacylglycerol acyl transferase 1) [Cases et al., *Proc. Natl. Acad. Sci.* 1998, 95:13018-13023] and DGAT2 (acyl coA-diacylglycerol acyl transferase 2) [Cases et al., *J. Biol. Chem.* 2001, 276:38870-38876].

DGAT1 and DGAT2 do not share significant protein sequence homology. Importantly, however, DGAT1 knockout mice are protected from high fat diet-induced weight gain and insulin resistance [Smith et al., *Nature Genetics* 2000, 25:87-90]. The phenotype of the DGAT1 knockout mice suggests that DGAT1 inhibitors would be useful for the treatment of obesity and obesity-associated complications [Smith et al., *Nature Genetics* 2000, 25:87-90].

There is therefore a need for compounds which inhibit the activity of DGAT1.

DISCLOSURE OF THE INVENTION

The inventors have found compounds of formula (I) that are useful for inhibiting the activity of DGAT1.

Accordingly, in a first embodiment of the invention, there is provided a compound of formula (I) or a salt or solvate thereof:

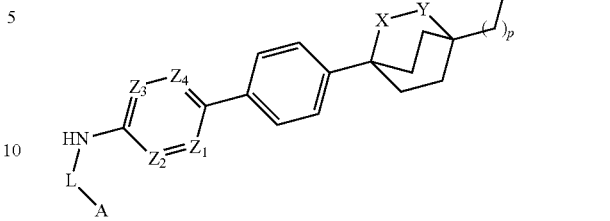

wherein p is 1, 2 or 3; X is O or $CH_2$; Y is O, $CH_2$ or absent, wherein exactly one of X and Y is O; $Z_1$, $Z_2$, $Z_3$ and $Z_4$ are each, independently, N or CH; L is C(O) or absent; and A is a substituted oxazole, thiazole, oxadiazole or thiadiazole substituted with at least one $C_{1-6}$alkyl, $C_{3-7}$cycloalkyl or $C_{1-6}$haloalkyl.

In a second embodiment according to the first embodiment, the invention is a compound of formula (I) wherein p is 1.

In a third embodiment according to the first embodiment, the invention is a compound of formula (I) wherein p is 2.

In a fourth embodiment, the invention is a compound of formula (II) or a salt or solvate thereof:

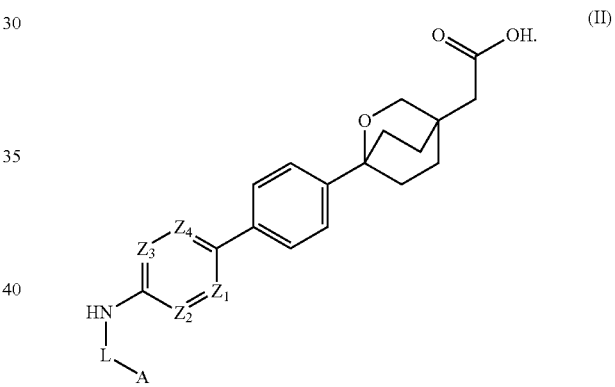

In fifth embodiment, the invention is a compound of formula (III) or a salt or solvate thereof:

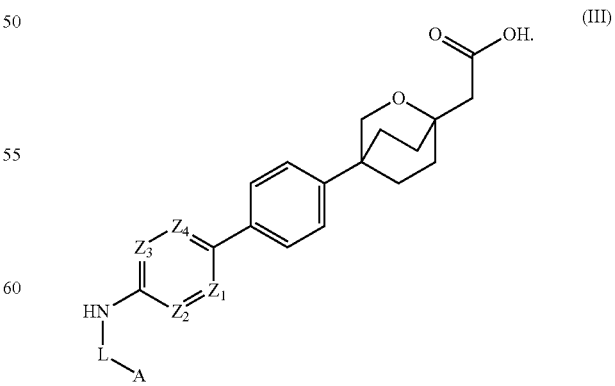

In sixth embodiment, the invention is a compound of formula (IV) or a salt or solvate thereof:

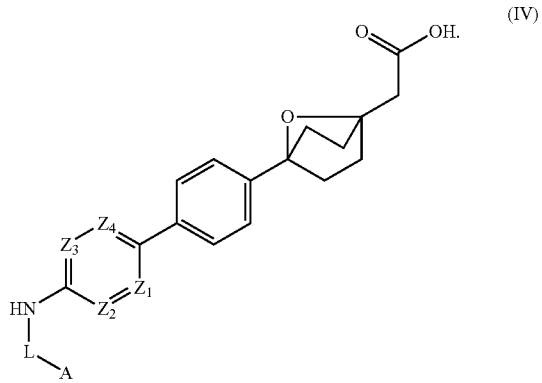

(IV)

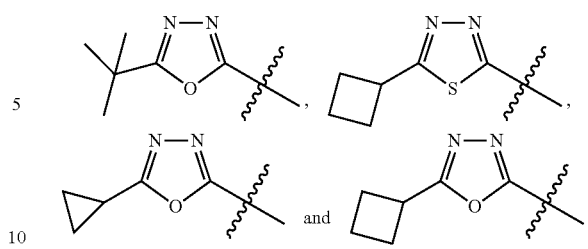

In a seventh embodiment according to any one of the first to sixth embodiments, the invention is a compound according formula (I), (II), (III) and (IV) wherein the variables $Z_1$, $Z_2$, $Z_3$ and $Z_4$ are all CH.

In an eighth embodiment according to any one of the first to sixth embodiments, the invention is a compound according formula (I), (II), (III) and (IV) wherein the variable $Z_1$ is N and the variables $Z_2$, $Z_3$ and $Z_4$ are each CH.

In a ninth embodiment according to any one of the first to sixth embodiments, the invention is a compound according formula (I), (II), (III) and (IV) wherein the variable $Z_2$ is N and the variables $Z_1$, $Z_3$ and $Z_4$ are each CH.

In a tenth embodiment according to any one of the first to sixth embodiments, the invention is a compound according formula (I), (II), (III) and (IV) wherein the variables $Z_1$ and $Z_2$ are both N and the variables $Z_3$ and $Z_4$ are both CH.

In an eleventh embodiment according to any one of the first to tenth embodiments, the invention is a compound according formula (I), (II), (III) and (IV) wherein the variable L is C(O).

In a twelfth embodiment according to any one of the first to tenth embodiments, the invention is a compound according formula (I), (II), (III) and (IV) wherein the variable wherein L is absent.

In a thirteenth embodiment according to any one of the first to twelfth embodiments, the invention is a compound according formula (I), (II), (III) and (IV) wherein the variable A is selected from:

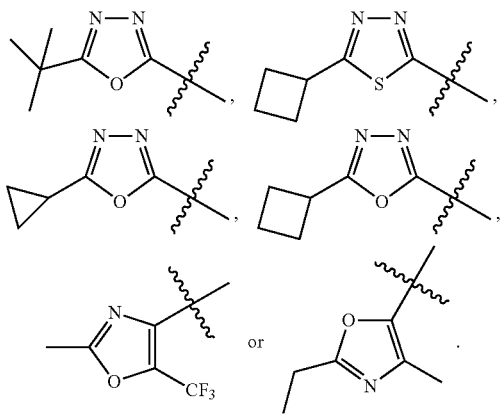

In an fourteenth embodiment according to any one of the first to tenth and twelfth embodiments, the invention is a compound according to formula (I), (II), (III) or (IV) or a salt or solvate thereof, wherein L is absent and A is selected from:

In an fifteenth embodiment according to any one of the first to eleventh embodiments, the invention is a compound of formula (I), (II), (III) or (IV) or a salt or solvate thereof, wherein L is C(O) and A is selected from

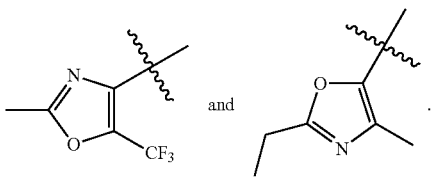

In a sixteenth embodiment according to any one of the first to fifteenth embodiments, the invention is a pharmaceutical composition comprising one or more pharmaceutically acceptable carriers and a therapeutically effective amount of a compound according to formula (I), (II), (III) and (IV).

In a seventeenth embodiment according to any one of the first to fifteenth embodiments, the invention is a combination, in particular a pharmaceutical combination, comprising a therapeutically effective amount of the compound according to formula (I), (II), (III) and (IV) and a second therapeutically active agent.

In an eighteenth embodiment according to any one of the first to fifteenth embodiments, the invention is a method for the treatment of a disease or condition mediated by DGAT1 activity in a subject, wherein the method comprises administering to the subject a therapeutically effective amount of the compound according to formula (I), (II), (III) and (IV).

In a nineteenth embodiment according to any one of the first to fifteenth and eighteenth embodiments, the disease or condition is selected from the group consisting of HCV, impaired glucose tolerance, Type II diabetes or obesity.

In a twentieth embodiment according to any one of the first to fifteenth embodiments, the invention is a method of treating HCV, impaired glucose tolerance, Type II diabetes or obesity comprising administering to a subject in need thereof an effective amount of a composition comprising a compound of to formula (I), (II), (III) and (IV).

In a twentyfirst embodiment according to any one of the first to fifteenth embodiments, the invention is a compound according to formula (I), (II), (III) and (IV), for use as a medicament.

In a twentysecond embodiment according to any one of the first to fifteenth embodiments, the invention is the use of a compound according to formula (I), (II), (III) and (IV), in the manufacture of a medicament for the treatment of a disease or condition mediated by DGAT1 activity.

In a twentythird embodiment according to any one of the first to fifteenth embodiments, the invention is the use of a compound to formula (I), (II), (III) and (IV), for the treatment of HCV, impaired glucose tolerance, Type II diabetes or obesity.

In a twentyfourth embodiment according to any one of the first to fifteenth embodiments, the invention is a method for the prevention, delay of progression or treatment of a disease exacerbated by inadequate phosphatidylcholine production, comprising: administering to a warm-blooded animal in need thereof a therapeutically effective amount of a DGAT1 inhibitor of formula (I), (II), (III) or (IV). In an exemplary embodiment, the warm-blooded animal is a human.

In a twentyfifth embodiment according to any one of the first to fifteenth embodiments, the invention is use of a DGAT1 inhibitor of formula (I), (II), (III) or (IV) for the preparation of a pharmaceutical composition for the treatment of a disorder or disease exacerbated by inadequate phosphatidylcholine production in a subject mediated by the inhibition of DGAT1.

In a twentysixth embodiment according to any one of the first to fifteenth embodiments, the invention is a DGAT1 inhibitor of formula (I), (II), (III), (IV), or a pharmaceutically acceptable salt or ester thereof; for use in the prevention, delay of progression or treatment of a disease or condition which is selected from chylomicronemia 5 syndrome, familial chylomicronemia syndrome, and Type V hyperlipoproteinemia.

In a twentyseventh embodiment according to any one of the first to fifteenth embodiments, the invention is a DGAT1 inhibitor of formula (I), (II), (III) or (IV), or a pharmaceutically acceptable salt or ester thereof, for use in the reduction of postprandial triglyceride levels in patients suffering from a disease or condition which is selected from chylomicronemia syndrome, familial chylomicronemia syndrome, and Type V hyperlipoproteinemia.

In a twentyeighth embodiment according to any one of the first to fifteenth embodiments, the invention is a DGAT1 inhibitor of formula (I), (II), (III) or (IV), or a pharmaceutically acceptable salt or ester thereof, for use in the prevention, delay of progression or treatment of pancreatitis in patients suffering from a disease or condition which is selected from chylomicronemia syndrome, familial chylomicronemia syndrome, and Type V hyperlipoproteinemia.

In a twentyninth embodiment according to any one of the first to fifteenth embodiments, the invention is a DGAT1 inhibitor of formula (I), (II), (III) or (IV), or a pharmaceutically acceptable salt or ester thereof, for use in the prevention, delay of progression or treatment of a symptom selected from recurrent episodes of pancreatitis, deposition of triglycerides in the skin in the form of eruptive xanthomas, hepatosplenomegaly, milky white triglyceride in the blood vessels in the back of the eye (lipemia retinalis), and mild neuro-cognitive deficits.

In a thirtieth embodiment according to the first embodiment, the invention is a compound according formula (I), (II), (III) and (IV) wherein the compound is selected from at least one of:

2-(4-(4'-((5-cyclobutyl-1,3,4-thiadiazol-2-yl)amino)-[1,1'-biphenyl]-4-yl)-2-oxabicyclo[2.2.2]octan-1-yl)acetic acid;

2-(4-(4'-((5-cyclobutyl-1,3,4-oxadiazol-2-yl)amino)-[1,1'-biphenyl]-4-yl)-2-oxabicyclo[2.2.2]octan-1-yl)acetic acid;

2-(4-(4-(5-(2-methyl-5-(trifluoromethyl)oxazole-4-carboxamido)pyridin-2-yl)phenyl)-2-oxabicyclo[2.2.2]octan-1-yl)acetic acid;

2-(4-(4-(5-(2-ethyl-4-methyloxazole-5-carboxamido)pyridin-2-yl)phenyl)-2-oxabicyclo[2.2.2]octan-1-yl)acetic acid;

2-(4-(4'-(2-ethyl-4-methyloxazole-5-carboxamido)-[1,1'-biphenyl]-4-yl)-2-oxabicyclo[2.2.2]octan-1-yl)acetic acid;

2-(4-(4'-((5-(tert-butyl)-1,3,4-oxadiazol-2-yl)amino)-[1,1'-biphenyl]-4-yl)-2-oxabicyclo[2.2.2]octan-1-yl)acetic acid;

2-(1-(4'-((5-cyclobutyl-1,3,4-oxadiazol-2-yl)amino)-[1,1'-biphenyl]-4-yl)-2-oxabicyclo[2.2.2]octan-4-yl)acetic acid;

2-(1-(4'-(2-methyl-5-(trifluoromethyl)oxazole-4-carboxamido)-[1,1'-biphenyl]-4-yl)-2-oxabicyclo[2.2.2]octan-4-yl)acetic acid;

2-(1-(4-(5-((5-cyclobutyl-1,3,4-oxadiazol-2-yl)amino)pyridin-2-yl)phenyl)-2-oxabicyclo[2.2.2]octan-4-yl)acetic acid;

2-(1-(4-(5-(2-methyl-5-(trifluoromethyl)oxazole-4-carboxamido)pyridin-2-yl)phenyl)-2-oxabicyclo[2.2.2]octan-4-yl)acetic acid;

2-(4-(4'-((5-cyclopropyl-1,3,4-oxadiazol-2-yl)amino)-[1,1'-biphenyl]-4-yl)-2-oxabicyclo[2.2.2]octan-1-yl)acetic acid;

3-(4-(4'-((5-(tert-butyl)-1,3,4-oxadiazol-2-yl)amino)-[1,1'-biphenyl]-4-yl)-7-oxabicyclo[2.2.1]heptan-1-yl)propanoic acid;

2-(4-(4'-((5-(tert-butyl)-1,3,4-oxadiazol-2-yl)amino)-[1,1'-biphenyl]-4-yl)-7-oxabicyclo[2.2.1]heptan-1-yl)acetic acid; or a salt or solvate thereof.

Compounds of Formula (I)-(IV) Etc. And Derivatives Thereof

As used herein, the terms "compounds of the invention" and "compound of formula (I)" etc. include pharmaceutically acceptable derivatives thereof and polymorphs, isomers and isotopically labelled variants thereof. Furthermore, the term "compounds of the invention" and "compound of formula (I)" etc include compounds of formula (II), (III) and (IV), and the embodiments thereof disclosed herein.

Pharmaceutically Acceptable Derivatives

The term "pharmaceutically acceptable derivative" includes any pharmaceutically acceptable salt, solvate, hydrate or prodrug of a compound of formula (I). In one embodiment, the pharmaceutically acceptable derivatives are pharmaceutically acceptable salts, solvates or hydrates of a compound of formula (I).

Pharmaceutically Acceptable Salts

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Solvates & Hydrates

The compounds of the invention may exist in both unsolvated and solvated forms. The term "solvate" includes molecular complexes comprising a compound of the invention and one or more pharmaceutically acceptable solvent molecules such as water or $C_{1-6}$ alcohols, e.g. ethanol. The term "hydrate" means a "solvate" where the solvent is water.

Prodrugs

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Description of Isomeric Forms and Separation Methods

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Amorphous & Crystalline Forms

The compounds of the invention may exist in solid states from amorphous through to crystalline forms. All such solid forms are included within the invention.

Isomeric Forms

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate.

"Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Isotopic Labeling

Any formula given herein is also intended to represent unlabeled forms as well as isotopically labelled forms of the compounds. Isotopically labelled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labelled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labelled compound may be particularly desirable for PET or SPECT studies. Isotopically-labelled compounds of formula (I) can generally be prepared by conventional techniques known to those skilled in the art or by processes analogous to those described in the accompanying Examples and Preparations using an appropriate isotopically-labelled reagents in place of the non-labelled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Co-Crystals

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

Treatment of Diseases and Conditions

Compounds of formula (I) have been found to be inhibitors of DGAT1.

The invention provides a compound of formula (I) for use in therapy. The invention further provides a pharmaceutical composition comprising a compound of formula (I) in combination with a pharmaceutically acceptable excipient.

The invention further provides a method for the treatment of a disease or condition mediated by DGAT1, comprising the step of administering a therapeutically effective amount of a compound of formula (I) to a patient. The invention also provides the use of a compound of formula (I) in the manufacture of a medicament for the treatment of a disease or condition mediated by DGAT1. The invention also provides a compound of formula (I) for use in treating a disease or condition mediated by DGAT1.

The invention also provides a crystal of DGAT1 and a compound of formula (I). Such crystals can be used for X-ray diffraction studies of DGAT1 inhibition, e.g. to provide atomic structural information in order to aid rational design of further DGAT1 inhibitors.

The DGAT1 inhibitory activity of the compounds of the invention may be demonstrated by the DGAT1 assay disclosed herein (see "DGAT1 Inhibition Assay"). Preferred compounds of the invention have an $IC_{50}$ in the DGAT1 Inhibition Assay of <100 µM, in one embodiment <10 µM, in another embodiment <1 µM, in another embodiment <100 nM, and in another embodiment <10 nM.

Diseases and Conditions Mediated by DGAT1

The invention is useful for the treatment of a disease or condition mediated by DGAT1. Diseases and conditions mediated by DGAT1 include: metabolic disorders such as obesity, diabetes (e.g. Type II diabetes), anorexia nervosa, bulimia, cachexia, syndrome X, insulin resistance, glucose tolerance, hypoglycemia, hyperglycemia, hyperuricemia, hyperinsulinemia, hypercholesterolemia, hyperlipidemia, dyslipidemia, mixed dyslipidemia, hypertriglyceridemia, pancreatitis, and nonalcoholic fatty liver disease; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, myocardial ischemia, ischemic reperfusion injury, aneurysm, restenosis, and vascular stenosis; neoplastic diseases, such as solid tumors, skin cancer, melanoma, lymphoma, and endothelial cancers, for example, breast cancer, lung cancer, colorectal cancer, stomach cancer, other cancers of the gastrointestinal tract (e.g. esophageal cancer and pancreatic cancer), prostate cancer, kidney cancer, liver cancer, bladder cancer, cervical cancer, uterine cancer, testicular cancer, and ovarian cancer; dermatological conditions, such as acne vulgaris; hepatitis C virus (HCV); pathogens that target lipid droplets (e.g. dengue and chlamydia); and infectious agents which require lipid droplets and/or triglycerides in their lifecycle.

One embodiment, the disease or condition mediated by DGAT 1 is impaired glucose tolerance (IGT), Type II diabetes or obesity.

As used herein a patient is suffering from "obesity" if the patient exhibits at least one of:
- a body mass index (BMI), i.e. the patient's mass (in kg) divided by the square of the patient's height (in m), of 30 or more;
- an absolute waist circumference of >102 cm in men or >88 cm in women;
- a waist-to-hip ratio >0.9 in men or >0.85 in women; or
- a percent body fat >25% in men or >30% in women.

As used herein a patient is suffering from "Type II diabetes" if they meet the World Health Organization criteria for Diabetes diagnosis (Definition and diagnosis of diabetes mellitus and intermediate hyperglycemia, WHO, 2006), i.e. the patient exhibits at least one of:
- a fasting plasma glucose ≥7.0 mmol/l (126 mg/dl); or
- a venous plasma glucose ≥11.1 mmol/l (200 mg/dl) 2 hours after ingestion of 75 g oral glucose load.

As used herein a patient is suffering from "IGT" if they meet the World Health Organization criteria for IGT diagnosis (Definition and diagnosis of diabetes mellitus and intermediate hyperglycemia, WHO, 2006), i.e. the patient exhibits both of:
- a fasting plasma glucose <7.0 mmol/l (126 mg/dl); and
- a venous plasma glucose ≥7.8 and <11.1 mmol/l (200 mg/dl) 2 hours after ingestion of 75 g oral glucose load.

In yet another aspect, the invention is useful as an anorectic.

In one embodiment, the disease or condition mediated by DGAT 1 is HCV (Harris C, Hernandez C, Carpentier A, Kaehlcke K, Rosenberg A R, Farese R V Jr, Ott M Efficient hepatitis C virus particle formation requires diacylglycerol acyltransferase-1. Herker E, Nat. Med. 2010 November; 16(11):1295-8. & Charles Harris, Eva Herker, Robert V. Farese Jr., Melanie Ott, The Journal of Biological Chemistry, 286, 42615-42625.)

In another embodiment, the disease or condition mediated by DGAT1 is myocardial ischemia Stanley, W. C., Expert opinion in Investig. Drugs; 11(5): 615-629, 2002; and Dyck, J. R. and Lopaschuk, G. D., J. Mol. Cell. Cardiol. 34(9): 1099-1109, 2002].

In one embodiment, increasing cellular phosphatidyl choline is achieved by DGAT1 inhibition and used as an approach to the therapeutic increase of phosphatidylcholine in plasma lipoproteins and intestinal epithelium (Kent C, Biochim. Biophys. Acta, 1733: 53-66, 2005; Coleman R A, Prog. Lipid Res., 34: 134-176, 2004; Goni F M, et al. Prog. Lipid Res. 38: 1-48, 1999; Jenkins G M, et al., Cell. Mol. Life. Sci. 62: 2305-2316, 2005; Becker K P, et al. Cell Mol. Life. Sci. 62: 1448-1461, 2005; Kruit J K, et al., World J. Gastroenterol., 12: 6429-6439, 2006; Lewis G F, Curr. Opin. Cardiol., 21: 345-352, 2006; Ehehalt R, Scand. J. of Gastroenterology, 39: 737-742; Stremmel W, Gut, 54: 966-971, 2005; Treede I, J. Biol. Chem., 282: 27155-27164, 2007; Cases et al, Proc. Natl. Acad. Sci. 95:13018-13023, 1998; Cases et al, J. Biol. Chem. 276:38870-38876, 2001; and Smith et al, Nature Genetics 25:87-90, 2000).

In another embodiment, the present invention relates to the use of a DGAT1 inhibitor, or a pharmaceutically acceptable salt or ester thereof, for the treatment of, or the prevention, delay of progression, or treatment of a disease or condition which is selected from chylomicronemia syndrome, familial chylomicronemia syndrome and Type V hyperlipoproteinemia. The present invention further relates to the use of a pharmaceutical composition comprising a DGAT1 inhibitor, or a pharmaceutically acceptable salt or ester thereof, for the prevention, delay of progression, or treatment of a disease or condition which is selected from chylomicronemia syndrome, familial chylomicronemia syndrome and Type V hyperlipoproteinemia.

Hyperlipidemia, or the presence of elevated levels of lipids in the bloodstream, can take the form of hypercholesterolemia (elevated cholesterol), hypertriglyceridemia (elevated triglyceride) or a combination of the two. Hypercholesterolemia, which can further be subdivided, is typically associated with increased risk of atherosclerosis cardiovascular disease. Hypertriglyceridemia occurs when the body's production or intake of triglyceride exceeds the body's ability to metabolize or remove the triglyceride from the bloodstream. The most severe form of hypertriglyceridemia is chylomicronemia (also called hyperchylomicronemia), and is associated with an increased risk of pancreatitis. Chylomicrons are lipoprotein particles that carry absorbed dietary fat from the gut to other body tissues via the bloodstream, and are typically present only during meal times. Chylomicronemia is defined as having the presence of chylomicrons in the bloodstream during times of fasting, and is typically associated with total plasma triglyceride levels above 1000 mg/dL.

The chylomicronemia syndrome refers to a set of clinical complications associated with high chylomicron levels. Typically, patients with the chylomicronemia syndrome have markedly elevated fasting triglyceride levels (1000-2000 mg/dL) with profound excursions (up to 5000 mg/dL and higher) following oral fat intake. The massively elevated plasma triglyceride levels are associated with a number of clinical findings and complications including recurrent episodes of pancreatitis, deposition of triglycerides in the skin in the form of eruptive xanthomas, epatosplenomegaly, a milky pink appearance of the blood vessels in the back of the eye (lipemia retinalis), and mild neuro-cognitive deficits.

The chylomicronemia syndrome can be further subdivided into two groups based on ultracentrifugation of lipoprotein species (see "A system for phenotyping hyperlipoproteinemia", Fredrickson D. S., Lees R. S. Circulation, 1965 March; 31, pp. 321-327).

Fredrickson classification Type I, also known as the familial chylomicronemia syndrome (FCS), patients have accumulation of only chylomicrons in the bloodstream whereas Fredrickson classification Type V, also known as Type V hyperlipoproteinemia, patients have accumulation of both chylomicrons and very low density lipoproteins (VLDL) in the bloodstream.

The familial chylomicronemia syndrome (FCS or Type I hyperlipoproteinemia) is caused by a homozygous or compound heterozygous defect in the clearance of chylomicrons from the bloodstream. The most common cause of FCS is a defect in lipoprotein lipase (LPL), the protein that hydrolyzes triglycerides carried on chylomicrons. Other causes of FCS include defects in apolipoprotein CII (apoCII, a co-activator of LPL) or glycosylphosphatidylinositol-anchored high-density lipoprotein-binding protein 1 (GPIHBP1, an anchoring protein of LPL).

Type I patients are usually identified by early onset as youth of hypertriglyceridemia and pancreatitis. Thus, patients with FCS typically present in childhood with massively elevated triglyceride levels (>2,000 mg/dL), and recurrent bouts of abdominal pain due to pancreatitis. Into adulthood, the triglyceride levels remain elevated, and patients typically experience multiple episodes of abdominal pain and pancreatitis, which can result in hospitalization and death.

Patients also experience other manifestations including eruptive xanthomas, lipemia retinalis, hepatosplenomegaly, and mild neuro-cognitive deficits. The main therapeutic goal in FCS treatment is to prevent or treat pancreatitis via the reduction of triglycerides.

Unfortunately, standard lipid-lowering therapies, such as fibrates, omega-3 fatty acids, statins and nicotinic acid derivatives (niacin), are not effective in lowering triglycerides in patients with FCS. Therefore, the standard of care therapy for FCS patients is a very low fat diet 10% by calories), something which is very difficult to stay compliant with throughout a lifetime [The Familial Chylomicronemia Syndrome. Santamarina-Fojo S. Lipid Disorders 1998. 27(3): 551-567].

Another approach to treat FCS that is under investigation is gene therapy using a replication-deficient Adeno-Associated Viral vector to deliver a naturally-occurring, "beneficial" variant of LPL (Glybera®) intramuscularly. However this treatment is only transiently effective and requires immuno-suppression with mycophenolate, cyclosporine, and steroids [Alipogene tiparvovec, and adeno-associated virus encoding the Ser(447)X variant of human lipoprotein lipase gene for the treatment of patients with lipoprotein lipase deficiency. Burnett J R., Hooper A J. Curr Opin Mol Ther 2009. 6:681-691].

At present there is thus no effective pharmacotherapy for treating FCS and there is thus a need for new methods of treating familial chylomicronemia syndrome (FCS), also known as Type I hyperlipoproteinemia.

Type V hyperlipoproteinemia patients represent a second group at risk for the chylomicronemia syndrome and are usually diagnosed by severe hypertriglyceridemia as adults. This is a heterogeneous group at the extreme end of a spectrum of multifactorial hypertriglyceridemia.

Patients with Type V hyperlipoproteinemia generally have both an underlying genetic cause and one or more acquired causes of hypertriglyceridemia. The underlying genetic causes include well characterized dyslipidemia such as familial combined hyperlipidemia (Type IIA), dysbetalipoproteinemia (Type III) and familial hypertriglyceridemia (Type VI), and a group of less well characterized dyslipidemias (e.g. heterozygous LPL deficiency, defects in apoA & apoC genes, defects in fatty acid binding and transport proteins).

Acquired causes of hypertriglyceridemia include comorbid diseases (e.g. type 2 diabetes, obesity, insulin resistance, lipodystrophy, hypothyroidism), medications (e.g. beta blockers, thiazide diuretics, estrogen, glucocorticoids, transplant medications), and other factors (e.g. pregnancy, alcohol intake).

The primary goal of therapy in Type V patients is to reduce the triglyceride levels, and therefore reduce the risk of pancreatitis. Most patients can be successfully treated by addressing the underlying acquired cause(s) of the elevated triglycerides, such as reducing the amount of dietary fat intake, treating uncontrolled co-morbid diseases such as T2DM (Type 2 diabetes mellitus), discontinuing offending medications, and initiating lipid lowering medications such as fibrates, omega-3 fatty acids, or nicotinic acid derivatives (niacin) [Chylomicronemia Syndrome. Chait A., Brunzell J. Adv Intern Med 5 1992. 37:249-73.].

Despite optimal therapy, some Type V patients continue to have elevated triglyceride levels. There is thus a need for new methods of treating Type V hyperlipoproteinemia.

Therapeutic Definitions

As used herein, "treatment" includes curative and prophylactic treatment. As used herein, a "patient" means an animal, preferably a mammal, preferably a human, in need of treatment.

The amount of the compound of the invention administered should be a therapeutically effective amount where the compound or derivative is used for the treatment of a disease or condition and a prophylactically effective amount where the compound or derivative is used for the prevention of a disease or condition.

The term "therapeutically effective amount" used herein refers to the amount of compound needed to treat or ameliorate a targeted disease or condition. The term "prophylactically effective amount" used herein refers to the amount of compound needed to prevent a targeted disease or condition. The exact dosage will generally be dependent on the patient's status at the time of administration. Factors that may be taken into consideration when determining dosage include the severity of the disease state in the patient, the general health of the patient, the age, weight, gender, diet, time, frequency and route of administration, drug combinations, reaction sensitivities and the patient's tolerance or response to therapy. The precise amount can be determined by routine experimentation, but may ultimately lie with the judgement of the clinician. Generally, an effective dose will be from 0.01 mg/kg/day (mass of drug compared to mass of patient) to 1000 mg/kg/day, e.g. 1 mg/kg/day to 100 mg/kg/day. Compositions may be administered individually to a patient or may be administered in combination with other agents, drugs or hormones.

Administration & Formulation

General

For pharmaceutical use, the compounds of the invention may be administered as a medicament by enteral or parenteral routes, including intravenous, intramuscular, subcutaneous, transdermal, airway (aerosol), oral, intranasal, rectal, vaginal and topical (including buccal and sublingual) administration. The compounds of formula (I) should be assessed for their biopharmaceutical properties, such as solubility and solution stability (across pH), permeability, etc., in order to select the most appropriate dosage form and route of administration for treatment of the proposed indication.

The compounds of the invention may be administered as crystalline or amorphous products. The compounds of the invention may be administered alone or in combination with one or more other compounds of the invention or in combination with one or more other drugs (or as any combination thereof). Generally, they will be administered as a formulation in association with one or more pharmaceutically acceptable excipients. The term "excipient" includes any ingredient other than the compound(s) of the invention which may impart either a functional (e.g. drug release rate controlling) and/or a non-functional (e.g. processing aid or diluent) characteristic to the formulations. The choice of excipient will to a large extent depend on factors such as the particular mode of administration, the effect of the excipient on solubility and stability, and the nature of the dosage form.

Typical pharmaceutically acceptable excipients include:
  diluents, e.g. lactose, dextrose, sucrose, mannitol, sorbitol, cellulose and/or glycine;
  lubricants, e.g. silica, talcum, stearic acid, its magnesium or calcium salt and/or polyethyleneglycol;
  binders, e.g. magnesium aluminum silicate, starch paste, gelatin, tragacanth, methylcellulose, sodium carboxymethylcellulose and/or polyvinylpyrrolidone;

disintegrants, e.g. starches, agar, alginic acid or its sodium salt, or effervescent mixtures; and/or absorbants, colorants, flavors and/or sweeteners.

A thorough discussion of pharmaceutically acceptable excipients is available in Gennaro, *Remington: The Science and Practice of Pharmacy* 2000, 20th edition (ISBN: 0683306472). Accordingly, in one embodiment, the present invention provides a pharmaceutical composition comprising a compound of formula (I) and a pharmaceutically acceptable excipient.

General Galenic Aspects

In another aspect, the present invention provides a pharmaceutical composition comprising a compound of the present invention, or a pharmaceutically acceptable salt thereof, and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Dosage Forms

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

Combination Therapy

The compound of formula (I) may be administered alone, or may be administered in combination with another therapeutic agent (i.e. a different agent to the compound of formula (I)). Preferably, the compound of the invention and the other therapeutic agent are administered in a therapeutically effective amount.

The compound of the present invention may be administered either simultaneously with, or before or after, the other therapeutic agent. The compound of the present invention may be administered separately, by the same or different route of administration, or together in the same pharmaceutical composition.

In one embodiment, the invention provides a product comprising a compound of formula (I) and another therapeutic agent as a combined preparation for simultaneous, separate or sequential use in therapy. In one embodiment, the therapy is the treatment of a disease or condition mediated by DGAT1. Products provided as a combined preparation include a composition comprising the compound of formula (I) and the other therapeutic agent together in the same pharmaceutical composition, or the compound of formula (I) and the other therapeutic agent in separate form, e.g. in the form of a kit.

In one embodiment, the invention provides a pharmaceutical composition comprising a compound of formula (I) and another therapeutic agent. Optionally, the pharmaceutical composition may comprise a pharmaceutically acceptable excipient, as described above in "Administration & Formulation".

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) in the manufacture of a medicament for treating a disease or condition mediated by DGAT1, wherein the medicament is prepared for administration with another therapeutic agent. The invention also provides the use of a another therapeutic agent in the manufacture of medicament for treating a disease or condition mediated by DGAT1, wherein the medicament is prepared for administration with a compound of formula (I).

The invention also provides a compound of formula (I) for use in a method of treating a disease or condition mediated by DGAT1, wherein the compound of formula (I) is prepared for administration with another therapeutic agent. The invention also provides another therapeutic agent for use in a method of treating a disease or condition mediated by DGAT1, wherein the other therapeutic agent is prepared for administration with a compound of formula (I). The invention also provides a compound of formula (I) for use in a method of treating a disease or condition mediated by DGAT1, wherein the compound of formula (I) is administered with another therapeutic agent. The invention also provides another therapeutic agent for use in a method of treating a disease or condition mediated by DGAT1, wherein the other therapeutic agent is administered with a compound of formula (I).

The invention also provides the use of a compound of formula (I) in the manufacture of a medicament for treating a disease or condition mediated by DGAT1, wherein the patient has previously (e.g. within 24 hours) been treated with another therapeutic agent. The invention also provides the use of another therapeutic agent in the manufacture of a medicament for treating a disease or condition mediated by DGAT1, wherein the patient has previously (e.g. within 24 hours) been treated with a compound of formula (I).

In one embodiment, the other therapeutic agent is selected from:

antidiabetic agents, such as insulin, insulin derivatives and mimetics; insulin secretagogues such as the sulfonylureas, e.g. Glipizide, glyburide and Amaryl; insulinotropic sulfonylurea receptor ligands such as meglitinides, e.g. nateglinide and repaglinide; protein tyrosine phosphatase-1B (PTP-1B) inhibitors such as PTP-112; Cholesteryl ester transfer protein (CETP) inhibitors such as torcetrapib, GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as vildagliptin;

hypolipidemic agents such as 3-hydroxy-3-methyl-glutaryl coenzyme A (HMG-CoA) reductase inhibitors, e.g. lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin;

anti-obesity agents such as orlistat or rimonabant;

anti-hypertensive agents, e.g. loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors;

agonists of peroxisome proliferator-activator receptors, such as fenofibrate, pioglitazone, rosiglitazone, tesaglitazar, BMS-298585, L-796449, the compounds specifically described in the patent application WO 2004/103995 i.e. compounds of examples 1 to 35 or compounds specifically listed in claim 21, or the compounds specifically described in the patent application WO 03/043985 i.e. compounds of examples 1 to 7 or compounds specifically listed in claim 19 and especially (R)-1-{4-[5-methyl-2-(4-trifluoromethyl-phenyl)-oxazol-4-ylmethoxy]-benzenesulfonyl}-2,3-dihydro-1H-indole-2-carboxylic or a salt thereof; and the specific anti-diabetic compounds described in *Expert Opin Investig Drugs* 2003, 12(4): 623-633, FIGS. 1 to 7.

General Methods of Preparation

Specific methods for the preparation of the compounds of the invention are disclosed in detail below in the Examples.

In general, compounds of formula (I) may be prepared by the reaction schemes described below.

Compound of the invention in which ring A is a oxadiazole can be prepared by reacting the aniline (1) with 1,1'-thiocarbonyldipyridin-2(1H)-one (2). The isothiocyanate (3) is then reacted with carbohydrazides (4) to form the hydrazinecarbothioamide (5). Cyclization with 3-(ethyliminomethylene-amino)-N,N-dimethyl-propan-1-amine (EDC) to form a compound of the invention represented by formula I. Compounds represented by formula IA in which ring A is a oxadiazole and ring B is a phenyl can be prepared using the reactions of Scheme I but also in the alternative method shown in Scheme II and III.

Compounds represented by formula IA in which ring A is oxadiazole and B is phenyl can be prepared from the Suzuki coupling of the pinacol boronate ester (6) and the corresponding biphenyl bromide (7), as indicated in Scheme II. Alternatively, compounds represented by formula IA in which ring A is oxadizole and B is pyridine can be prepared by reacting the oxadiazole (8) with the corresponding pinacol boronate ester (9), as indicated in Scheme III. Compounds represented by formula IIA in which ring A is a thiadiazoles can be prepared using the reactions in scheme 1. Cyclization of the hydrazinecarbothioamide with sulphuric acid in the presence of ethanol afford the compound of the invention represented by formula IIA.

Scheme I: Method of preparing compounds of the invention wherein Ring A is a oxadiazoles or thiadiazoles

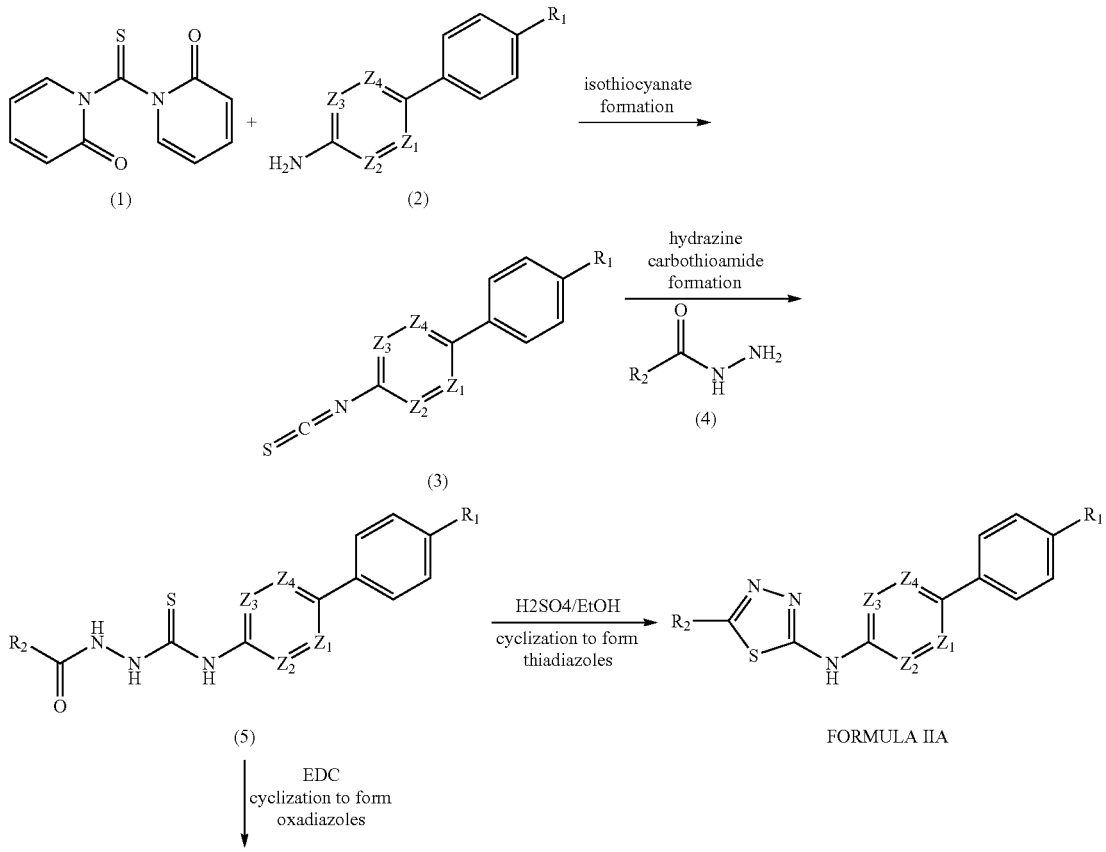

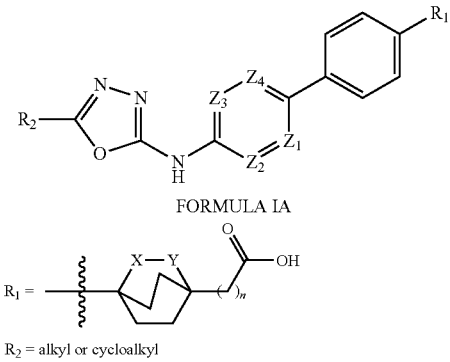

FORMULA IA

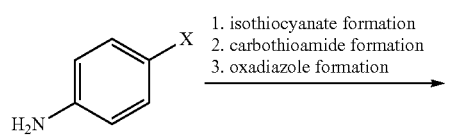

R₂ = alkyl or cycloalkyl

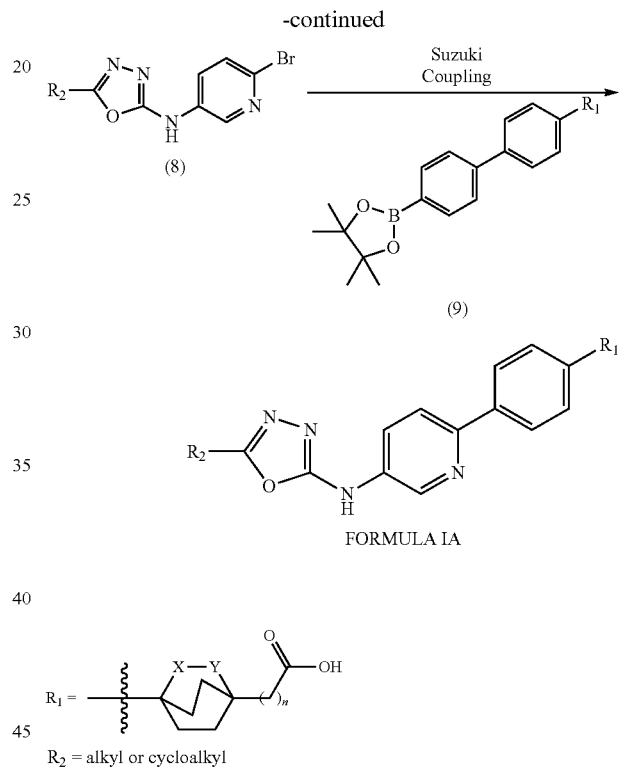

FORMULA IA

In general, compounds of formula (IVA) and (VA) may be prepared by the reaction schemes below.

Scheme II: Alternate method of preparing compounds of the invention wherein Ring A is oxadiazole

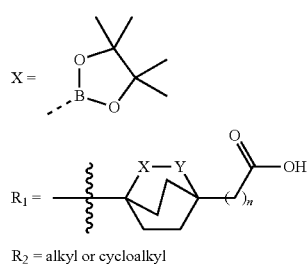

Scheme IV: Method of preparing 4-phenyl-2-oxabicyclo[2.2.2]octane containing compounds

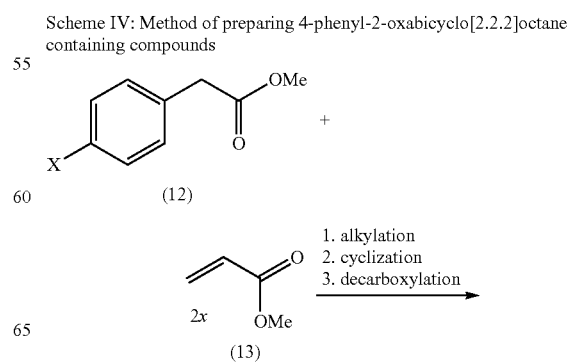

Scheme III: Alternate method of preparing compounds of the invention wherein Ring A is oxadiazole

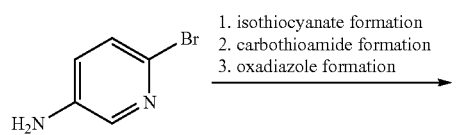

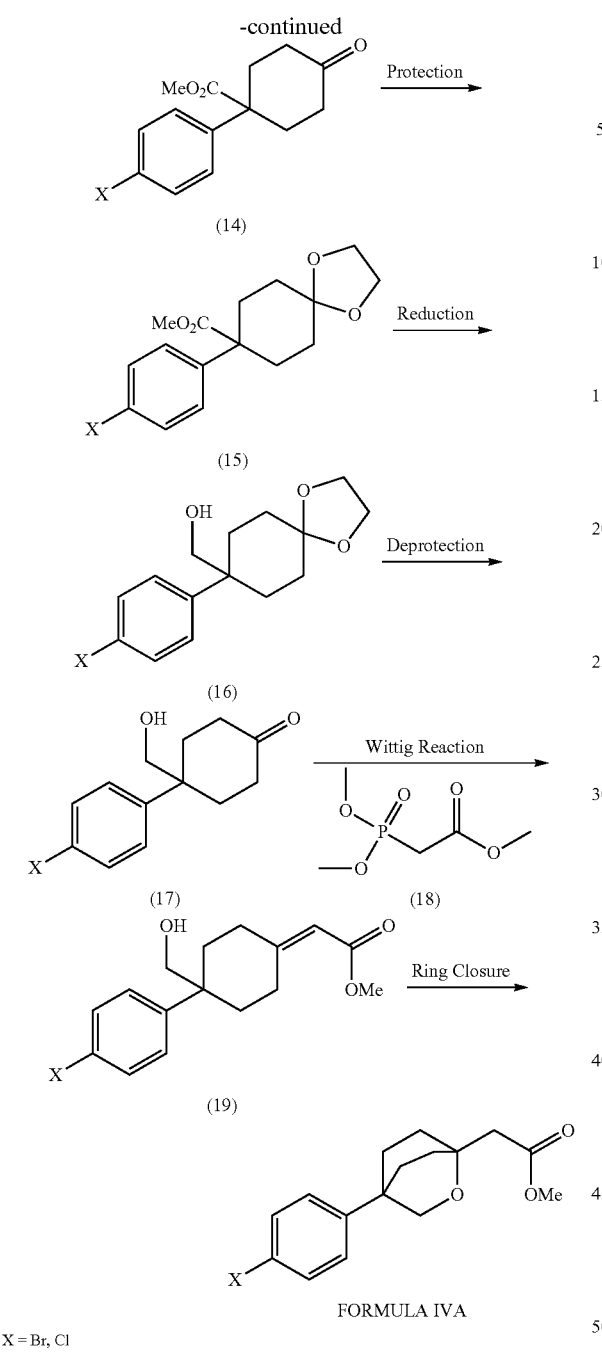

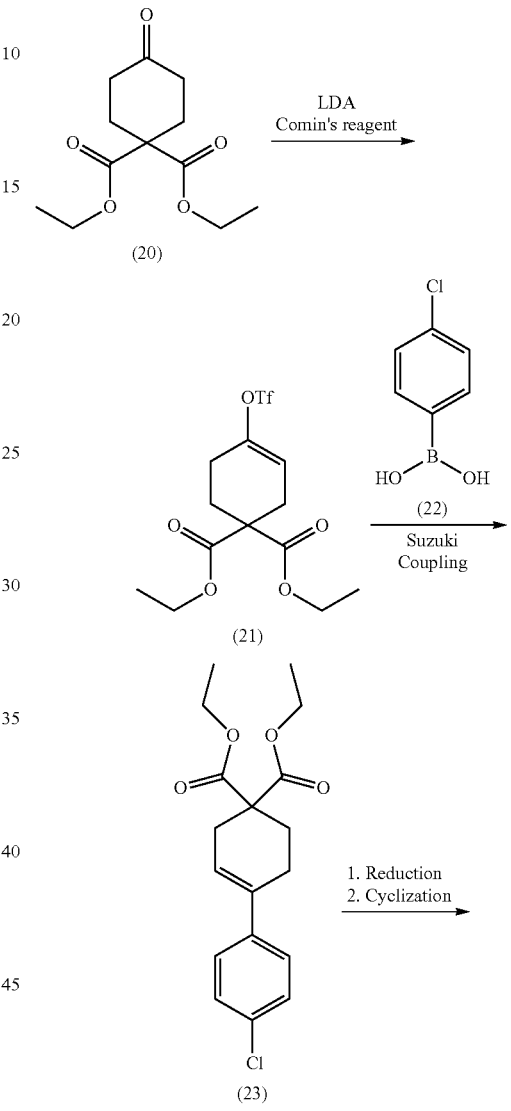

homologation afforded the enol ether (25). Oxidation and subsequent reduction allowed the formation of a compound of the invention represented by formula VA.

Scheme V: Method of preparing 1-phenyl-2-oxabicyclo[2.2.2]octane compounds 4-phenyl-2-oxabicyclo[2.2.2]octane can be prepared by reacting the ketone (12) with methyl acrylate (13). Subsequent ring closure followed by decarboxylation afforded the cyclohexanone compound (14), which is protected to form the acetal (15). Reduction, followed by deprotection of the acetal formed the primary alcohol (17). Reaction with trimethyl phosphonacetate, followed by base promoted intra-molecular cyclization allowed the formation of a compound of the invention represented by formula IVA.

1-phenyl-2-oxabicyclo[2.2.2]octane can be prepared by reacting the ketone (20) with Comin's Reagent in the presence of base to afford intermediate (21). Suzuki coupling with the boronic acid (22) followed by reduction and cyclization afforded the primary alcohol (24). Oxidation, followed by

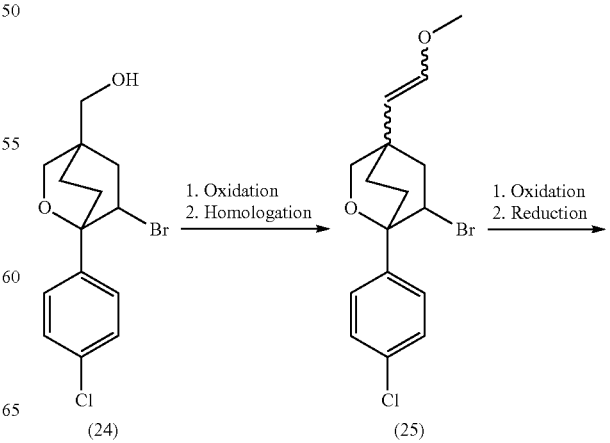

25

-continued

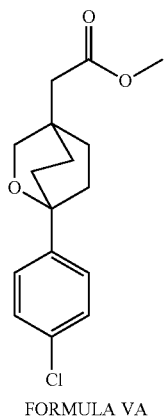 [SMILES: COC(=O)CC12CCC(c3ccc(Cl)cc3)(CC1)OC2]

FORMULA VA

In general, compounds of formula (XIA) may be prepared by the reaction scheme below.

7-oxabicyclo[2.2.1]heptan-1-yl compounds can be prepared by reacting the ketone (47) with the in-situ generated Grignard reagent (48), affording the tertiary alcohol (49). Deprotection, followed by Wittig generated the ester (50). Finally, a base promoted intra-molecular cyclization allowed the formation of a compound of the invention represented by formula XIA.

Scheme XI: Method of preparing compounds of the invention wherein D is a 7-oxabicyclo[2.2.1]heptan-1-yl

26

In general, compounds of formula (XIIA) may be prepared by the reaction scheme below.

7-oxabicyclo[2.2.1]heptan-1-yl propanoic acid compounds can be prepared by reacting the ketone (47) with phosphonium-ylide via Wittig reaction, followed by deprotection to afford the alkene (51). Reaction with the in-situ generated Grignard reagent (48) afforded the tertiary alcohol (52). Iodine promoted cyclization generated the bicyclo ring intermediate (53), which can be converted to the bis-methyl ester (55) via alkylation with dimethyl malonate (54). Final decarboxylation step allowed the formation of a compound of the invention represented by formula XIIA.

Scheme XII: Method of preparing 7-oxabicyclo[2.2.1]heptan-1-yl propanoic acid compounds

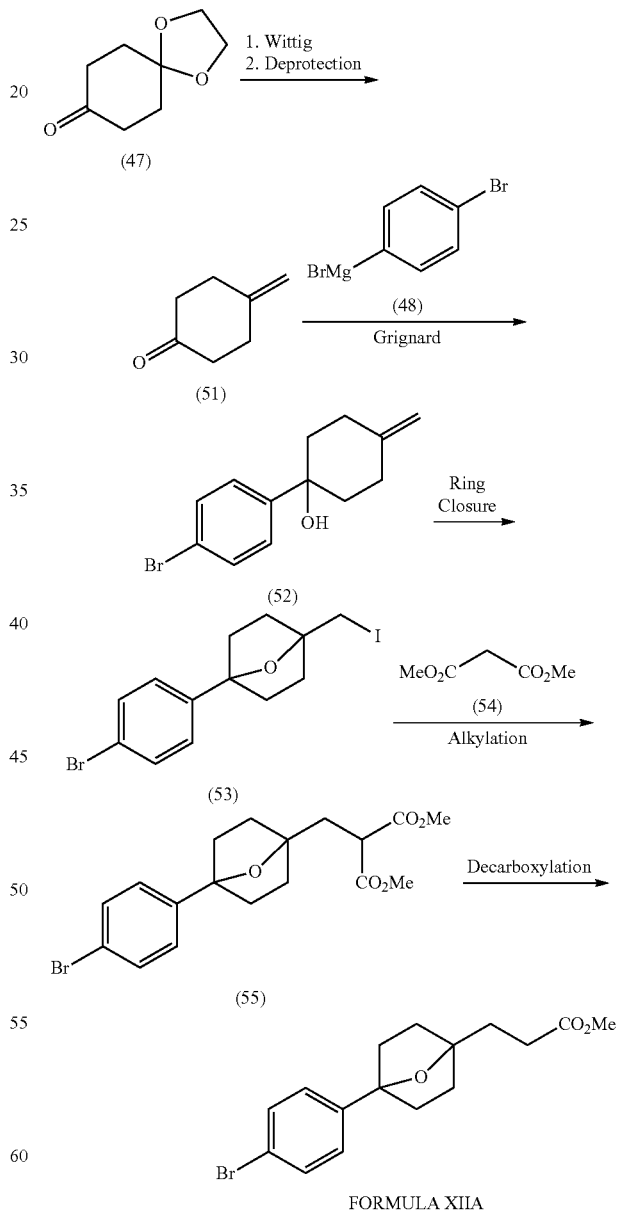

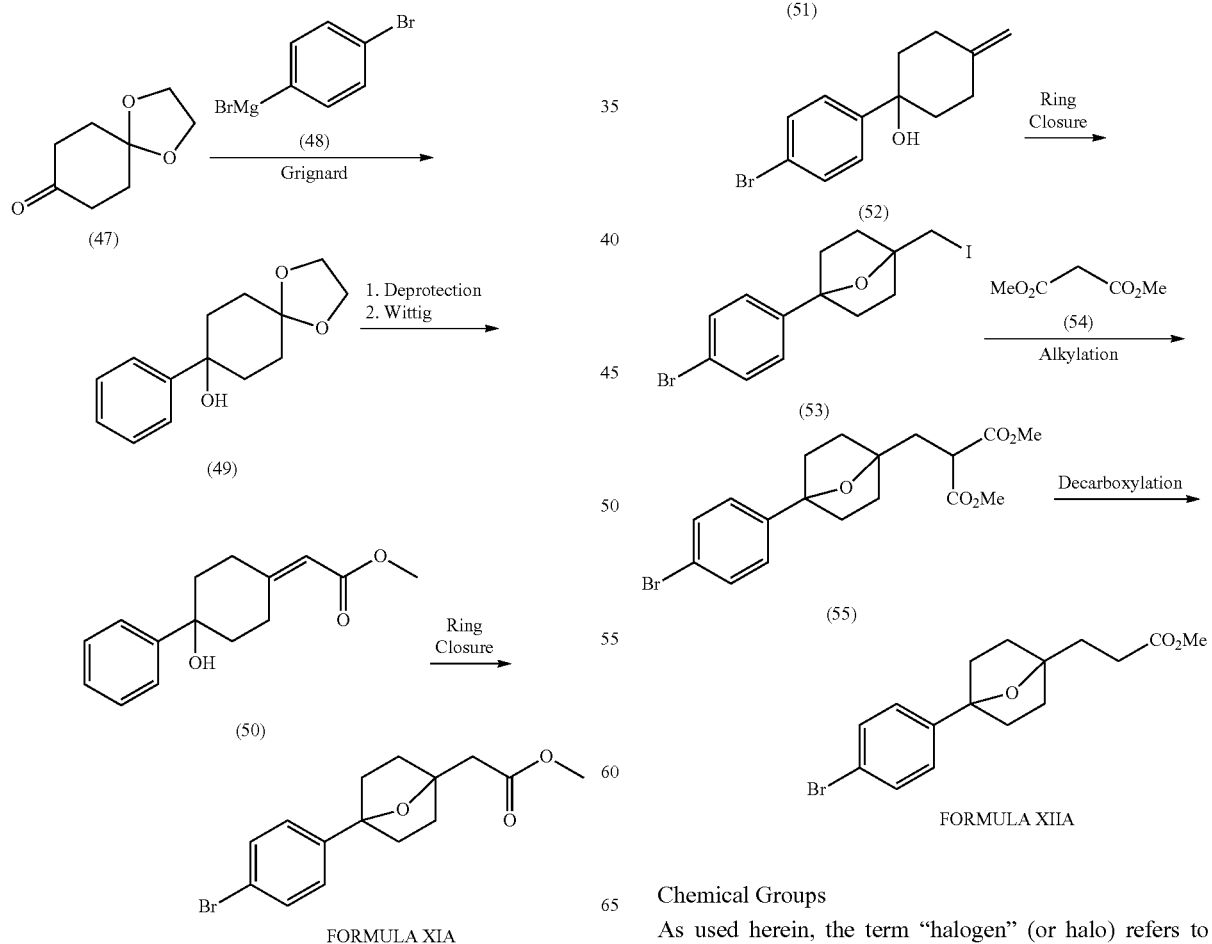

Chemical Groups

As used herein, the term "halogen" (or halo) refers to fluorine, bromine, chlorine or iodine, in particular fluorine, chlorine. Halogen-substituted groups and moieties, such as alkyl substituted by halogen (haloalkyl) can be mono-, poly- or per-halogenated.

As used herein, the term "hetero atoms" refers to nitrogen (N), oxygen (O) or sulphur (S) atoms, in particular nitrogen or oxygen.

As used herein, the term "alkyl" refers to a fully saturated branched or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. A substituted alkyl is an alkyl group containing one or more, such as one, two or three substituents selected from halogen, hydroxy or alkoxy groups.

As used herein, the term "alkylene" refers to divalent alkyl group as defined herein above having 1 to 20 carbon atoms. It comprises 1 to 20 carbon atoms, Unless otherwise provided, alkylene refers to moieties having 1 to 16 carbon atoms, 1 to 10 carbon atoms, 1 to 7 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

A substituted alkylene is an alkylene group containing one or more, such as one, two or three substituents selected from halogen, hydroxy or alkoxy groups.

As used herein, the term "haloalkyl" refers to an alkyl as defined herein, which is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have 1-16, 1-10, 1-7, more preferably 1-4 carbon atoms.

A substituted alkoxy is an alkoxy group containing one or more, such as one, two or three substituents selected from halogen, hydroxy or alkoxy groups.

Similarly, each alkyl part of other groups like "alkylaminocrabonyl", "alkoxyalkyl", "alkoxycarbonyl", "alkoxy-carbonylalkyl", "alkylsulfonyl", "alkylsulfoxyl", "alkylamino", "haloalkyl" shall have the same meaning as described in the above-mentioned definition of "alkyl".

As used herein, the term "cycloalkyl" refers to saturated or unsaturated monocyclic, bicyclic, tricyclic or spirocyclic hydrocarbon groups of 3-12 carbon atoms. Unless otherwise provided, cycloalkyl refers to cyclic hydrocarbon groups having between 3 and 9 ring carbon atoms or between 3 and 7 ring carbon atoms.

A substituted cycloalkyl is a cycloalkyl group substituted by one, or two, or three, or more substituents independently selected from the group consisting of hydroxyl, thiol, cyano, nitro, oxo, alkylimino, $C_1$-$C_4$-alkyl, $C_1$-$C_4$-alkenyl, $C_1$-$C_4$-alkynyl, $C_1$-$C_4$-alkoxy, $C_1$-$C_4$-thioalkyl, $C_1$-$C_4$-alkenyloxy, $C_1$-$C_4$-alkynyloxy, halogen, $C_1$-$C_4$-alkylcarbonyl, carboxy, $C_1$-$C_4$-alkoxycarbonyl, amino, $C_1$-$C_4$-alkylamino, di-$C_1$-$C_4$-alkylamino, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl($C_1$-$C_4$-alkyl)amino, sulfonyl, sulfamoyl, alkylsulfamoyl, $C_1$-$C_4$-alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_1$-$C_4$-alkoxy groups. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

Similarly, each cycloalkyl part of other groups like "cycloalkyloxy", "cycloalkoxyalkyl", "cycloalkoxycarbonyl", "cycloalkoxy-carbonylalkyl", "cycloalkylsulfonyl", "halocycloalkyl" shall have the same meaning as described in the above-mentioned definition of "alkyl".

As used herein, the term "aryl" refers to an aromatic hydrocarbon group having 6-20 carbon atoms in the ring portion. Typically, aryl is monocyclic, bicyclic or tricyclic aryl having 6-20 carbon atoms. Furthermore, the term "aryl" as used herein, refers to an aromatic substituent which can be a single aromatic ring, or multiple aromatic rings that are fused together. Non-limiting examples include phenyl, naphthyl or tetrahydronaphthyl.

A substituted aryl is an aryl group substituted by 1-5 (such as one, or two, or three) substituents independently selected from the group consisting of hydroxyl, thiol, cyano, nitro, $C_1$-$C_4$-alkyl, $C_1$-$C_4$-alkenyl, $C_1$-$C_4$-alkynyl, $C_1$-$C_4$-alkoxy, $C_1$-$C_4$-thioalkyl, $C_1$-$C_4$-alkenyloxy, $C_1$-$C_4$-alkynyloxy, halogen, $C_1$-$C_4$-alkylcarbonyl, carboxy, $C_1$-$C_4$-alkoxycarbonyl, amino, $C_1$-$C_4$-alkylamino, di-$C_1$-$C_4$-alkylamino, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl($C_1$-$C_4$-alkyl)amino, sulfonyl, sulfamoyl, alkylsulfamoyl, $C_1$-$C_4$-alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_1$-$C_4$-alkoxy groups.

Similarly, each aryl part of other groups like "aryloxy", "aryloxyalkyl", "aryloxycarbonyl", "aryloxy-carbonylalkyl" shall have the same meaning as described in the above-mentioned definition of "aryl".

As used herein, the term "heterocyclyl" refers to a heterocyclic radical that saturated or partially saturated and is preferably a monocyclic or a polycyclic ring (in case of a polycyclic ring particularly a bicyclic, tricyclic or spirocyclic ring); and has 3 to 24, more preferably 4 to 16, most preferably 5 to 10 and most preferably 5 or 6 ring atoms; wherein one or more, preferably one to four, especially one or two ring atoms are a heteroatom (the remaining ring atoms therefore being carbon). The bonding ring (i.e. the ring connecting to the molecule) preferably has 4 to 12, especially 5 to 7 ring atoms. The term heterocyclyl excludes heteroaryl. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like A substituted heterocyclyl is a heterocyclyl group independently substituted by 1-5 (such as one, or two, or three) substituents selected from hydroxyl, thiol, cyano, nitro, oxo, alkylimino, $C_1$-$C_4$-alkyl, $C_1$-$C_4$-alkenyl, $C_1$-$C_4$-alkynyl, $C_1$-$C_4$-alkoxy, $C_1$-$C_4$-thioalkyl, $C_1$-$C_4$-alkenyloxy, $C_1$-$C_4$-alkynyloxy, halogen, $C_1$-$C_4$-alkylcarbonyl, carboxy, $C_1$-$C_4$-alkoxycarbonyl, amino, $C_1$-$C_4$-alkylamino, di-$C_1$-$C_4$-alkylamino, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl($C_1$-$C_4$-alkyl)amino, sulfonyl, sulfamoyl, alkylsulfamoyl, $C_1$-$C_4$-alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_1$-$C_4$-alkoxy groups.

Similarly, each heterocyclyl part of other groups like "heterocyclyloxy", "heterocyclyloxyalkyl", "heterocyclyloxycarbonyl" shall have the same meaning as described in the above-mentioned definition of "heterocyclyl".

As used herein, the term "heteroaryl" refers to a 5-14 membered monocyclic- or bicyclic- or tricyclic-aromatic ring system, having 1 to 8 heteroatoms. Typically, the heteroaryl is a 5-10 membered ring system (e.g., 5-7 membered monocycle or an 8-10 membered bicycle) or a 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4-aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or l-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A substituted heteroaryl is a heteroaryl group containing one or more substituents selected from hydroxyl, thiol, cyano, nitro, $C_1$-$C_4$-alkyl, $C_1$-$C_4$-alkenyl, $C_1$-$C_4$-alkynyl, $C_1$-$C_4$-alkoxy, $C_1$-$C_4$-thioalkyl, $C_1$-$C_4$-alkenyloxy, $C_1$-$C_4$-alkynyloxy, halogen, $C_1$-$C_4$-alkylcarbonyl, carboxy, $C_1$-$C_4$-alkoxycarbonyl, amino, $C_1$-$C_4$-alkylamino, di-$C_1$-$C_4$-alkylamino, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl($C_1$-$C_4$-alkyl)amino, sulfonyl, sulfamoyl, alkylsulfamoyl, $C_1$-$C_4$-alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_1$-$C_4$-alkoxy groups.

Similarly, each heteroaryl part of other groups like "heteroaryloxy", "heteroaryloxyalkyl", "heteroaryloxycarbonyl" shall have the same meaning as described in the above-mentioned definition of "heteroaryl".

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

MODES FOR CARRYING OUT THE INVENTION

The following Examples are intended to illustrate the invention and are not to be construed as being limitations thereon. If not mentioned otherwise, all evaporations are performed under reduced pressure, between about 50 mmHg and 100 mmHg. The structure of final products, intermediates and starting materials is confirmed by standard analytical methods, e.g., microanalysis, melting point (m.p.) and spectroscopic characteristics, e.g. MS, IR and NMR. Abbreviations used are those conventional in the art.

The conditions for determining the mass and the retention times were as follows:

Condition E (LCMS: RXNMON_Neutral)

LC-MS method with Broad range (5-95%) gradient with neutral mobile phase (5 mM NH4+HCOO—). Electrospray mass spectra (+) and (−), DAD-UV chromatogram 210-400 nm, Gradient: 5-95% MeCN in 2 min (2 mL/min), 2 µL injection. Column: Inertsil C8-3, 3.0×433 mm×3.0 µm, 40 deg C.

Condition Z (HR/MS, pre OAA)

1.0 mL/min flow rate. 5% to 95% Acetonitrile (with 0.05% formic acid) gradient in 9.50 min, Aqueous phase modified with 0.1% formic acid. Column: Inertsil ODS-4 C18, 3 um, 3.0×100 mm.

LCUV/ESI-MS data was recorded on an Agilent 6220 with resolution of 11000 (FWHM).

Condition L (QT2, OAA HR/MS)

1.0 mL/min flow rate with the gradient from 2% to 98% ACN in 4.40 min, 3.75 mM Ammonium Acetate and 0.0005% Formic Acid used as the modifier additive in the Aqueous Phase. 0.04% of Formic Acid used as the modifier in the Organic Phase. Acquity UPLC CSH C18 2.1×50 mm 1.7 um column at 50 deg C., LCUV/ESI-MS data was recorded on an Acquity G2 Xevo QT of with resolution of >20000 (FWHM).

Condition M (SQ2, Purity-NpH)

1.0 mL/min flow rate with the gradient from 2% to 98% ACN in 4.40 min, 3.75 mM Ammonium Acetate and 2% acetonitrile used as the modifier additive in the Aqueous Phase. No additive was used as the modifier in the Organic Phase. Acquity UPLC CSH C18 2.1×50 mm 1.7 um column at 50 deg C.

Condition R (LCMS: RXNMON_Neutral, ZQ1)

LC-MS method with Broad range (5-95%) gradient with neutral mobile phase (5 mM NH4+HCOO—). Electrospray mass spectra (+) and (−), DAD-UV chromatogram 210-400 nm, Gradient: 5-95% MeCN in 2 min (2 mL/min), 2 μL injection. Column: X-bridge C18, 3.0 cm×30 mm×3.5 μm, 40° C.

Condition W (SQ4, RXNMON-Acidic)

1.0 mL/min flow rate with the gradient from 2% to 98% ACN in 1.70 min, 3.75 mM Ammonium Acetate and 0.05% Formic Acid used as the modifier additive in the Aqueous Phase. 0.04% of Formic Acid used as the modifier in the Organic Phase. Acquity UPLC BEH C18 2.1×50 mm 1.7 um column at 50 deg C.

| Ex. # | MW | Structure | IUPAC Name |
|---|---|---|---|
| 1 | 462.54 | 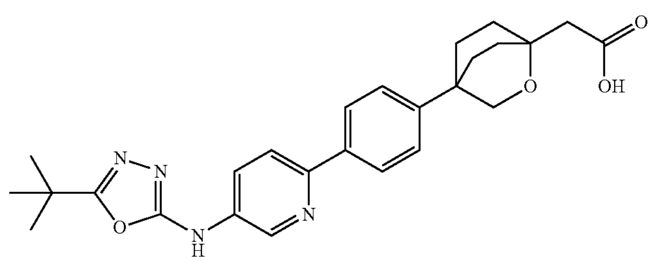 [SMILES: CC(C)(C)c1nnc(Nc2ccc(-c3ccc(C45CCC(CC(=O)O)(CC4)OC5)cc3)nc2)o1] | 2-(4-(4-(5-(5-tert-butyl-1,3,4-oxadiazol-2-ylamino)pyridin-2-yl)phenyl)-2-oxabicyclo[2.2.2]octan-1-yl)acetic acid |
| 2 | 460.52 | 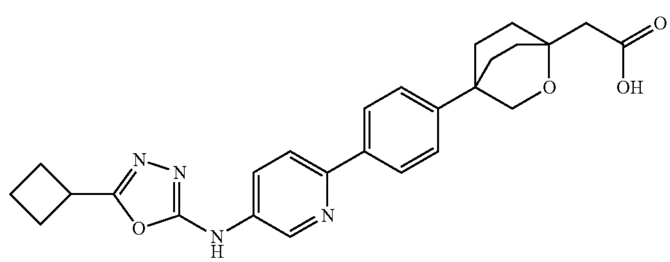 | 2-(4-(4-(5-((5-cyclobutyl-1,3,4-oxadiazol-2-yl)amino)pyridin-2-yl)phenyl)-2-oxabicyclo[2.2.2]octan-1-yl)acetic acid |
| 3 | 476.59 | 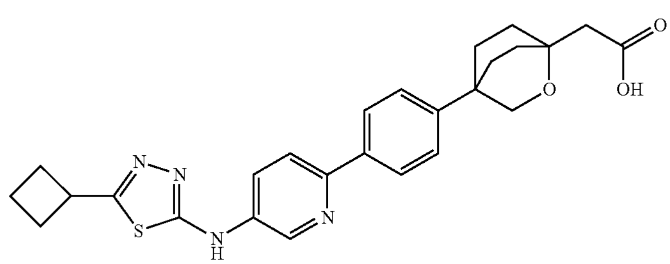 | 2-(4-(4-(5-((5-cyclobutyl-1,3,4-thiadiazol-2-yl)amino)pyridin-2-yl)phenyl)-2-oxabicyclo[2.2.2]octan-1-yl)acetic acid |
| 4 | 477.58 | 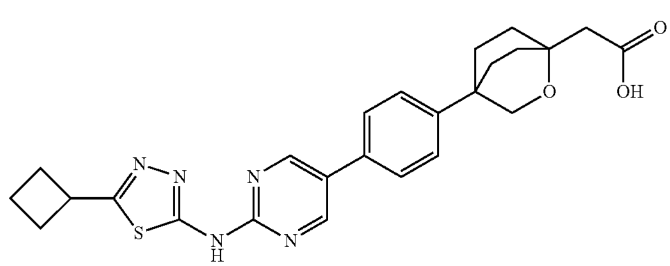 [SMILES: O=C(O)CC12CCC(c3ccc(-c4cnc(Nc5nnc(C6CCC6)s5)nc4)cc3)(CC1)CO2] | 2-(4-(4-(2-(5-cyclobutyl-1,3,4-thiadiazol-2-ylamino)pyrimidin-5-yl)phenyl)-2-oxabicyclo[2.2.2]octan-1-yl)acetic acid |

-continued

| Ex. # | MW | Structure | IUPAC Name |
|---|---|---|---|
| 5 | 476.59 | 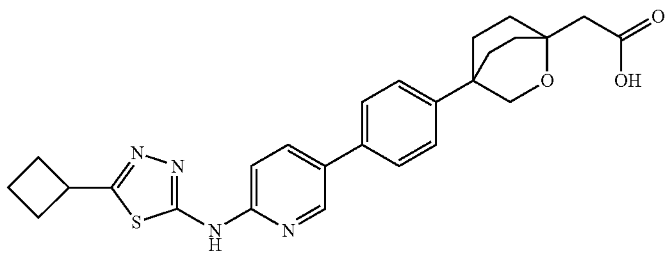 [SMILES: O=C(O)CC12CCC(c3ccc(-c4ccc(Nc5nnc(C6CCC6)s5)nc4)cc3)(CC1)CO2] | 2-(4-(4-(6-((5-cyclobutyl-1,3,4-thiadiazol-2-yl)amino)pyridin-3-yl)phenyl)-2-oxabicyclo[2.2.2]octan-1-yl)acetic acid |
| 6 | 475.60 | 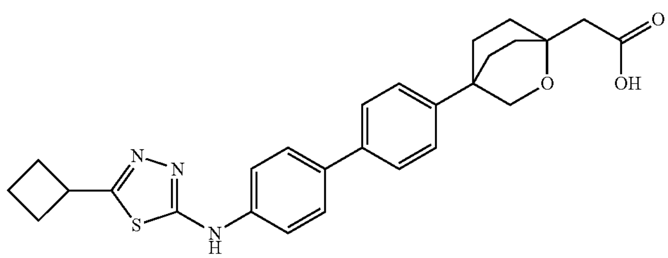 [SMILES: O=C(O)CC12CCC(c3ccc(-c4ccc(Nc5nnc(C6CCC6)o5)cc4)cc3)(CC1)CO2] | 2-(4-(4'-(5-cyclobutyl-1,3,4-thiadiazol-2-ylamino)biphenyl-4-yl)-2-oxabicyclo[2.2.2]octan-1-yl)acetic acid |
| 7 | 459.54 | 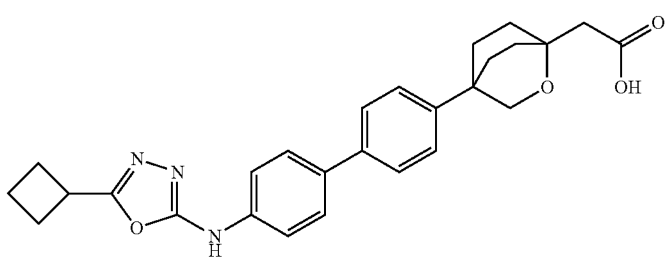 | 2-(4-(4'-(5-cyclobutyl-1,3,4-oxadiazol-2-ylamino)biphenyl-4-yl)-2-oxabicyclo[2.2.2]octan-1-yl)acetic acid |
| 8 | 461.55 | 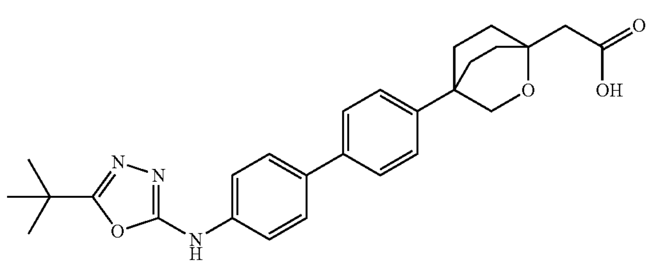 | 2-(4-(4'-(5-tert-butyl-1,3,4-oxadiazol-2-ylamino)biphenyl-4-yl)-2-oxabicyclo[2.2.2]octan-1-yl)acetic acid |
| 9 | 445.51 | 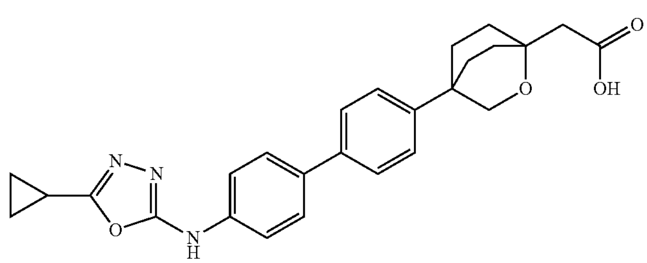 [SMILES: O=C(O)CC12CCC(c3ccc(-c4ccc(Nc5nnc(C6CC6)o5)cc4)cc3)(CC1)CO2] | 2-(4-(4'-((5-cyclopropyl-1,3,4-oxadiazol-2-yl)amino)-[1,1'-biphenyl]-4-yl)-2-oxabicyclo[2.2.2]octan-1-yl)acetic acid |
| 10 | 514.49 | 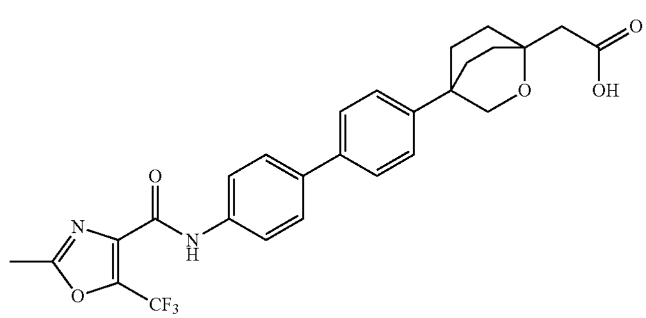 [SMILES: Cc1nc(C(=O)Nc2ccc(-c3ccc(C45CCC(CC(=O)O)(CC4)OC5)cc3)cc2)c(C(F)(F)F)o1] | 2-(4-(4-(5-(2-methyl-5-(trifluoromethyl)oxazole-4-carboxamido)pyridin-2-yl)phenyl)-2-oxabicyclo[2.2.2]octan-1-yl)acetic acid |

| Ex. # | MW | Structure | IUPAC Name |
|---|---|---|---|
| 11 | 474.55 | 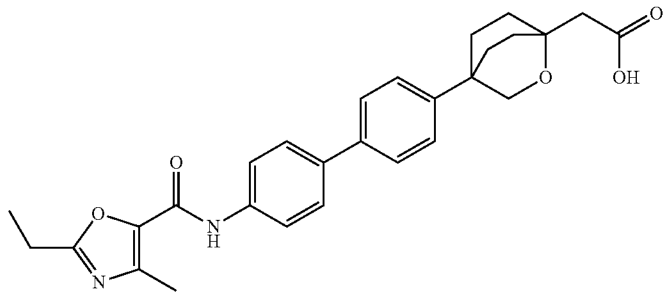 [SMILES: CCc1nc(C)c(C(=O)Nc2ccc(-c3ccc(C45CCC(CC(=O)O)(CC4)OC5)cc3)cc2)o1] | 2-(4-(4'-(2-ethyl-N,4-dimethyloxazole-5-carboxamido)-[1,1'-biphenyl]-4-yl)-2-oxabicyclo[2.2.2]octan-1-yl)acetic acid |
| 12 | 515.48 | 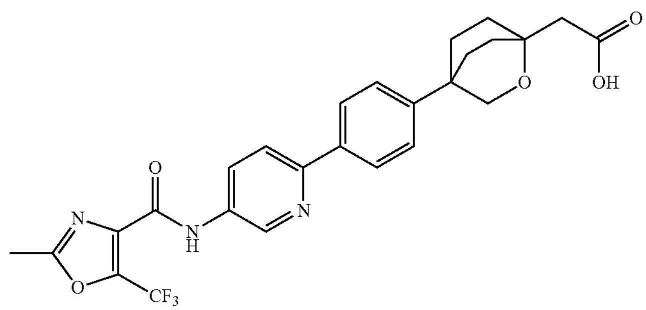 [SMILES: Cc1nc(C(=O)Nc2ccc(-c3ccc(C45CCC(CC(=O)O)(CC4)OC5)cc3)nc2)c(C(F)(F)F)o1] | 2-(4-(4-(5-(2-methyl-5-(trifluoromethyl)oxazole-4-carboxamido)pyridin-2-yl)phenyl)-2-oxabicyclo[2.2.2]octan-1-yl)acetic acid |
| 13 | 475.54 | 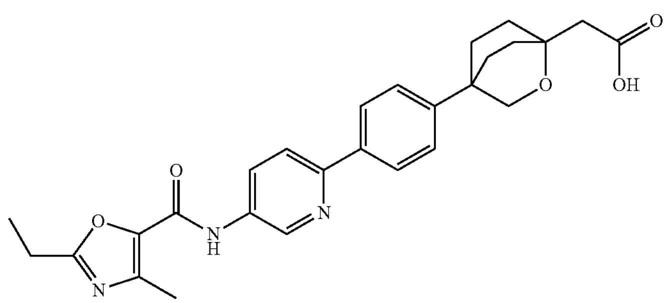 [SMILES: CCc1nc(C)c(C(=O)Nc2ccc(-c3ccc(C45CCC(CC(=O)O)(CC4)OC5)cc3)nc2)o1] | 2-(4-(4-(5-(2-ethyl-4-methyloxazole-5-carboxamido)pyridin-2-yl)phenyl)-2-oxabicyclo[2.2.2]octan-1-yl)acetic acid |
| 14 | 461.55 | 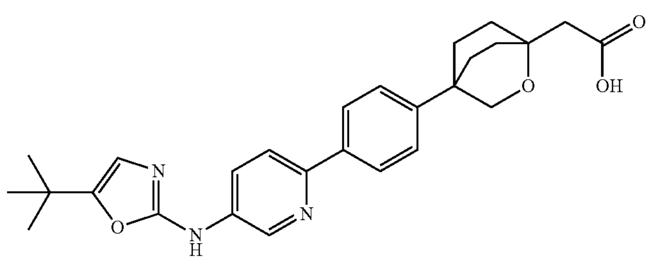 [SMILES: CC(C)(C)c1cnc(Nc2ccc(-c3ccc(C45CCC(CC(=O)O)(CC4)OC5)cc3)nc2)o1] | 2-(4-(4-(5-((5-(tert-butyl)oxazol-2-yl)amino)pyridin-2-yl)phenyl)-2-oxabicyclo[2.2.2]octan-1-yl)acetic acid |
| 15 | 460.56 | 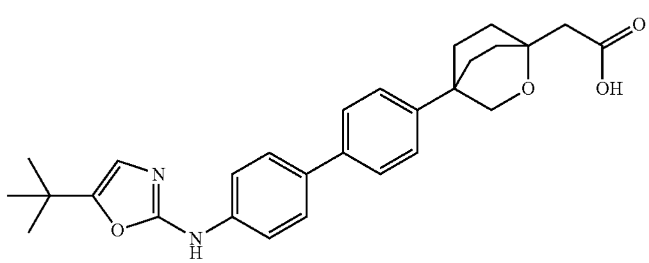 [SMILES: CC(C)(C)c1cnc(Nc2ccc(-c3ccc(C45CCC(CC(=O)O)(CC4)OC5)cc3)cc2)o1] | 2-(4-(4'-((5-(tert-butyl)oxazol-2-yl)amino)-[1,1'-biphenyl]-4-yl)-2-oxabicyclo[2.2.2]octan-1-yl)acetic acid |

| Ex. # | MW | Structure | IUPAC Name |
|---|---|---|---|
| 16 | 461.55 | 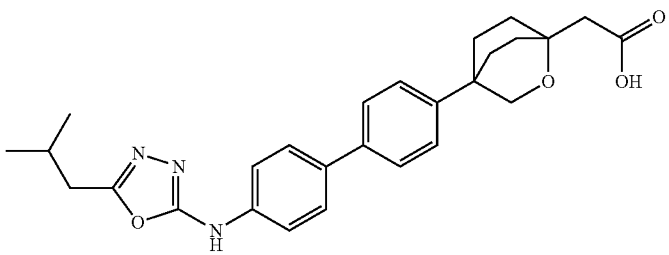 [SMILES: CC(C)Cc1nnc(Nc2ccc(-c3ccc(C45CCC(CC(=O)O)(CC4)OC5)cc3)cc2)o1] | 2-(4-(4'-((5-isobutyl-1,3,4-oxadiazol-2-yl)amino)-[1,1'-biphenyl]-4-yl)-2-oxabicyclo[2.2.2]octan-1-yl)acetic acid |
| 17 | 475.58 | 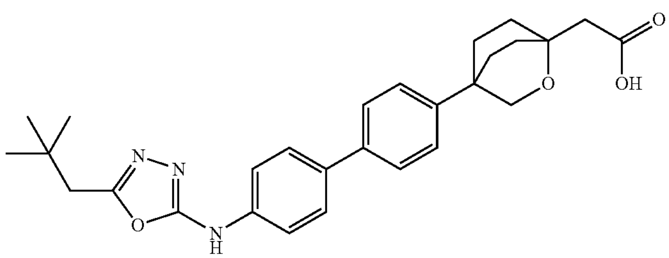 [SMILES: CC(C)(C)Cc1nnc(Nc2ccc(-c3ccc(C45CCC(CC(=O)O)(CC4)OC5)cc3)cc2)o1] | 2-(4-(4'-((5-neopentyl-1,3,4-oxadiazol-2-yl)amino)-[1,1'-biphenyl]-4-yl)-2-oxabicyclo[2.2.2]octan-1-yl)acetic acid |
| 18 | 474.55 | 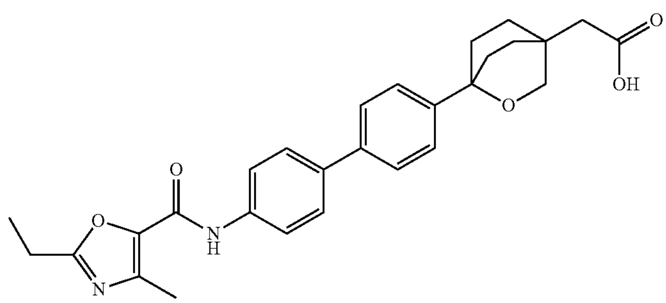 [SMILES: CCc1nc(C)c(C(=O)Nc2ccc(-c3ccc(C45CCC(CC(=O)O)(CC4)CO5)cc3)cc2)o1] | 2-(1-(4'-(2-ethyl-4-methyloxazole-5-carboxamido)-[1,1'-biphenyl]-4-yl)-2-oxabicyclo[2.2.2]octan-4-yl)acetic acid |
| 19 | 459.54 | 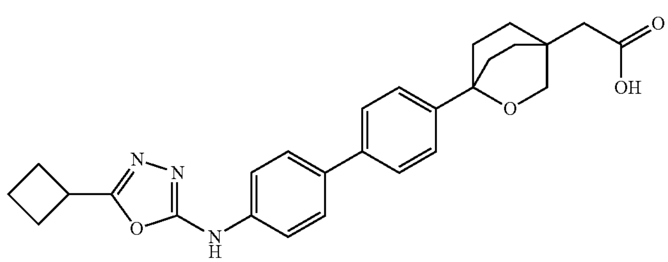 [SMILES: O=C(O)CC12CCC(c3ccc(-c4ccc(Nc5nnc(C6CCC6)o5)cc4)cc3)(CC1)OC2] | 2-(1-(4'-((5-cyclobutyl-1,3,4-oxadiazol-2-yl)amino)-[1,1'-biphenyl]-4-yl)-2-oxabicyclo[2.2.2]octan-4-yl)acetic acid |
| 20 | 461.55 | 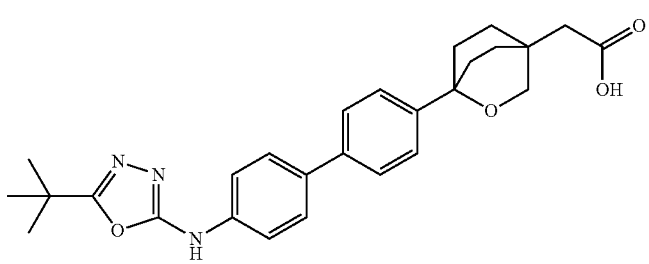 [SMILES: CC(C)(C)c1nnc(Nc2ccc(-c3ccc(C45CCC(CC(=O)O)(CC4)CO5)cc3)cc2)o1] | 2-(1-(4'-((5-(tert-butyl)-1,3,4-oxadiazol-2-yl)amino)-[1,1'-biphenyl]-4-yl)-2-oxabicyclo[2.2.2]octan-4-yl)acetic acid |
| 21 | 460.52 | 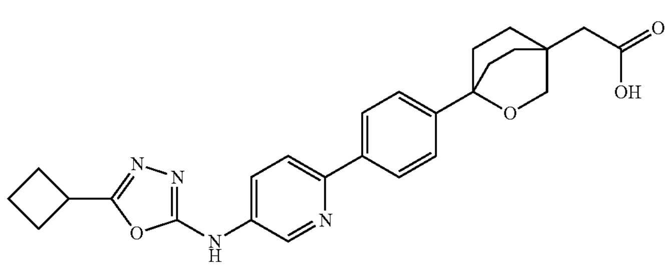 [SMILES: O=C(O)CC12CCC(c3ccc(-c4ccc(Nc5nnc(C6CCC6)o5)cn4)cc3)(CC1)OC2] | 2-(1-(4-(5-((5-cyclobutyl-1,3,4-oxadiazol-2-yl)amino)pyridin-2-yl)phenyl)-2-oxabicyclo[2.2.2]octan-4-yl)acetic acid |

| Ex. # | MW | Structure | IUPAC Name |
|---|---|---|---|
| 22 | 447.53 | 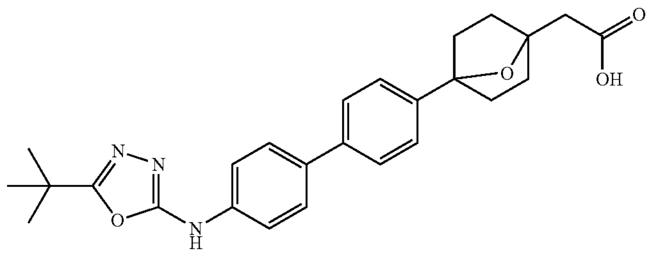 [SMILES: CC(C)(C)c1nnc(Nc2ccc(-c3ccc(C45CCC(CC(=O)O)(CC4)O5)cc3)cc2)o1] | 2-(4-(4'-((5-(tert-butyl)-1,3,4-oxadiazol-2-yl)amino)-[1,1'-biphenyl]-4-yl)-7-oxabicyclo[2.2.1]heptan-1-yl)acetic acid |
| 23 | 461.55 | 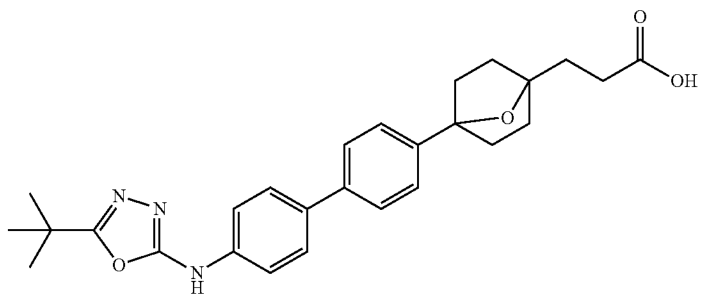 [SMILES: CC(C)(C)c1nnc(Nc2ccc(-c3ccc(C45CCC(CCC(=O)O)(CC4)O5)cc3)cc2)o1] | 3-(4-(4'-((5-(tert-butyl)-1,3,4-oxadiazol-2-yl)amino)-[1,1'-biphenyl]-4-yl)-7-oxabicyclo[2.2.1]heptan-1-yl)propanoic acid |

EXAMPLE 1

2-(4-(4-(5-(5-tert-butyl-1,3,4-oxadiazol-2-ylamino) pyridin-2-yl)phenyl)-2-oxabicyclo[2.2.2]octan-1-yl) acetic acid

Step 1. Synthesis of methyl 1-(4-bromophenyl)-4-oxocyclohexanecarboxylate

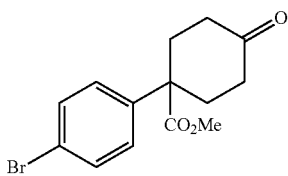 [SMILES: COC(=O)C1(c2ccc(Br)cc2)CCC(=O)CC1]

The title compound was prepared analogous to the literature procedure (*J. Org. Chem.*, 72, 7455, 2007) starting from methyl 2-(4-bromophenyl)acetate (5.78 g, 25.2 mmol) and methyl acrylate (4.78 g, 55.5 m mol). Column purification afforded the title compound as clear oil (4.64 g, 59% yield). LC/MS, ESI-MS(+): 311.1, RT: 1.26 (Condition E).

Step 2. Synthesis of methyl 8-(4-bromophenyl)-1,4-dioxaspiro[4.5]decane-8-carboxylate

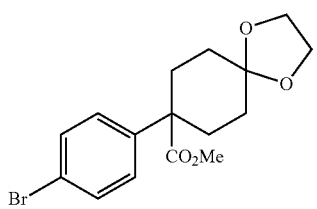 [SMILES: COC(=O)C1(c2ccc(Br)cc2)CCC2(CC1)OCCO2]

To a round bottom flask containing methyl 1-(4-bromophenyl)-4-oxocyclohexanecarboxylate (4.64 g, 14.91 mmol) was added toluene (33 ml), ethylene glycol (8.32 ml, 149 mmol) and p-toluenesulfonic acid (85 mg, 0.45 mmol) at room temperature. The mixture was heated to 80 C. for 2 hours. The content was then cooled to room temperature and quenched with a saturated solution of sodium bicarbonate. The organic portion was washed with saturated sodium bicarbonate and the aqueous portion extracted with MTBE twice. The combined organic portion was dried over sodium sulfate and concentrated to afford a crude oil. Column purification afforded the title compound as viscous oil (5.30 g, quantitative yield). LC/MS, ESI-MS(+): 357.1, RT: 1.38 (Condition E).

Step 3. Synthesis of (8-(4-bromophenyl)-1,4-dioxaspiro[4.5]decan-8-yl)methanol

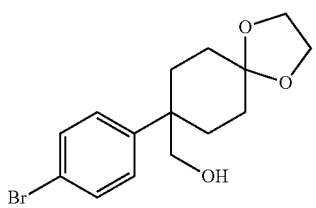 [SMILES: OCC1(c2ccc(Br)cc2)CCC2(CC1)OCCO2]

To a round bottom flask containing methyl 8-(4-bromophenyl)-1,4-dioxaspiro[4.5]decane-8-carboxylate (5.30 g, 14.92 mmol) was added anhydrous dichloromethane (60 ml) at room temperature. The content was then cool to −78° C. under a dry ice-acetone bath and DIBAL-H (31.1 ml, 37.30 mmol) in toluene was added dropwise slowly. When the addition was completed, the mixture was stirred at −78° C. for 30 minutes or until the consumption of the starting material as indicated by thin layer chromatography (TLC). The reaction was then quenched by the slow addition of a pH 8 buffered solution (prepared by mixing 0.53 mL ammonium hydroxide solution and 8.8 mL of saturated ammonium chloride solution) at −78° C. The mixture was then allowed to warm back up to room temperature and stirred for a further 45 minutes. Solid magnesium sulfate (8 g) was added and the mixture stirred at room temperature for another 30 minutes to afford free flowing slurry. The content was filtered and concentrated to afford the title compound as clear oil, which was used in the next step without purification (4.88 g). LC/MS, ESI-MS: non-ionizable, RT: 1.05 (Condition E).

Step 4. Synthesis of 4-(4-bromophenyl)-4-(hydroxymethyl)cyclohexanone

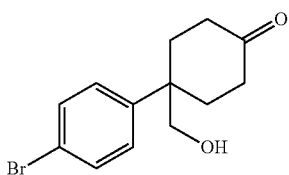 [SMILES: O=C1CCC(CO)(c2ccc(Br)cc2)CC1]

To a round bottom flask containing (8-(4-bromophenyl)-1,4-dioxaspiro[4.5]decan-8-yl)methanol (4.88 g, 14.91 mmol) was added acetone (34 ml) and water (17 ml) at room temperature. p-toluenesulfonic acid (57 mg, 0.30 mmol) was then added and the mixture heated to 75° C. for 1 hour. The content was cooled to room temperature and concentrated under reduced pressure to remove the excess acetone. The resulting aqueous mixture was extracted with EtOAc twice. The combined organic portion was dried over sodium sulfate and concentrated to afford the title compound as white solid. (4.22 g) LC/MS, ESI-MS: non-ionizable, RT: 1.05 (Condition E).

Step 5. Synthesis of methyl 2-(4-(4-bromophenyl)-4-(hydroxymethyl)cyclohexylidene)acetate

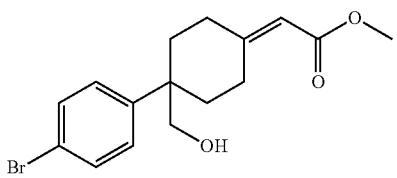 [SMILES: COC(=O)C=C1CCC(CO)(c2ccc(Br)cc2)CC1]

To a round bottom flask containing methanol (60 ml) was added sodium hydride (0.78 g, 19.37 mmol) portion-wise at room temperature under stirring, Trimethyl phosphonoacetate (2.58 ml, 17.88 mmol) was added drop-wise and the resulting mixture was stirred at room temperature for 30 minutes. To this mixture was then added 4-(4-bromophenyl)-4-(hydroxymethyl)cyclohexanone (4.22 g, 14.90 mmol) in several portions and stirred at room temperature for overnight. The reaction mixture was then quenched with a saturated solution of ammonium chloride and subsequently concentrated to remove excess methanol. The residue was taken in saturated ammonium chloride solution and extracted twice with EtOAc. The combined organic portion was dried over sodium sulfate and concentrated to afford a crude product. Column purification afforded the title compound as viscous oil (4.36 g, 86% yield). LC/MS, ESI-MS: non-ionizable, RT: 1.32 (Condition E).

Step 6. Synthesis of methyl 2-(4-(4-bromophenyl)-2-oxabicyclo[2.2.2]octan-1-yl)acetate

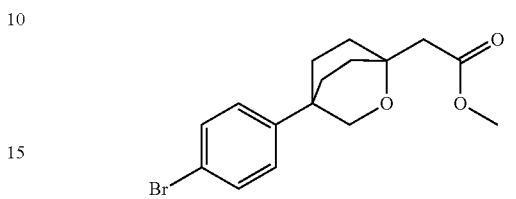

To a round bottom flask containing methyl 2-(4-(4-bromophenyl)-4-(hydroxymethyl)cyclohexylidene)acetate (4.36 g, 12.85 mmol) was added 1,4-dioxane (161 ml). The clear solution was cooled in an ice-bath and sodium hydride (0.67 g, 16.75 mmol) was then added portion-wise. After the addition, the mixture was warmed to room temperature and stirred for 10 minutes. After 10 minutes of stirring, the content was heated to 100° C. in an oil bath (with a reflux condenser) for 30 minutes. The reaction mixture was cooled to room temperature and quenched with a saturated solution of ammonium chloride and subsequently concentrated to remove excess dioxane. The residue was taken in saturated ammonium chloride solution and extracted twice with EtOAc. The combined organic portion was dried over sodium sulfate and concentrated to afford a crude product. Column purification afforded the title compound as white solid (3.4 g, 78% yield). LC/MS, ESI-MS: 341.2 (M+H$^+$), RT: 1.40 (Condition E).

Step 7. Synthesis of methyl 2-(4-(4-(4,4,5,5-tetramethyl-1,3,2-dioxaborolan-2-yl)phenyl)-2-oxabicyclo[2.2.2]octan-1-yl)acetate

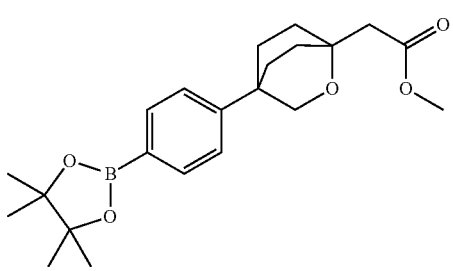

To a round bottom flask containing methyl 2-(4-(4-bromophenyl)-2-oxabicyclo[2.2.2]octan-1-yl)acetate (3.43 g, 10.11 mmol) was added bis(pinacolato)diboron (3.85 g, 15.17 mmol), potassium acetate (2.98 g, 30.3 mmol) and anhydrous 1,4-dioxane (48 ml). The mixture was stirred and degassed with nitrogen at room temperate for 15 minutes. PdCl$_2$(dppf) (0.41 g, 0.51 mmol) was then added and the mixture heated to 80° C. for overnight. The dark mixture was then cooled to room temperature and filtered over a pad of celite. The resulting filtrate was concentrated and column purified to afford the title compound as off-white solid (3.87 g, 99% yield). LC/MS, ESI-MS(+): 387.4, RT: 1.48 (Condition E).

Step 8. Synthesis of methyl2-(4-(4-(5-aminopyridin-2-yl)phenyl)-2-oxabicyclo[2.2.2]octan-1-yl)acetate

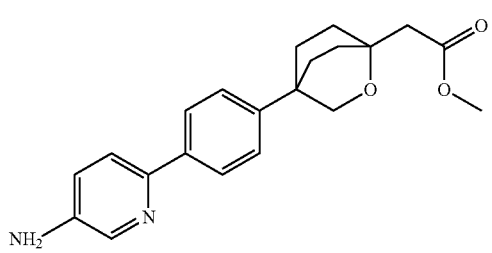 [SMILES: COC(=O)CC12CCC(c3ccc(-c4ccc(N)cn4)cc3)(CC1)CO2]

To a microwave vial containing methyl 2-(4-(4-(4,4,5,5-tetramethyl-1,3,2-dioxaborolan-2-yl)phenyl)-2-oxabicyclo[2.2.2]octan-1-yl)acetate (100 mg, 0.26 mmol), 6-bromopyridin-3-amine (49 mg, 0.28 mmol) and $Pd_2(PPh_3)_4$ (60 mg, 0.05 mmol) was added 1,4-dioxane (1.3 ml) at room temperature. 2N sodium carbonate (0.39 ml, 0.78 mmol) was added and the mixture was subjected to microwave radiation at 120° C. for 50 minutes. The resulting mixture was concentrated to dryness and taken up in EtOAc, the slurry was dried over sodium sulfate and filtered through a pad of celite. The filtrate was concentrated and purified by column chromatography to afford the title compound (120 mg, 65% yield). LC/MS, ESI-MS(+): 353.4, RT: 1.12 (Condition E).

Step 9. Synthesis of methyl 2-(4-(4-(5-(5-tert-butyl-1,3,4-oxadiazol-2-ylamino)pyridin-2-yl)phenyl)-2-oxabicyclo[2.2.2]octan-1-yl)acetate

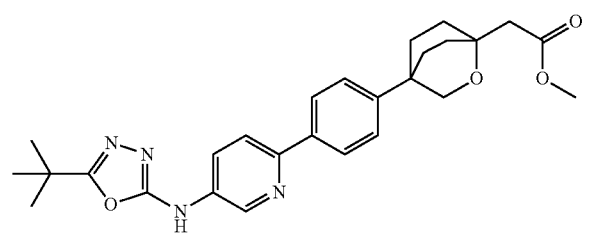 [SMILES: COC(=O)CC12CCC(c3ccc(-c4ccc(Nc5nnc(C(C)(C)C)o5)cn4)cc3)(CC1)CO2]

To a reaction vial containing methyl2-(4-(4-(5-aminopyridin-2-yl)phenyl)-2-oxabicyclo[2.2.2]octan-1-yl)acetate (120 mg, 0.23 mmol) was added dichloromethane (2 ml) at room temperature. 1,1'-thiocarbonyldipyridin-2(1H)-one (59 mg, 0.26 mmol) was added and stirred at room temperature for 1 hour to afford a bright orange mixture. Pivalohydrazine (40 mg, 0.35 mmol) was then added in one portion and the mixture stirred at room temperature for another hour. 1-ethyl-3-(3-dimethylaminopropyl)carbodiimide (80 mg, 0.42 mmol) was added and the mixture was stirred at room temperature for overnight. The content was then concentrated to dryness and the resulting residue was taken up in water to form a nice slurry. The slurry was filtered and washed with water, dried to afford the title compound as off-white solid (55 mg, 50% yield). LC/MS, ESI-MS(+): 477.4, RT: 1.31 (Condition E).

Step 10. Synthesis of 2-(4-(4-(5-(5-tert-butyl-1,3,4-oxadiazol-2-ylamino)pyridin-2-yl)phenyl)-2-oxabicyclo[2.2.2]octan-1-yl)acetic acid

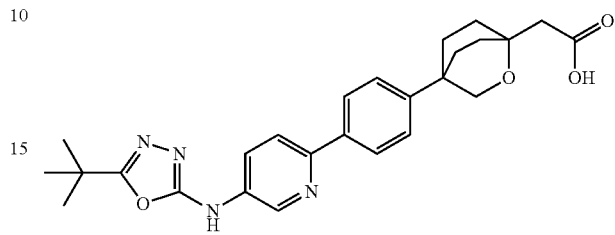

To a reaction vial containing methyl 2-(4-(4-(5-(5-tert-butyl-1,3,4-oxadiazol-2-ylamino)pyridin-2-yl)phenyl)-2-oxabicyclo[2.2.2]octan-1-yl)acetate (55 mg, 0.12 mmol) was added THF (1.5 ml) and a solution of 1N NaOH (0.35 ml, 0.35 mmol). The mixture was stirred vigorously at room temperature for overnight. The resulting mixture was concentrated to dryness and the residue was taken up in water. The mixture was acidified with 1N HCl to a pH of between 3 and 4 affording a thick residue. The residue was concentrated to dryness and taken up in MeOH to form fine slurry. The slurry was filtered and washed with small amount of MeOH and water to afford the title compound as white solid after drying (36 mg, 67% yield). HR/MS (M+H)$^+$ found 463.2354. calc. 463.2345. RT: 5.76 (Condition Z). $^1$H NMR (400 MHz, DMSO-$d_6$) δ ppm 12.09 (br. s, 1H) 10.78 (br. s, 1H) 8.76 (d, J=2.78 Hz, 1H) 8.04-8.13 (m, 1H) 7.90-8.01 (m, 3H) 7.41 (d, J=8.59 Hz, 2H) 3.90 (s, 2H) 2.29 (s, 2H) 1.82-2.08 (m, 8H) 1.36 (s, 9H)

EXAMPLE 2

2-(4-(4-(5-((5-cyclobutyl-1,3,4-oxadiazol-2-yl)amino)pyridin-2-yl)phenyl)-2-oxabicyclo[2.2.2]octan-1-yl)acetic acid Step 1. Synthesis of methyl 2-(4-(4-(5-(5-cyclobutyl-1,3,4-oxadiazol-2-ylamino)pyridin-2-yl)phenyl)-2-oxabicyclo[2.2.2]octan-1-yl)acetate

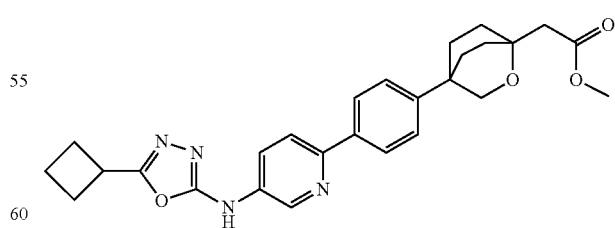

The title compound was prepared analogous to Example 1, Step 9 starting from methyl2-(4-(4-(5-aminopyridin-2-yl)phenyl)-2-oxabicyclo[2.2.2]octan-1-yl)acetate (35 mg, 0.10 mmol) and cyclobutylcarbohydrazide (17 mg, 0.15 mmol). Column purification afforded the title compound as white solid after drying (38 mg, 81% yield). LC/MS, ESI-MS(+): 475.25, RT: 1.14 (Condition E).

Step 2. Synthesis of 2-(4-(4-(5-((5-cyclobutyl-1,3,4-oxadiazol-2-yl)amino)pyridin-2-yl)phenyl)-2-oxabicyclo[2.2.2]octan-1-yl)acetic acid

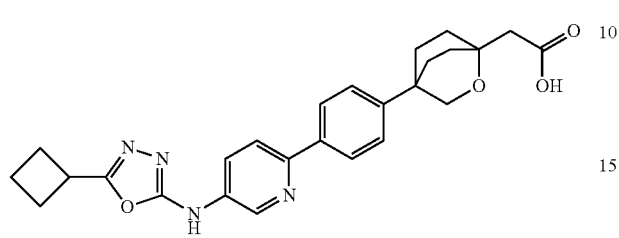

To a mixture of methyl 2-(4-(4-(5-(5-cyclobutyl-1,3,4-oxadiazol-2-ylamino)pyridin-2-yl)phenyl)-2-oxabicyclo[2.2.2]octan-1-yl)acetate (38 mg, 0.08 mmol) and THF (1 ml) was added NaOH (0.24 ml, 0.24 mmol). The mixture was stirred at room temperature for 7 hour. The resulting content was concentrated and purified on prep-HPLC to afford the title compound as white solid after drying (15 mg, 41% yield). HR/MS (M+H)$^+$ found 461.2188. calc. 461.2184. RT: 5.63 (Condition Z). $^1$H NMR (400 MHz, DMSO-$d_6$) δ ppm 1.85-2.13 (m, 10H) 2.27-2.40 (m, 6H) 3.69 (quind, J=8.43, 8.43, 8.43, 8.43, 0.88 Hz, 1H) 3.91 (s, 2H) 7.41 (d, J=8.59 Hz, 2H) 7.90-8.01 (m, 3H) 8.10 (dd, J=8.59, 2.78 Hz, 1H) 8.75 (d, J=3.03 Hz, 1H)

EXAMPLE 3

2-(4-(4-(5-((5-cyclobutyl-1,3,4-thiadiazol-2-yl)amino)pyridin-2-yl)phenyl)-2-oxabicyclo[2.2.2]octan-1-yl)acetic acid Step 1. Synthesis of ethyl/methyl 2-(4-(4-(5-(5-cyclobutyl-1,3,4-thiadiazol-2-ylamino)pyridin-2-yl)phenyl)-2-oxabicyclo[2.2.2]octan-1-yl)acetate

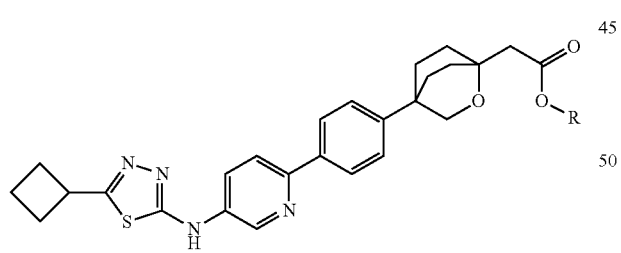

R = Me, Et

To a solution of methyl2-(4-(4-(5-aminopyridin-2-yl)phenyl)-2-oxabicyclo[2.2.2]octan-1-yl)acetate (57 mg, 0.16 mmol) in DCM (0.5 ml) was added 1,1'-thiocarbonyldipyridin-2(1H)-one (39 mg, 0.17 mmol) and the mixture was stirred at room temperature. After 30 minutes of stirring, cyclobutylcarbohydrazide (28 mg, 0.24 mmol) was added and the reaction was stirred at room temperature for 2 hour. Afterward, a solution of concentrated H$_2$SO$_4$ (0.05 ml, 0.94 mmol) was added and the mixture stirred at room temperature for 3 hour. The mixture was taken up in EtOAc and washed with NaHCO$_3$, then brine. The organic portion was dried over sodium MgSO$_4$, filtered and concentrated to afford a crude product. Column purification afforded the title compound containing approximately 25% of ethyl ester (total yield 33 mg,). The mixture was used in the next step without additional purification. LC/MS, ESI-MS(+): Methyl ester, 491.7, RT: 1.20 (Condition E). Ethyl ester, 505.6, RT: 1.26 (Condition E).

Step 2. Synthesis of 2-(4-(4-(5-((5-cyclobutyl-1,3,4-thiadiazol-2-yl)amino)pyridin-2-yl)phenyl)-2-oxabicyclo[2.2.2]octan-1-yl)acetic acid

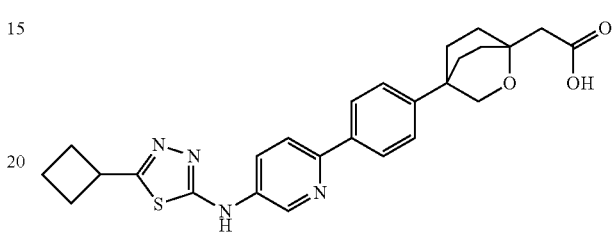

The title compound was prepared analogous to Example 2, Step 2 starting from ethyl/methyl 2-(4-(4-(5-(5-cyclobutyl-1,3,4-thiadiazol-2-ylamino)pyridin-2-yl)phenyl)-2-oxabicyclo[2.2.2]octan-1-yl)acetate (33 mg, 0.07 mmol) and 1N NaOH (0.20 ml, 0.20 mmol) solution. Prep-HPLC purification afforded the title compound as white solid after drying (18 mg, 56% yield). HR/MS (M+H)$^+$ found 477.1961. calc. 477.1955. RT: 5.93 (Condition Z).). $^1$H NMR (400 MHz, DMSO-$d_6$) δ ppm 1.85-2.08 (m, 10H) 2.30 (s, 4H) 2.35-2.44 (m, 2H) 3.84 (quind, J=8.49, 8.49, 8.49, 8.49, 0.88 Hz, 1H) 3.90 (s, 2H) 7.41 (d, J=8.59 Hz, 2H) 7.93 (d, J=8.59 Hz, 1H) 7.97 (d, J=8.59 Hz, 2H) 8.25 (dd, J=8.72, 2.65 Hz, 1H) 8.77 (d, J=2.78 Hz, 1H)

EXAMPLE 4

2-(4-(4-(2-(5-cyclobutyl-1,3,4-thiadiazol-2-ylamino)pyrimidin-5-yl)phenyl)-2-oxabicyclo[2.2.2]octan-1-yl)acetic acid Step 1. Synthesis of methyl 2-(4-(4-(2-aminopyrimidin-5-yl)phenyl)-2-oxabicyclo[2.2.2]octan-1-yl)acetate

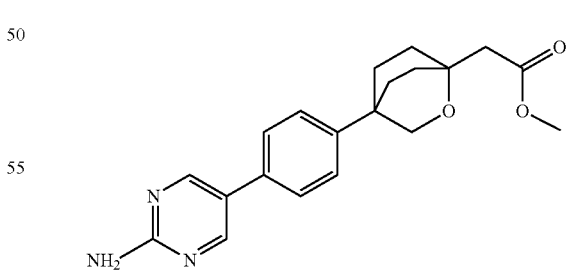

To a reaction vial containing methyl 2-(4-(4-(4,4,5,5-tetramethyl-1,3,2-dioxaborolan-2-yl)phenyl)-2-oxabicyclo[2.2.2]octan-1-yl)acetate (200 mg, 0.52 mmol), 5-bromopyrimidin-2-amine (108 mg, 0.62 mmol) and K$_3$PO$_4$ (132 mg, 0.62 mmol) was added dimethoxyethane (4.8 ml). The mixture was stirred at room temperature and degassed after the addition of EtOH (1.6 ml) and water (0.64 ml). PdCl$_2$(dppf)

DCM adduct (21 mg, 0.03 mmol) was added and the mixture was heated to 8° C. in an oil bath for 3 hours. The reaction mixture was then concentrated to dryness and taken up in DCM. The slurry was dried over sodium sulfate and filtered through a pad of celite. The filtrate was concentrated and purified by column chromatography to afford the title compound (193 mg, 84% yield). LC/MS, ESI-MS(+): 354.3, RT: 1.06 (Condition E).

Step 2. Synthesis of methyl 2-(4-(4-(2-(2-cyclobutanecarbonyl)hydrazinecarbothioamido)pyrimidin-5-yl)phenyl)-2-oxabicyclo[2.2.2]octan-1-yl)acetate

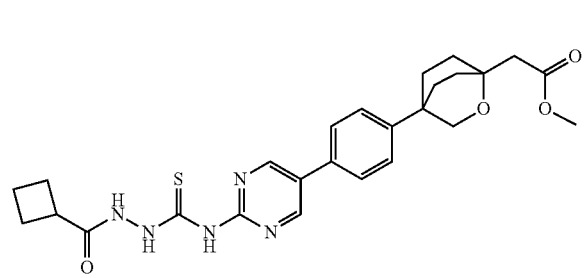 [SMILES: COC(=O)CC12CCC(c3ccc(-c4cnc(NC(=S)NNC(=O)C5CCC5)nc4)cc3)(CC1)CO2]

To a reaction vial containing methyl 2-(4-(4-(2-aminopyrimidin-5-yl)phenyl)-2-oxabicyclo[2.2.2]octan-1-yl)acetate (40 mg, 0.11 mmol) was added dichloromethane (1 ml) at room temperature. 1,1'-thiocarbonyldipyridin-2(1H)-one (29 mg, 0.12 mmol) was added and the resulting mixture was heated to 50° C. for overnight. The mixture was cool down to room temperature and cyclobutanecarbohydrazide (19 mg, 0.17 mmol) was then added and stirred at room temperature for another hour. The content was then concentrated to dryness and the resulting residue was taken up in MeOH to form a nice slurry. The slurry was filtered and washed with small amount of MeOH to afford the title compound as off-white solid after drying (48 mg, 83% yield). LC/MS, ESI-MS(+): 510.4, RT: 1.26 (Condition E)

Step 3. Synthesis of ethyl/methyl 2-(4-(4-(2-(5-cyclobutyl-1,3,4-thiadiazol-2-ylamino)pyrimidin-5-yl)phenyl)-2-oxabicyclo[2.2.2]octan-1-yl)acetate

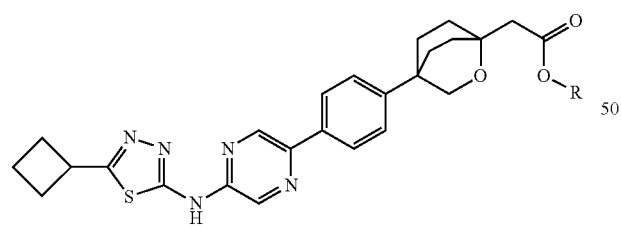

R = Me, Et

To a reaction vial containing methyl 2-(4-(4-(2-(2-cyclobutanecarbonyl) hydrazinecarbothioamido)pyrimidin-5-yl)phenyl)-2-oxabicyclo[2.2.2]octan-1-yl)acetate (49 mg, 0.10 mmol) was added EtOH (0.6 ml) at room temperature. A solution of concentrated $H_2SO_4$ (0.03 ml, 0.56 mmol) was added and the mixture heated to 8° C. for 1 hour. The resulting mixture was cooled to room temperature and quenched with a solution of saturated $NaHCO_3$ dropwise. The content was concentrated to dryness and subsequently taken up in DCM and dried over sodium sulfate. The mixture was filtered and concentrated to afford a crude residue. Column purification afforded the title compound containing approximately 18% of methyl ester (total yield 41 mg,). The mixture was used in the next step without additional purification. LC/MS, ESI-MS(+): Methyl ester, 492.2, RT: 1.42 (Condition E). Ethyl ester, 506.2, RT: 1.50 (Condition E).

Step 4. Synthesis of 2-(4-(4-(2-(5-cyclobutyl-1,3,4-thiadiazol-2-ylamino)pyrimidin-5-yl)phenyl)-2-oxabicyclo[2.2.2]octan-1-yl)acetic acid

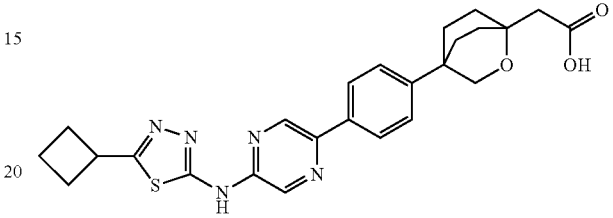

To a reaction vial containing a mixture of ethyl/methyl 2-(4-(4-(2-(5-cyclobutyl-1,3,4-thiadiazol-2-ylamino)pyrimidin-5-yl)phenyl)-2-oxabicyclo[2.2.2]octan-1-yl)acetate (41 mg, 0.08 mmol) was added THF (1 ml) and MeOH (1 ml) at room temperature. NaOH (0.24 ml, 0.24 mmol) was added and the mixture stirred at room temperature for overnight. The reaction mixture was then concentrated to dryness and taken up in water. The mixture was acidified with 1N HCl to a pH of between 3 and 4 affording thick slurry. The slurry is filtered and washed with small amount of water to afford the title compound as white solid after drying (37 mg, 97% yield). HR/MS (M+H)$^+$ found 478.1901. calc. 478.1913. RT: 2.68 (Condition L). $^1$H NMR (400 MHz, DMSO-d$_6$) δ ppm 12.16 (br. s, 2H) 8.95 (s, 2H) 7.69 (d, J=8.59 Hz, 2H) 7.44 (d, J=8.59 Hz, 2H) 3.90 (s, 3H) 2.37-2.47 (m, 2H) 2.24-2.36 (m, 4H) 1.82-2.12 (m, 10H).

EXAMPLE 5

2-(4-(4-(6-((5-cyclobutyl-1,3,4-thiadiazol-2-yl) amino)pyridin-3-yl)phenyl)-2-oxabicyclo[2.2.2]octan-1-yl)acetic acid Step 1. Synthesis of methyl 2-(4-(4-(6-aminopyridin-3-yl)phenyl)-2-oxabicyclo[2.2.2]octan-1-yl)acetate

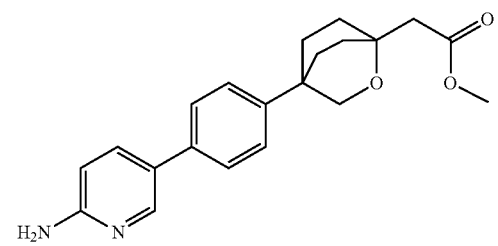 [SMILES: COC(=O)CC12CCC(c3ccc(-c4ccc(N)nc4)cc3)(CC1)CO2]

The title compound was prepared analogous to Example 4, Step 1 starting from methyl 2-(4-(4-(4,4,5,5-tetramethyl-1,3,2-dioxaborolan-2-yl)phenyl)-2-oxabicyclo[2.2.2]octan-1-yl)acetate (200 mg, 0.52 mmol) and 5-iodopyridin-2-amine (137 mg, 0.62 mmol). The reaction was performed at 80° C. for overnight. After workup and column purification afforded the title compound as off-white solid after drying (133 mg, 58% yield). LC/MS, ESI-MS(+):353.3, RT: 1.12 (Condition E).

Step 2. Synthesis of ethyl/methyl 2-(4-(4-(6-(5-cyclobutyl-1,3,4-thiadiazol-2-ylamino)pyridin-3-yl)phenyl)-2-oxabicyclo[2.2.2]octan-1-yl)acetate

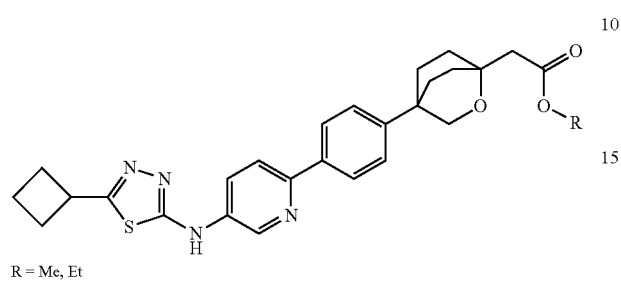

R = Me, Et

To a reaction vial containing methyl 2-(4-(4-(6-aminopyridin-3-yl)phenyl)-2-oxabicyclo[2.2.2]octan-1-yl)acetate (40 mg, 0.11 mmol) and DCM (1 ml) was added 1,1'-thiocarbonyldipyridin-2(1H)-one (29 mg, 0.12 mmol). The mixture was stirred at room temperature for 1 hour. Cyclobutanecarbohydrazine (19 mg, 0.17 mmol) was then added and the reaction stirred at room temperature for another hour. The mixture was then concentrated to dryness, EtOH (1 ml), followed by a solution of concentrated $H_2SO_4$ (0.04 ml, 0.66 mmol) was added. The mixture was heated to 80° C. for 1 hour. The resulting mixture was cooled to room temperature and quenched with a solution of saturated $NaHCO_3$ dropwise. The content was concentrated to dryness and subsequently taken up in DCM and dried over sodium sulfate. The mixture was filtered and concentrated to afford a crude residue. Column purification afforded the title compound containing approximately 47% of methyl ester (total yield 48 mg,). The mixture was used in the next step without additional purification. LC/MS, ESI-MS(+): Methyl ester, 491.2, RT: 2.88 (Condition M). Ethyl ester, 505.2, RT: 3.06 (Condition M).

Step 3. Synthesis of 2-(4-(4-(6-((5-cyclobutyl-1,3,4-thiadiazol-2-yl)amino)pyridin-3-yl)phenyl)-2-oxabicyclo[2.2.2]octan-1-yl)acetic acid

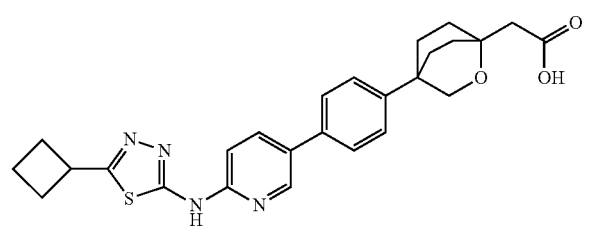 [SMILES: O=C(O)CC12CCC(c3ccc(-c4ccc(Nc5nnc(C6CCC6)s5)nc4)cc3)(CC1)CO2]

To a reaction vial containing a mixture of ethyl/methyl 2-(4-(4-(6-(5-cyclobutyl-1,3,4-thiadiazol-2-ylamino)pyridin-3-yl)phenyl)-2-oxabicyclo[2.2.2]octan-1-yl)acetate (48 mg, 0.10 mmol) was added THF (0.5 ml) and MeOH (0.5 ml) at room temperature. 1N NaOH (0.29 ml, 0.29 mmol) was added and the mixture was stirred at RT for overnight. The mixture was concentrated to dryness and taken in water to form a slurry. HCl was added adjusting the pH to 3 and 4. The resulting slurry was filtered, washed with water to afford the title compound as white solid after drying (36.8 mg, 79% yield). HR/MS (M+H)+ found 477.1949. calc. 477.1960. RT: 2.83 (Condition L). $^1$H NMR (400 MHz, DMSO-$d_6$) δ ppm 10.95-12.82 (m, 2H) 8.58 (d, J=2.27 Hz, 1H) 7.91-8.14 (m, 1H) 7.62 (d, J=8.34 Hz, 2H) 7.41 (d, J=8.59 Hz, 2H) 7.14 (d, J=8.59 Hz, 1H) 3.79-3.95 (m, 3H) 2.24-2.47 (m, 6H) 1.82-2.13 (m, 10H).

EXAMPLE 6

2-(4-(4'-(5-cyclobutyl-1,3,4-thiadiazol-2-ylamino)biphenyl-4-yl)-2-oxabicyclo[2.2.2]octan-1-yl)acetic acid Step 1. Synthesis of methyl 2-(4-(4'-nitrobiphenyl-4-yl)-2-oxabicyclo[2.2.2]octan-1-yl)acetate

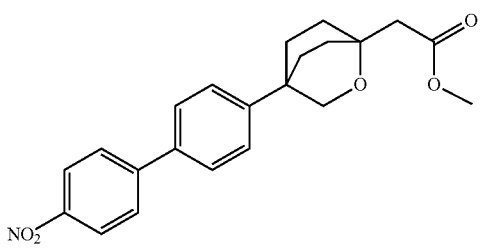 [SMILES: COC(=O)CC12CCC(c3ccc(-c4ccc([N+](=O)[O-])cc4)cc3)(CC1)CO2]

To a round bottom flask containing methyl 2-(4-(4-(4,4,5,5-tetramethyl-1,3,2-dioxaborolan-2-yl)phenyl)-2-oxabicyclo[2.2.2]octan-1-yl)acetate (800 m g, 2.07 mmol), 1-iodo-4-nitrobenzene (619 mg, 2.49 mmol) and $K_3PO_4$ (528 mg, 2.49 mmol) was added dimethoxyethane (24 ml) at room temperature. The mixture was stirred at room temperature and degassed after the addition of EtOH (8 ml) and water (3.2 ml). $PdCl_2$(dppf) dichloromethane adduct (85 mg, 0.10 mmol) was added and the mixture was heated to 8° C. in an oil bath for overnight. The reaction mixture was then concentrated to dryness and taken up in DCM. The slurry was dried over sodium sulfate and filtered through a pad of celite. The filtrate was concentrated and purified by column chromatography affording the title compound as off-white solid (624 mg, 79% yield). LC/MS, ESI-MS(+): 382.4, RT: 1.49 (Condition E).

Step 2. Synthesis of methyl 2-(4-(4'-aminobiphenyl-4-yl)-2-oxabicyclo[2.2.2]octan-1-yl)acetate

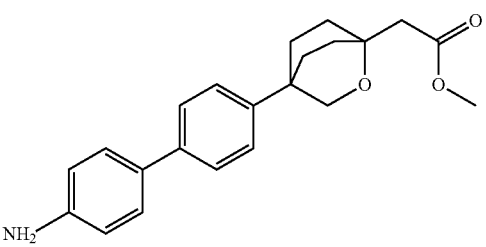 [SMILES: COC(=O)CC12CCC(c3ccc(-c4ccc(N)cc4)cc3)(CC1)CO2]

To a round bottom flask containing methyl 2-(4-(4'-nitrobiphenyl-4-yl)-2-oxabicyclo[2.2.2]octan-1-yl)acetate (716 mg, 1.88 mmol) was added Pd(OH)$_2$ on activated carbon (395 mg, 2.82 mmol). EtOAc (15 ml) and MeOH (3 ml) were added and the mixture was stirred under 1 atm. of hydrogen at room temperature for 2 hours. The resulting mixture was filtered through a pad of celite and concentrated to afford a crude residue. Column purification affords the title compound as off-white solid after drying (595 mg, 90% yield). LC/MS, ESI-MS(+): 352.3, RT: 1.29 (Condition E).

Step 3. Synthesis of methyl 2-(4-(4'-(2-(cyclobutanecarbonyl) hydrazinecarbothioamido) biphenyl-4-yl)-2-oxabicyclo[2.2.2]octan-1-yl)acetate

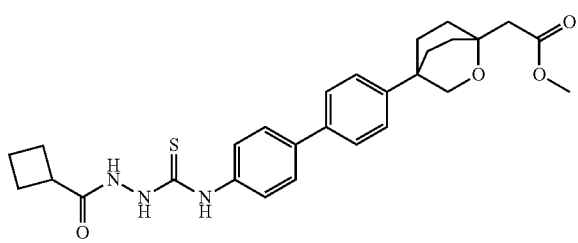 [SMILES: COC(=O)CC12CCC(c3ccc(-c4ccc(NC(=S)NNC(=O)C5CCC5)cc4)cc3)(CC1)CO2]

The title compound was prepared analogous to Example 4, Step 2, starting from methyl 2-(4-(4'-aminobiphenyl-4-yl)-2-oxabicyclo[2.2.2]octan-1-yl)acetate (500 mg, 1.48 mmol) with 1,1'-thiocarbonyldipyridin-2(1H)-one (379 mg, 1.63 mmol) and cyclobutanecarbohydrazide (254 mg, 2.22 mmol). Water titration of the crude residue affords the title compound as off-white solid after drying (696 mg, 93% yield). LC/MS, ESI-MS(+): 508.4, RT: 1.29 (Condition E).

Step 4. Synthesis of ethyl/methyl 2-(4-(4'-(5-cyclobutyl-1,3,4-thiadiazol-2-ylamino)biphenyl-4-yl)-2-oxabicyclo[2.2.2]octan-1-yl)acetate

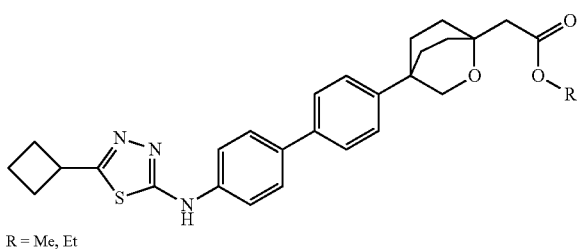

R = Me, Et

The title compound was prepared analogous to Example 4, Step 3 starting from methyl 2-(4-(4'-(2-(cyclobutanecarbonyl)hydrazinecarbothioamido) biphenyl-4-yl)-2-oxabicyclo[2.2.2]octan-1-yl)acetate (300 mg, 0.59 mmol) with concentrated $H_2SO_4$ (0.19 ml, 3.43 mmol) in EtOH. Column purification affords the title compound containing approximately 24% of methyl ester (total yield 235 mg,). The mixture was used in the next step without additional purification.

LC/MS, ESI-MS(+): Methyl ester, 490.4, RT: 1.47 (Condition E). Ethyl ester, 504.4, RT: 1.52 (Condition E).

Step 5. Synthesis of 2-(4-(4'-(5-cyclobutyl-1,3,4-thiadiazol-2-ylamino)biphenyl-4-yl)-2-oxabicyclo[2.2.2]octan-1-yl)acetic acid

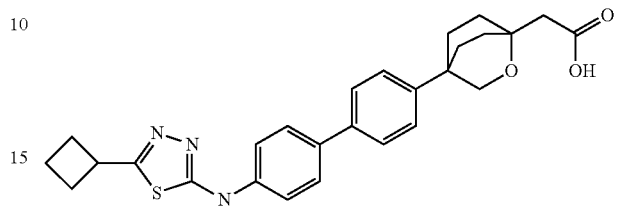

To a reaction vial containing a mixture of ethyl/methyl 2-(4-(4'-(5-cyclobutyl-1,3,4-thiadiazol-2-ylamino)biphenyl-4-yl)-2-oxabicyclo[2.2.2]octan-1-yl)acetate (235 mg, 0.47 mmol) was added THF (2 ml) and MeOH (2 ml) at room temperature. 1N NaOH (1.4 ml, 1.4 mmol) was added and the mixture was stirred at RT for overnight. The mixture was concentrated to dryness and taken in water to form a nice slurry. The slurry was then filtered and washed with water to afford the title compound as sodium salt. To a round bottom flask containing the sodium salt was added a mixture of 1:1 acetonitrile and water (total volume 10 ml) at room temperature. The mixture was acidified with 1N HCl to a pH of between 3 and 4 affording a thick slurry. The mixture was then concentrated to remove excess acetonitrile and filtered. The filter cake was washed with water to afford the title compound as white solid after drying (178 mg, 80% yield). HR/MS (M+H)$^+$ found 476.2014. calc. 476.2008. RT: 2.89 (Condition L). $^1$H NMR (400 MHz, DMSO-$d_6$) δ ppm 10.48 (br. s, 1H) 7.68 (d, J=8.84 Hz, 2H) 7.62 (d, J=8.84 Hz, 2H) 7.57 (d, J=8.59 Hz, 2H) 7.37 (d, J=8.34 Hz, 2H) 3.87 (s, 2H) 3.79-3.85 (m, 1H) 2.20-2.45 (m, 4H) 1.76-2.19 (m, 12H)

EXAMPLE 7

2-(4-(4'-(5-cyclobutyl-1,3,4-oxadiazol-2-ylamino) biphenyl-4-yl)-2-oxabicyclo[2.2.2]octan-1-yl)acetic acid Step 1. Synthesis of methyl 2-(4-(4'-(5-cyclobutyl-1,3,4-oxadiazol-2-ylamino)biphenyl-4-yl)-2-oxabicyclo[2.2.2]octan-1-yl)acetate

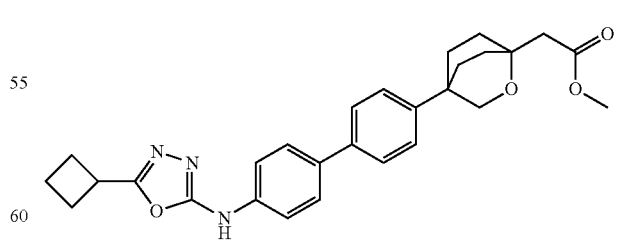

To a reaction vial containing methyl 2-(4-(4'-(2-(cyclobutanecarbonyl)hydrazinecarbothioamido) biphenyl-4-yl)-2-oxabicyclo[2.2.2]octan-1-yl)acetate (300 mg, 0.59 mmol) was added DCM (6 ml) at room temperature. 1-ethyl-3-(3-dimethylaminopropyl)carbodiimide (204 mg, 1.06 mmol)

was added and the mixture was stirred at room temperature for overnight. The reaction mixture was purified directly via column chromatography affording the title compound as off-white solid after drying (252 mg, 90% yield). LC/MS, ESI-MS(+): 474.4, RT: 1.40 (Condition E).

Step 2. Synthesis of 2-(4-(4'-(5-cyclobutyl-1,3,4-oxadiazol-2-ylamino)biphenyl-4-yl)-2-oxabicyclo[2.2.2]octan-1-yl)acetic acid

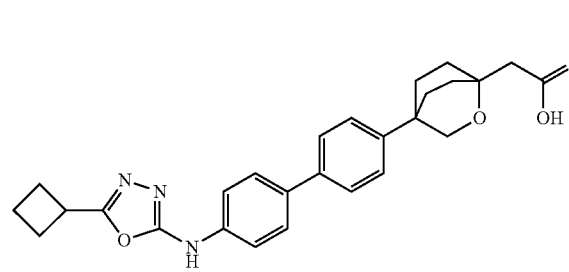

The title compound was prepared analogous to Example 4, Step 4, starting from methyl 2-(4-(4'-(5-cyclobutyl-1,3,4-oxadiazol-2-ylamino)biphenyl-4-yl)-2-oxabicyclo[2.2.2]octan-1-yl)acetate (252 mg, 0.53 mmol) and NaOH (1.60 ml, 1.60 mmol). After acidification with 1N HCl, the slurry was filtered and washed with water to afford the title compound as white solid after drying (226 mg, 92% yield). HR/MS (M+H)+ found 460.2221. calc. 476.2236. RT: 2.68 (Condition L). $^1$H NMR (400 MHz, DMSO-$d_6$) δ ppm 10.53 (s, 1H) 7.62 (s, 4H) 7.57 (d, J=8.59 Hz, 2H) 7.38 (d, J=8.59 Hz, 2H) 3.89 (s, 2H) 3.62-3.73 (m, 1H) 2.22-2.41 (m, 6H) 1.82-2.11 (m, 10H)

EXAMPLE 8

2-(4-(4'-(5-tert-butyl-1,3,4-oxadiazol-2-ylamino)biphenyl-4-yl)-2-oxabicyclo[2.2.2]octan-1-yl)acetic acid Step 1. Synthesis of methyl 2-(4-(4'-(5-tert-butyl-1,3,4-oxadiazol-2-ylamino)biphenyl-4-yl)-2-oxabicyclo[2.2.2]octan-1-yl)acetate

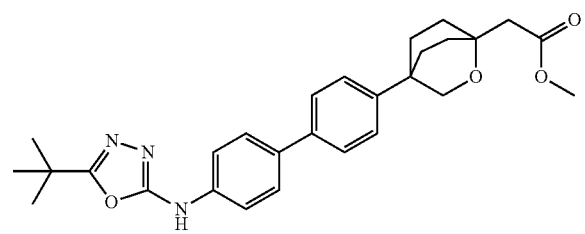 [SMILES: COC(=O)CC12CCC(c3ccc(-c4ccc(Nc5nnc(C(C)(C)C)o5)cc4)cc3)(CC1)CO2]

The title compound was prepared analogous to Example 1, Step 9 starting from methyl 2-(4-(4'-aminobiphenyl-4-yl)-2-oxabicyclo[2.2.2]octan-1-yl)acetate (95 mg, 0.28 mmol). The crude residue was triturated in MeOH and filtered to afford the title compound as off-white solid after drying (117 mg, 87% yield). LC/MS, ESI-MS(+): 476.4, RT: 1.42 (Condition E).

Step 2. Synthesis of 2-(4-(4'-(5-tert-butyl-1,3,4-oxadiazol-2-ylamino)biphenyl-4-yl)-2-oxabicyclo[2.2.2]octan-1-yl)acetic acid

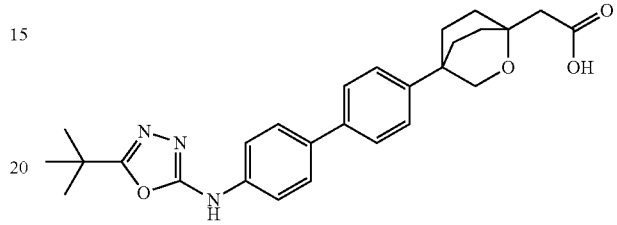

The title compound was prepared analogous to Example 4, Step 4 starting from methyl 2-(4-(4'-(5-tert-butyl-1,3,4-oxadiazol-2-ylamino)biphenyl-4-yl)-2-oxabicyclo[2.2.2]octan-1-yl)acetate (82 mg, 0.17 mmol) and NaOH (0.52 ml, 0.52 mmol). After acidification with 1N HCl, the slurry was filtered and washed with water to afford the title compound as white solid after drying (75 mg, 95% yield). HR/MS (M+H)+ found 462.2396. calc. 462.2392. RT: 2.75 (Condition L). $^1$H NMR (400 MHz, DMSO-$d_6$) δ ppm 12.07 (s, 1H) 10.51 (s, 1H) 7.62 (s, 4H) 7.58 (d, J=8.34 Hz, 2H) 7.38 (d, J=8.59 Hz, 2H) 3.90 (s, 2H) 2.33 (s, 2H) 1.82-2.07 (m, 8H) 1.36 (s, 9H)

EXAMPLE 9

2-(4-(4'-((5-cyclopropyl-1,3,4-oxadiazol-2-yl)amino)-[1,1'-biphenyl]-4-yl)-2-oxabicyclo[2.2.2]octan-1-yl)acetic acid Step 1. Synthesis of methyl 2-(4-(4'-((5-cyclopropyl-1,3,4-oxadiazol-2-yl)amino)-[1,1'-biphenyl]-4-yl)-2-oxabicyclo[2.2.2]octan-1-yl)acetate

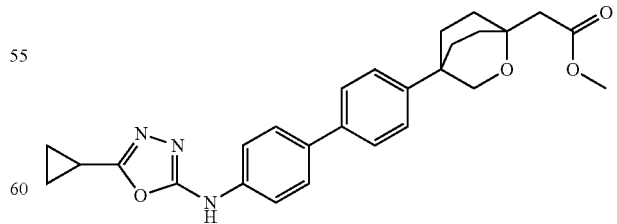

The title compound was prepared analogous to Example 1, Step 9 starting from methyl 2-(4-(4'-aminobiphenyl-4-yl)-2-oxabicyclo[2.2.2]octan-1-yl)acetate (335 mg, 0.95 mmol). The crude residue was purified by column chromatography to afford the title compound as off-white solid after drying (117 mg, 87% yield). LC/MS, ESI-MS(+): 460.2, RT: 1.34 (Condition W).

Step 2. Synthesis of 2-(4-(4'-((5-cyclopropyl-1,3,4-oxadiazol-2-yl)amino)-[1,1'-biphenyl]-4-yl)-2-oxabicyclo[2.2.2]octan-1-yl)acetic acid sodium salt

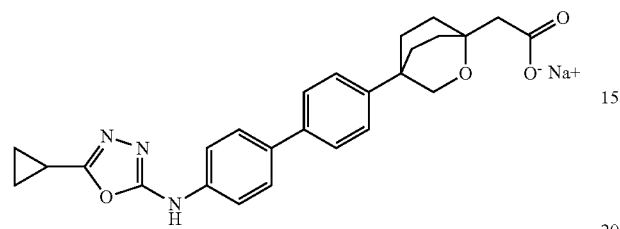

The title compound was prepared analogous to Example 4, Step 5 starting from methyl 2-(4-(4'-((5-cyclopropyl-1,3,4-oxadiazol-2-yl)amino)-[1,1'-biphenyl]-4-yl)-2-oxabicyclo[2.2.2]octan-1-yl)acetate (413 mg, 0.90 mmol) and NaOH (2.70 ml, 2.70 mmol). After completion of the reaction, the mixture was concentrated to dryness and taken up in water. The resulting slurry was filtered and washed with water to afford the title compound as white solid after drying (392 mg, 93% yield). HR/MS (M+H)+ found 446.2077. calc. 446.2080. RT: 1.54 (Condition L). $^1$H NMR (400 MHz, DMSO-$d_6$) δ ppm 10.54 (br. s., 1H) 7.58-7.64 (m, 4H) 7.55 (d, J=8.34 Hz, 2H) 7.36 (d, J=8.34 Hz, 2H) 3.84 (s, 2H) 2.16-2.27 (m, 2H) 2.13 (tt, J=8.37, 5.02 Hz, 1H) 2.00 (s, 2H) 1.88-1.99 (m, 2H) 1.69-1.88 (m, 4H) 1.03-1.10 (m, 2H) 0.91-0.98 (m, 2H)

Step 3. Synthesis of 2-(4-(4'-((5-cyclopropyl-1,3,4-oxadiazol-2-yl)amino)-[1,1'-biphenyl]-4-yl)-2-oxabicyclo[2.2.2]octan-1-yl)acetic acid

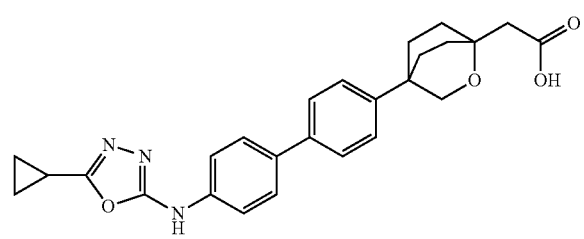 [SMILES: O=C(O)CC12CCC(c3ccc(-c4ccc(Nc5nnc(C6CC6)o5)cc4)cc3)(CC1)CO2]

To a reaction vial contaminions 2-(4-(4'-((5-cyclopropyl-1,3,4-oxadiazol-2-yl)amino)-[1,1'-biphenyl]-4-yl)-2-oxabicyclo[2.2.2]octan-1-yl)acetic acid sodium salt (195 mg, 0.42 mmol) was added water (5 ml). The mixture was stirred and hydrochloric acid was added dropwise until the entire mixture achieved a pH between 3 and 4. The resulting slurry was filtered, washed with water to afford the title compound as white solid after drying (183 mg, 99% yield). HR/MS (M+H)+ found 446.2070. calc. 446.2080. RT: 1.66 (Condition L). $^1$H NMR (400 MHz, DMSO-$d_6$) δ ppm 12.01 (br. s, 1H) 10.43 (s, 1H) 7.52-7.67 (m, 6H) 7.38 (d, J=8.59 Hz, 2H) 3.89 (s, 2H) 2.32 (s, 2H) 2.08-2.19 (m, 1H) 1.79-2.07 (m, 8H) 1.02-1.12 (m, 2H) 0.91-0.99 (m, 2H).

EXAMPLE 10

2-(4-(4'-(2-methyl-5-(trifluoromethyl)oxazole-4-carboxamido)-[1,1'-biphenyl]-4-yl)-2-oxabicyclo[2.2.2]octan-1-yl)acetic acid Step 1. Synthesis of 2-methyl-N-(4-(4,4,5,5-tetramethyl-1,3,2-dioxaborolan-2-yl)phenyl)-5-(trifluoromethyl)oxazole-4-carboxamide

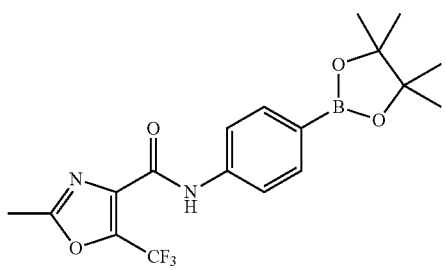

To a stirred solution of 4-(4,4,5,5-tetramethyl-1,3,2-dioxaborolan-2-yl) aniline (420 mg, 1.917 mmol) in anhydrous DMF (9.6 mL) was added 2-methyl-5-(trifluoromethyl)oxazole-4-carboxylic acid (449 mg, 2.300 mmol) followed by DIPEA (1.0 mL, 5.75 mmol) and the mixture was stirred at room temperature for 10 minutes. HATU (875 mg, 2.300 mmol) was added and the mixture stirred at room temperature for 16 hours. The mixture was taken up in 1:1 mixture of brine and water and extracted with EtOAc. The organic portion was dried over sodium sulfate, filtered and concentrated to afford a brown oil, which was purified by flash column chromatography to afford the title compound as pale yellow solid after drying (360 mg, 47% yield). LC/MS, ESI-MS(+): 397.1, RT: 1.49 (Condition E).

Step 2. Synthesis of methyl 2-(4-(4'-(2-methyl-5-(trifluoromethyl)oxazole-4-carboxamido)-[1,1'-biphenyl]-4-yl)-2-oxabicyclo[2.2.2]octan-1-yl)acetate

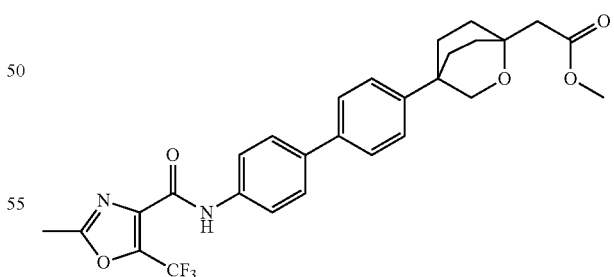

To a mixture of 2-methyl-N-(4-(4,4,5,5-tetramethyl-1,3,2-dioxaborolan-2-yl)phenyl)-5-(trifluoromethyl)oxazole-4-carboxamide (300 mg, 0.757 mmol) and methyl 2-(4-(4-bromophenyl)-2-oxabicyclo[2.2.2]octan-1-yl)acetate (257 mg, 0.757 mmol) in dioxane (3 ml) was added H$_2$O (0.33 ml) at room temperature. CsF (345 mg, 2.272 mmol) and Pd(amphos)Cl$_2$ (53.6 mg, 0.076 mmol) were added and the mixture was degassed several times before being heated to 90° C. for overnight. The reaction mixture was cooled to room temperature and directly purified by column chromatography to afford the title compound as white solid after drying (200 mg, 50% yield). LC/MS, ESI-MS(+): 529.0, RT: 1.52 (Condition E).

Step 3. Synthesis of 2-(4-(4-(5-(2-methyl-5-(trifluoromethyl)oxazole-4-carboxamido)pyridin-2-yl)phenyl)-2-oxabicyclo[2.2.2]octan-1-yl)acetic acid

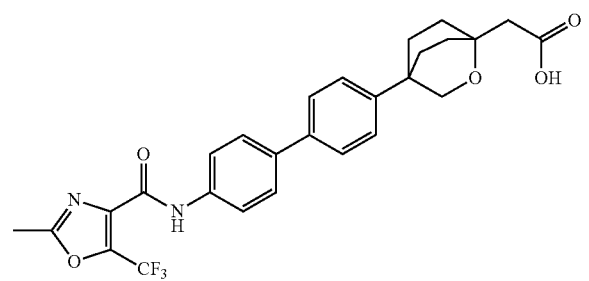

To a solution of methyl 2-(4-(4'-(2-methyl-5-(trifluoromethyl)oxazole-4-carboxamido)biphenyl-4-yl)-2-oxabicyclo[2.2.2]octan-1-yl)acetate (200 mg, 0.378 mmol) in THF (4 ml) at room temperature was added 1N LiOH (0.454 ml, 0.454 mmol). The mixture was stirred at room temperature for overnight. Water (4 ml) was added and the mixture was quenched with 1N HCl (0.454 ml, 0.454 mmol). The resulting slurry was stirred for 15 minutes and filtered. The solid was triturated with hot EtOAc and filtered to afford the title compound as white solid after drying (116 mg, 60% yield). HR/MS (M+H)$^+$ found 515.1788. calc. 515.1782. RT: 2.96 (Condition L). $^1$H NMR (400 MHz, DMSO-d$_6$) δ ppm 12.08 (s, 1H), 10.66 (s, 1H), 7.88 (d, J=8.0 Hz, 2H), 7.62 (m, 4H), 7.39 (d, J=8.00 Hz, 2H), 3.95 (s, 2H), 2.65 (s, 3H), 2.33 (s, 3H), 2.01-1.81 (m, 8H).

EXAMPLE 11

2-(4-(4'-(2-Ethyl-4-methyloxazole-5-carboxamido)biphenyl-4-yl)-.2-oxabicyclo[2.2.2]octan-1-yl)acetic acid Step 1. Synthesis of 2-ethyl-4-methyl-N-(4-(4,4,5,5-tetramethyl-1,3,2-dioxaborolan-2-yl)phenyl)oxazole-5-carboxamide

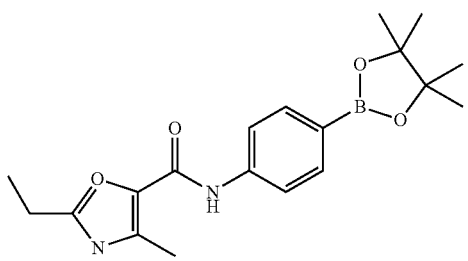

To a stirred solution of 4-(4,4,5,5-tetramethyl-1,3,2-dioxaborolan-2-yl) aniline (360 mg, 1.643 mmol) in anhydrous DMF (8.2 mL) was added 2-ethyl-4-methyloxazole-5-carboxylic acid (306 mg, 1.972 mmol), followed by DIPEA (0.86 mL, 4.93 mmol) and the mixture was stirred at room temperature for 10 minutes. HATU (750 mg, 1.972 mmol) was added and the mixture was stirred at room temperature for 16 hour. The mixture was taken up in 1:1 mixture of brine and water (40 mL) and extracted with EtOAc (60 mL). The organic portion was dried over sodium sulfate, filtered and concentrated to afford a brown oil, which was purified by flash column chromatography to afford the title compound (305 mg, 52% yield) as a white solid. LC/MS, ESI-MS (+): 357.1, RT: 1.35 (Condition E).

Step 2. Synthesis of methyl 2-(4-(4'-(2-ethyl-4-methyloxazole-5-carboxamido)-[1,1'-biphenyl]-4-yl)-2-oxabicyclo[2.2.2]octan-1-yl)acetate

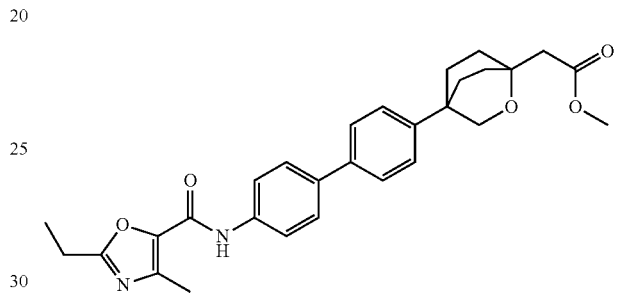

To a solution of 2-ethyl-4-methyl-N-(4-(4,4,5,5-tetramethyl-1,3,2-dioxaborolan-2-yl)phenyl)oxazole-5-carboxamide (200 mg, 0.561 mmol) and methyl 2-(4-(4-bromophenyl)-2-oxabicyclo[2.2.2]octan-1-yl)acetate (190 mg, 0.561 mmol) in dioxane (3 ml) was added H$_2$O (0.33 ml). CsF (256 mg, 1.684 mmol) and Pd(amphos)Cl$_2$ (39.8 mg, 0.056 mmol) were then added and the mixture was degassed before being heated at 90° C. for overnight. The reaction mixture was then cooled to room temperature and directly purified by column chromatography to afford the title compound as white solid after drying (159 mg, 58% yield). LC/MS, ESI-MS(+): 489.0, RT: 1.40 (Condition E).

Step 3. Synthesis of 2-(4-(4'-(2-ethyl-4-methyloxazole-5-carboxamido)-[1,1'-biphenyl]-4-yl)-2-oxabicyclo[2.2.2]octan-1-yl)acetic acid

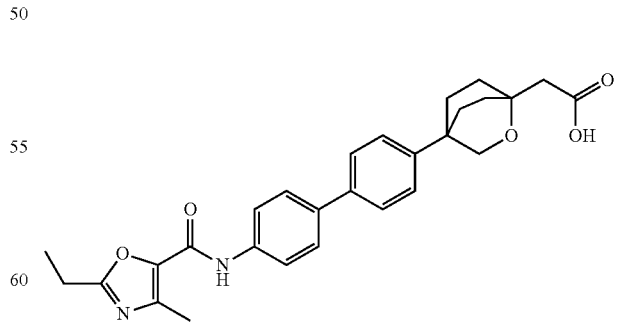

To a solution of 2-(4-(4'-(2-ethyl-4-methyloxazole-5-carboxamido)-[1,1'-biphenyl]-4-yl)-2-oxabicyclo[2.2.2]octan-1-yl)acetate (159 mg, 0.325 mmol) in THF (3 ml) at room temperature was added 1N LiOH (0.391 ml, 0.391 mmol).

The mixture was stirred at room temperature overnight. The mixture was quenched with 1N HCl (0.391 ml, 0.391 mmol) and diluted with H₂O. The THF was removed in vacuo to afford off-white slurry. The slurry was stirred for 15 min then filtered. The filter cake was washed with H₂O, heptane, and dried to afford the title compound as off-white sold (135 mg, 87% yield).

HR/MS (M+H)⁺ found 475.2222. calc. 475.2233. RT: 2.63 (Condition L). ¹H NMR (400 MHz, DMSO-d₆) δ ppm 12.08 (s, 1H), 10.18 (s, 1H), 7.82 (d, J=8.0 Hz, 2H), 7.62 (m, 4H), 7.39 (d, J=8.0 Hz, 2H), 3.90 (s, 2H), 2.85 (q, J=8.0 Hz, 2H), 2.49 (s, 3H), 2.33 (s, 2H), 2.06-1.85 (m, 8H), 1.33 (t, J=8.0 Hz, 3H).

EXAMPLE 12

2-(4-(4-(5-(2-methyl-5-(trifluoromethyl)oxazole-4-carboxamido)pyridin-2-yl)phenyl)-2-oxabicyclo[2.2.2]octan-1-yl)acetic acid

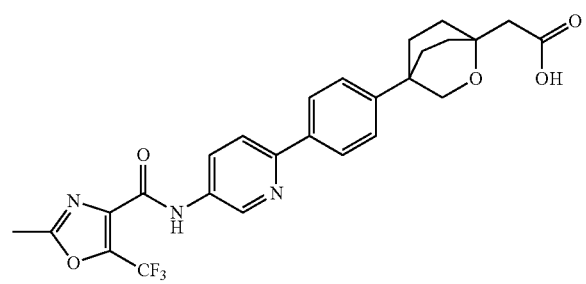 [SMILES: Cc1nc(C(=O)Nc2ccc(-c3ccc(C45CCC(CC(=O)O)(CC4)OC5)cc3)nc2)c(C(F)(F)F)o1]

To a solution of methyl 2-(4-(4-(5-aminopyridin-2-yl)phenyl)-2-oxabicyclo[2.2.2]octan-1-yl)acetate (212 mg, 0.602 mmol) in DMF (3 ml) at rt under N₂ was added 2-methyl-5-(trifluoromethyl)oxazole-4-carboxylic acid (141 mg, 0.722 mmol) and Et₃N (0.167 ml, 1.203 mmol. The mixture was stirred for 5 minutes before the addition of HATU (274 mg, 0.722 mmol) at room temperature. Upon completion of reaction, the mixture was diluted with H₂O (25 ml) and extracted with EtOAc (50 ml). The organic portion was washed with brine, dried over sodium sulfate, filtered and concentrated to afford the crude methyl ester. LC/MS, ESI-MS (+): 530.0, RT: 1.37 (Condition E). The crude methylester was suspended in THF (4 ml) and treated with 1N LiOH (0.722 ml, 0.722 mmol). Upon completion of reaction, the mixture was diluted with H₂O and brought to pH 5 with acetic acid. The resulting slurry was filtered, washed with H₂O and dried at 80° C. for several hours. The crude solid was triturated with hot EtOH, AcN, and Et₂O to give the title compound as off-white solid after drying (65 mg, 19% yield). HR/MS (M+H)⁺ found 516.1749. calc. 516.1735, RT: 2.76 (Condition L). ¹H NMR (400 MHz, DMSO-d₆) δ ppm 12.08 1 (s, 1H), 10.92 (s, 1H), 9.03 (s, 1H), 8.30 (d, J=8.0 Hz, 1H), 7.99 (d, J=16.0 Hz, 2H), 7.94 (d, J=16.0 Hz, 1H), 7.44 (d, J=8.00 Hz, 2H), 3.91 (s, 2H), 2.63 (s, 3H), 2.33 (s, 2H), 2.08-1.85 (m, 8H).

EXAMPLE 13

2-(4-(4-(5-(2-ethyl-4-methyloxazole-5-carboxamido)pyridin-2-yl)phenyl)-2-oxabicyclo[2.2.2]octan-1-yl)acetic acid

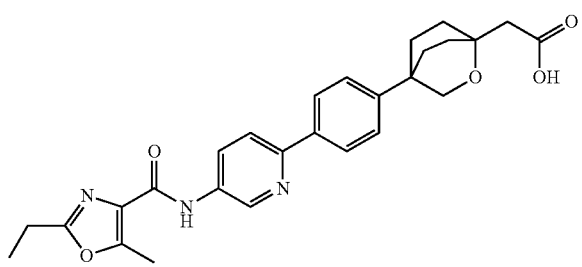 [SMILES: CCc1nc(C(=O)Nc2ccc(-c3ccc(C45CCC(CC(=O)O)(CC4)OC5)cc3)nc2)c(C)o1]

The title compound was prepared analogous to Example 12, starting from methyl 2-(4-(4-(5-aminopyridin-2-yl)phenyl)-2-oxabicyclo[2.2.2]octan-1-yl)acetate (114 mg, 0.32 mmol) and 2-ethyl-4-methyloxazole-5-carboxylic acid (60.2 mg, 0.39 mmol). The crude product was purified on prep-HPLC to afford the title compound as off-white solid after drying (28 mg, 17% yield). HR/MS (M+H)⁺ found 476.2166. calc. 476.2185, RT: 2.76 (Condition L). ¹H NMR (400 MHz, DMSO-d₆) δ ppm 10.55 (s, 1H), 8.98 (s, 1H), 8.24 (d, J=8.0 Hz, 1H), 8.01 (d, J=12.0 Hz, 2H), 7.95 (d, J=12.0 Hz, 1H), 7.43 (d, J=8.0 Hz, 2H), 3.91 (s, 2H), 2.86 (q, J=8.0 Hz, 2H), 2.36 (s, 2H), 2.25 (s, 2H), 2.09-1.90 (m, 8H), 1.36 (t, J=8.0 Hz, 3H).

EXAMPLE 14

2-(4-(4-(5-((5-(tert-butyl)oxazol-2-yl)amino)pyridin-2-yl)phenyl)-2-oxabicyclo[2.2.2]octan-1-yl)acetic acid Step 1. Synthesis of Benzyl 2-(4-(4-(5-aminopyridin-2-yl)phenyl)-2-oxabicyclo[2.2.2]octan-1-yl)acetate

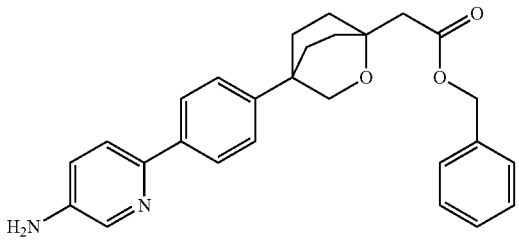 [SMILES: Nc1ccc(-c2ccc(C34CCC(CC(=O)OCc5ccccc5)(CC3)OC4)cc2)nc1]

To a mixture of methyl 2-(4-(4-(5-aminopyridin-2-yl)phenyl)-2-oxabicyclo[2.2.2]octan-1-yl)acetate (286 mg, 0.812 mmol) in neat benzyl alcohol (6 mL, 57.9 mmol) was added titanium(IV) isopropoxide (1.5 mL, 5.12 mmol) and 4 A molecular sieves (5 g, 0.812 mmol). The reaction mixture was heated at 130° C. overnight. The reaction was quenched by saturated NaHCO3 and was extracted with EtOAc. The combined organic layer was filtered and washed with brine and dried over anhydrous sodium sulfate, filtered and concentrated. The residue was purified by prep-HPLC (15 to 90% ACN-water (0.1% NH4OH) with X-bridge C18 column) to give the title compound after drying (150 mg, 43% yield). LC/MS, ESI-MS(+): 429.1, RT: 1.41 (Condition E).

Step 2. Synthesis of benzyl 2-(4-(4-(5-((5-(tert-butyl) oxazol-2-yl)amino)pyridin-2-yl)phenyl)-2-oxabicyclo[2.2.2]octan-1-yl)acetate

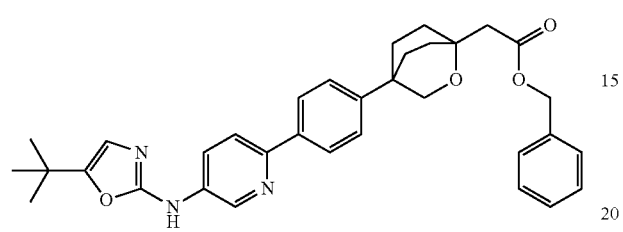

To a solution of benzyl 2-(4-(4-(5-aminopyridin-2-yl)phenyl)-2-oxabicyclo[2.2.2]octan-1-yl)acetate (150 mg, 0.350 mmol) in DCM (6 ml) at room temperature was added 1,1'-thiocarbonyldi-2(1H)-pyridone (85 mg, 0.368 mmol) and the reaction was stirred at room temperature for 0.5 hr. To the mixture was added 1-amino-3,3-dimethylbutan-2-one (80 mg, 0.525 mmol) and DIPEA (0.110 ml, 0.630 mmol) and the mixture was stirred at 40° C. or until the reaction was completed. To the mixture was added EDC.HCl (268 mg, 1.400 mmol) and the reaction was stirred at 40° C. overnight. The reaction mixture was concentrated and purified by flash chromatography (10 to 50% EtOAc/Heptane) to give the title compound (100 mg, 51.8% yield). LC/MS, ESI-MS(+) m/z 552.1, RT: 1.73 (Condition R).

Step 3. Synthesis of 2-(4-(4-(5-((5-(tert-butyl)oxazol-2-yl)amino)pyridin-2-yl)phenyl)-2-oxabicyclo[2.2.2]octan-1-yl)acetic acid

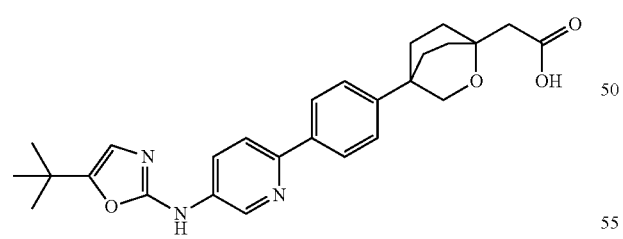

Benzyl 2-(4-(4-(5-((5-(tert-butyl)oxazol-2-yl)amino)pyridin-2-yl)phenyl)-2-oxabicyclo[2.2.2]octan-1-yl)acetate (100 mg, 0.181 mmol) was dissolved in EtOAc/THF and hydrogenated with 10% Pd(OH)$_2$/C under H$_2$ balloon for 3 hr. The reaction mixture was filtered and the filtrate was concentrated. The residue was purified by prep-HPLC to give the title compound (28 mg, 31.5% yield). HR/MS [M+H]$^+$: found 462.2390. calc. 462.2393. RT: 2.83 (Condition L). $^1$H NMR (400 MHz, DMSO-d$_6$) δ ppm 1.26 (s, 9H), 1.86-2.03 (m, 8H), 2.32 (s, 2H), 3.90 (s, 2H), 6.60 (s, 1H), 7.39 (d, J=8.59 Hz, 2H), 7.87 (d, J=8.59 Hz, 1H), 7.95 (d, J=8.59 Hz, 2H), 8.15 (dd, J=8.84, 2.78 Hz, 1H), 8.77 (d, J=2.78 Hz, 1H), 10.36 (br. s., 1H).

EXAMPLE 15

2-(4-(4'-((5-(tert-butyl)oxazol-2-yl)amino)-[1,1'-biphenyl]-4-yl)-2-oxabicyclo[2.2.2]octan-1-yl)acetic acid Step 1. Synthesis of benzyl 2-(4-(4'-amino-[1,1'-biphenyl]-4-yl)-2-oxabicyclo[2.2.2]octan-1-yl)acetate

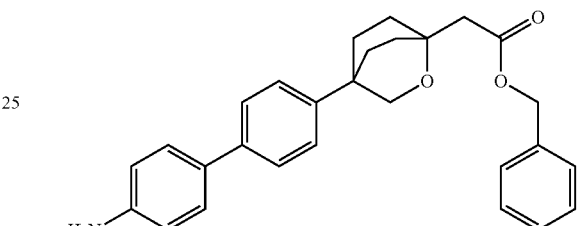

To a mixture of methyl 2-(4-(4'-amino-[1,1'-biphenyl]-4-yl)-2-oxabicyclo[2.2.2]octan-1-yl)acetate (0.323 g, 0.918 mmol) in toluene (35 ml) was added benzyl alcohol (2.377 ml, 22.95 mmol), titanium(IV) isopropoxide (0.807 ml, 2.75 mmol) and 4 A molecular sieves (5 g, 0.918 mmol). The reaction mixture was heated at 120° C. for 48 hours. The resulting mixture was taken up in EtOAc and filtered. The filtrate was subsequently washed with water, then brine. The organic portion dried over anhydrous sodium sulfate, filtered and concentrated. The residue was purified by flash chromatography (10 to 50% EtOAc/Heptane) to give the title compound after drying (270 mg, yield 68.8% yield). LC/MS, ESI-MS(+) m/z 428.1, RT 1.59 (Condition R).

Step 2. Synthesis of benzyl 2-(4-(4'-((5-(tert-butyl) oxazol-2-yl)amino)-[1,1'-biphenyl]-4-yl)-2-oxabicyclo[2.2.2]octan-1-yl)acetate

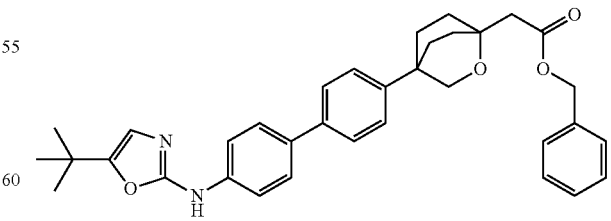

The title compound was prepared analogous to Example 14, step 2 starting from benzyl 2-(4-(4'-amino-[1,1'-biphenyl]-4-yl)-2-oxabicyclo[2.2.2]octan-1-yl)acetate (240 mg, 0.32 mmol). After workup the crude product was purified by column chromatography to give the title compound (200 mg, 89% yield). LC/MS, ESI-MS(+) m/z 551.1, RT 1.82 (Condition R).

Step 3. 2-(4-(4'-((5-(tert-butyl)oxazol-2-yl)amino)-[1,1'-biphenyl]-4-yl)-2-oxabicyclo[2.2.2]octan-1-yl)acetic acid

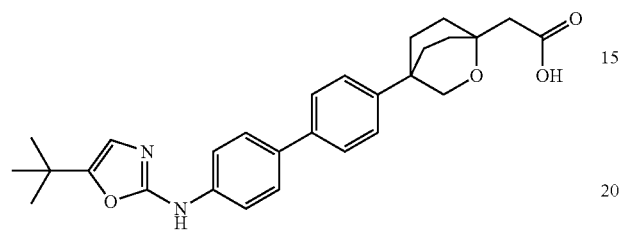

The title compound was prepared analogous to Example 14, step 3 starting from benzyl 2-(4-(4'-((5-(tert-butyl)oxazol-2-yl)amino)-[1,1'-biphenyl]-4-yl)-2-oxabicyclo[2.2.2]octan-1-yl)acetate (200 mg, 0.36 mmol). After workup the crude product was purified by prep-HPLC to give the title compound (37 mg, 22% yield). HR/MS [M+H]$^+$: found 461.2427. calc. 461.2440. RT: 2.85 (Condition L). $^1$H NMR (400 MHz, DMSO-d$_6$) δ ppm 1.26 (s, 9H), 1.82-2.07 (m, 8H), 2.33 (s, 2H), 3.89 (s, 2H), 6.58 (s, 1H), 7.37 (d, J=8.59 Hz, 2H), 7.51-7.61 (m, 4H), 7.61-7.70 (m, 2H), 10.16 (s, 1H).

EXAMPLE 16

2-(4-(4'-((5-isobutyl-1,3,4-oxadiazol-2-yl)amino)-[1,1'-biphenyl]-4-yl)-2-oxabicyclo[2.2.2]octan-1-yl)acetic acid Step 1. Synthesis of 5-isobutyl-N-(4-(4,4,5,5-tetramethyl-1,3,2-dioxaborolan-2-yl)phenyl)-1,3,4-oxadiazol-2-amine

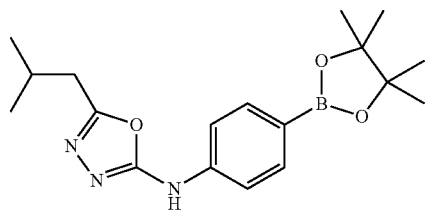 [SMILES: CC(C)Cc1nnc(Nc2ccc(B3OC(C)(C)C(C)(C)O3)cc2)o1]

To a stirred solution of 4-(4,4,5,5-tetramethyl-1,3,2-dioxaborolan-2-yl) aniline (200 mg, 0.91 mmol) in methylene chloride (4.5 ml) was added 1,1'-thiocarbonyldipyridin-2(1H)-one (212 mg, 0.91 mmol) and stirred at room temperature for 1 hour. Upon complete formation of the isothiocyanate, 3-methylbutanehydrazide (159 mg, 1.37 mmol) was added to the mixture and stirred at room temperature for overnight. EDC (315 mg, 1.64 mmol) was then added and the reaction stirred at room temperature for 14 hours. The reaction was concentrated to dryness and taken up in water to form a slurry. The slurry was filtered and washed with water to afford the crude product, which was purified by column chromatography to afford the title compound as off-white solid after drying (217 mg, 69% yield). LC/MS, ESI-MS(+) m/z 344.1, RT 1.45 (Condition R).

Step 2. Synthesis of methyl 2-(4-(4'-(5-isobutyl-1,3,4-oxadiazol-2-ylamino)biphenyl-4-yl)-2-oxabicyclo[2.2.2]octan-1-yl)acetate

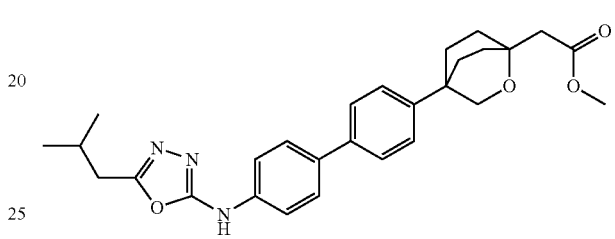

The title compound was prepared analogous to Example 10, step 2 starting from 5-isobutyl-N-(4-(4,4,5,5-tetramethyl-1,3,2-dioxaborolan-2-yl)phenyl)-1,3,4-oxadiazol-2-amine (61 mg, 0.18 mmol). After workup the crude product was purified by column chromatography to afford the title compound after drying (56 mg, 79% yield). LC/MS, ESI-MS(+) m/z 476.1, RT 1.50 (Condition R).

Step 3. Synthesis of 2-(4-(4'-((5-isobutyl-1,3,4-oxadiazol-2-yl)amino)-[1,1'-biphenyl]-4-yl)-2-oxabicyclo[2.2.2]octan-1-yl)acetic acid

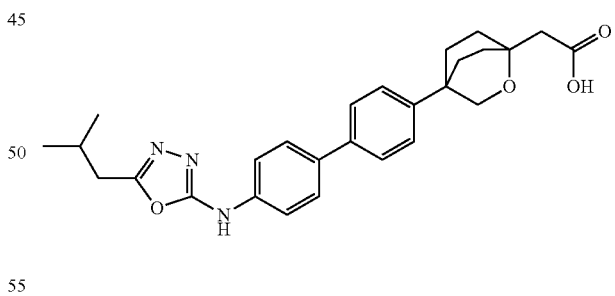

The title compound was prepared analogous to Example 4, Step 4 starting from methyl 2-(4-(4'-(5-isobutyl-1,3,4-oxadiazol-2-ylamino)biphenyl-4-yl)-2-oxabicyclo[2.2.2]octan-1-yl)acetate (56 mg, 0.12 mmol) and NaOH (0.35 ml, 0.35 mmol). After acidification with 1N HCl, the slurry was filtered and washed with water to afford the title compound as white solid after drying (52 mg, 97% yield). HR/MS (M+H)$^+$ found 462.2399. calc. 462.2406. RT: 2.40 (Condition L). $^1$H NMR (400 MHz, DMSO-d$_6$) δ ppm 10.02-10.86 (m, 1H) 7.62 (s, 5H) 7.53-7.59 (m, 2H) 7.37 (d, J=8.59 Hz, 2H) 3.85 (s, 2H)

2.65 (d, J=7.07 Hz, 2H) 2.11-2.25 (m, 2H) 2.00-2.09 (m, 3H) 1.90-2.00 (m, 2H) 1.81 (d, J=13.39 Hz, 4H) 0.97 (d, J=6.82 Hz, 6H)

EXAMPLE 17

2-(4-(4'-((5-neopentyl-1,3,4-oxadiazol-2-yl)amino)-[1,1'-biphenyl]-4-yl)-2-oxabicyclo[2.2.2]octan-1-yl)acetic acid Step 1. Synthesis of 3,3-dimethylbutanehydrazide

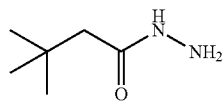

To a mixture of methyl 3,3-dimethylbutanoate (500 mg, 3.84 mmol) in EtOH (12 ml) was added hydrazine monohydrate (1.87 ml, 38.4 mmol). The mixture was heated to 80° C. under reflux for overnight. The reaction was cooled back down to room temperature and concentrated to dryness affording a crude residue. The residue was dried under high vacuum to afford the title compound as crystalline solid (90 mg, 18% yield). $^1$H NMR (400 MHz, DMSO-d$_6$) δ ppm 8.69-9.12 (s, 1H) 4.13 (br. s, 2H) 1.89 (s, 2H) 0.94 (s, 9H).

Step 2. Synthesis of benzyl 2-(4-(4'-(5-neopentyl-1,3,4-oxadiazol-2-ylamino)biphenyl-4-yl)-2-oxabicyclo[2.2.2]octan-1-yl)acetate

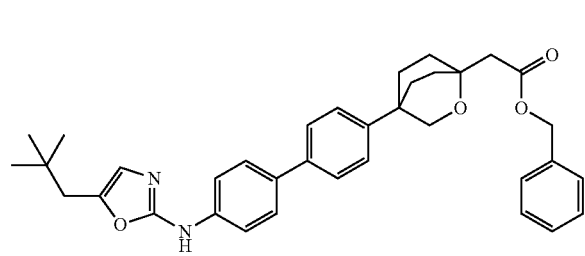 [SMILES: CC(C)(C)Cc1cnc(Nc2ccc(-c3ccc(C45CCC(CC(=O)OCc6ccccc6)(CC4)OC5)cc3)cc2)o1]

The title compound was prepared analogous to Example 1, Step 9 starting from benzyl 2-(4-(4'-amino-[1,1'-biphenyl]-4-yl)-2-oxabicyclo[2.2.2]octan-1-yl)acetate (30 mg, 0.07 mmol) and 3,3-dimethylbutanehydrazide (14 mg, 0.11 mmol). The crude residue was purified by column chromatography to afford the title compound as off-white solid after drying (34 mg, 86% yield). LC/MS, ESI-MS(+): 566.1, RT: 1.73 (Condition R).

Step 3. Synthesis of 2-(4-(4'-((5-neopentyl-1,3,4-oxadiazol-2-yl)amino)-[1,1'-biphenyl]-4-yl)-2-oxabicyclo[2.2.2]octan-1-yl)acetic acid

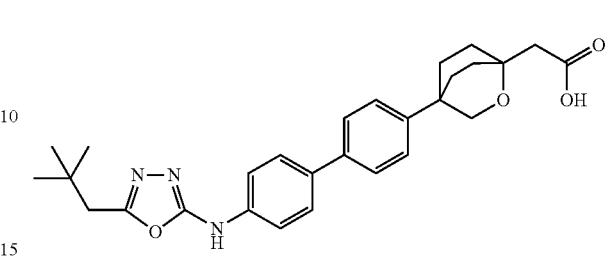

The title compound was prepared analogous to Example 14, Step 3 starting from benzyl 2-(4-(4'-(5-neopentyl-1,3,4-oxadiazol-2-ylamino)biphenyl-4-yl)-2-oxabicyclo[2.2.2]octan-1-yl)acetate (34 mg, 0.06 mmol) I). After hydrogenation, the mixture was filtered and the filtercake was washed with hot MeOH. The resulting filtrate was concentrated to afford a crude solid. The crude material was triturated with DCM, filtered and washed with a small amount of DCM to afford the title compound as white solid after drying (10 mg, 34% yield). HR/MS (M+H)$^+$ found 476.2535. calc. 462.2549. RT: 2.54 (Condition L). $^1$H NMR (400 MHz, DMSO-d$_6$) δ ppm 10.44-10.60 (m, 1H) 7.63 (s, 4H) 7.57 (d, J=8.59 Hz, 2H) 7.37 (d, J=8.59 Hz, 2H) 3.87 (s, 2H) 2.66 (s, 2H) 2.18 (s, 2H) 1.80-2.12 (m, 8H) 1.01 (s, 9H).

EXAMPLE 18

{1-[4'-(5-tert-butyl-[1,3,4]oxadiazol-2-ylamino)-biphenyl-4-yl]-2-oxa-bicyclo[2.2.2]oct-4-yl}-acetic acid Step 1. Synthesis of 4-trifluoromethanesulfonyloxy-cyclohex-3-ene-1,1-dicarboxylic acid diethyl ester

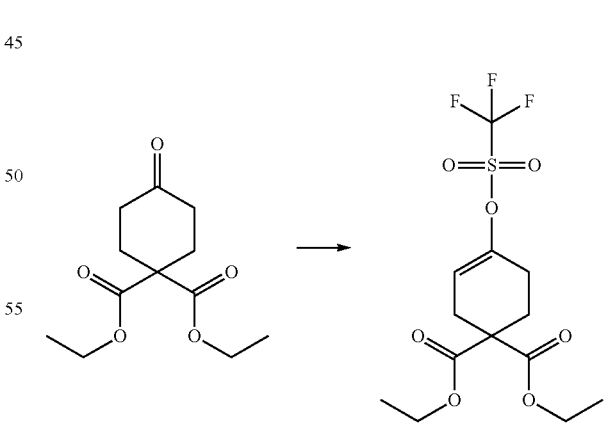

An oven-dried flask charged with diisopropylamine (4.90 ml, 34.7 mmol) and tetrahydrofuran (30 ml), was cooled to 0° C. under nitrogen atmosphere. To the reaction mixture was added n-butyl lithium (1.6M in hexanes, 21.67 ml, 34.7 mmol) dropwise and then stirred at 0° C. for 15 minutes. The reaction mixture was cooled to −78° C. and added the solution of 4-oxo-cyclohexane-1,1-dicarboxylic acid diethyl ester (7.0 g, 28.9 mmol) in tetrahydrofuran (15 ml) over 2 minutes. The reaction mixture was stirred at −30° C. for 30 minutes, and then cooled to −78° C., and followed by adding the solution of 2-[N,N-bis(trifluoromethylsulfonyl)amino]-5-chloropyridine (12.48 g, 31.8 mmol) in tetrahydrofuran (15 ml). The reaction mixture was allowed to warm to room temperature and stirred for 2 hours. The reaction mixture was concentrated and the resulting oil was partitioned between ethyl acetate/heptane (3/1; 200 ml) and water (100 ml). The layers were separated and the organic phase was washed with water (5×50 ml), dried over $Na_2SO_4$, and concentrated to afford the crude 4-trifluoromethanesulfonyloxy-cyclohex-3-ene-1,1-dicarboxylic acid diethyl ester (12.8 g, 80% purity, 94% yield) as brown oil. $^1$H NMR (400 MHz, CHLOROFORM-d) δ ppm 1.27 (t, J=7.20 Hz, 6H) 2.25-2.35 (m, 2H) 2.43 (dd, J=6.19, 1.89 Hz, 2H) 2.72-2.80 (m, 2H) 4.21 (q, J=7.20 Hz, 4H) 5.69-5.82 (m, 1H).

Step 2. Synthesis of 4-(4-chloro-phenyl)-cyclohex-3-ene-1,1-dicarboxylic acid diethyl ester

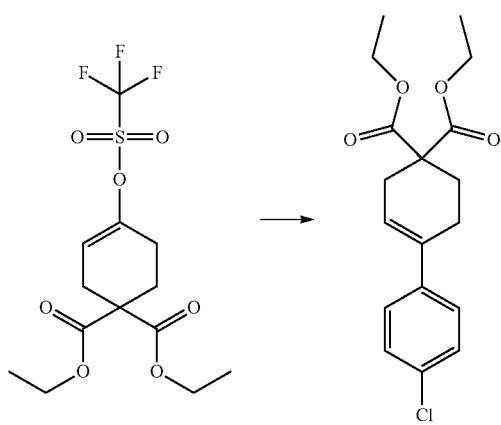 [SMILES: CCOC(=O)C1(C(=O)OCC)CC=C(OS(=O)(=O)C(F)(F)F)CC1 ; CCOC(=O)C1(C(=O)OCC)CC=C(c2ccc(Cl)cc2)CC1]

A 100 ml heavy wall round bottom flask was charged with the crude intermediate 4-trifluoromethanesulfonyloxy-cyclohex-3-ene-1,1-dicarboxylic acid diethyl ester (4.0 g, 80% purity, 8.55 mmol, 1.0 equiv) from last step, $PdCl_2(dppf)\text{-}CH_2Cl_2$ adduct (0.628 g, 0.769 mmol, 0.09 equiv), 4-chlorophenylboric acid (2.67 g, 17.1 mmol, 2.0 equiv), tripotassium phosphate (4.54 g, 21.37 mmol, 2.5 equiv), ethanol (8 ml), dimethoxyethane (32.0 ml) and t-butyl acetylene (7.9 g, 97 mmol, 2.0 equiv). The flask was sealed, flushed with nitrogen for three times and stirred at 80° C. for 16 hours. After cooled at room temperature, the reaction mixture was filtered and washed with ethyl acetate (20 ml). The filtrate was concentrated under vacuum and the residue was purified by chromatography (heptanes/ethyl acetate 2/1) to give 4-(4-chloro-phenyl)-cyclohex-3-ene-1,1-dicarboxylic acid diethyl ester (2.2 g, 76%) as colorless oil. $^1$H NMR (400 MHz, CHLOROFORM-d) δ ppm 1.27 (t, J=8.00 Hz, 6H) 2.29 (t, J=6.38 Hz, 2H) 2.46 (td, J=6.25, 2.02 Hz, 2H) 2.65-2.85 (m, 2H) 4.21 (q, J=8.00 Hz, 4H) 6.07 (m, 1H) 7.26 (s, 4H).

Step 3. Synthesis of [4-(4-chloro-phenyl)-1-hydroxymethyl-cyclohex-3-enyl]-methanol

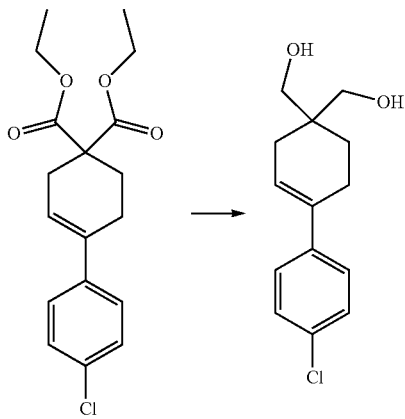 [SMILES: CCOC(=O)C1(C(=O)OCC)CC=C(c2ccc(Cl)cc2)CC1 ; OCC1(CO)CC=C(c2ccc(Cl)cc2)CC1]

An oven-dried flask under nitrogen was charged with 4-(4-chloro-phenyl)-cyclohex-3-ene-1,1-dicarboxylic acid diethyl ester (6.5 g, 19.30 mmol) in tetrahydrofuran (80 ml), and at −78° C. was added lithium alumina hydride (30.9 ml, 30.9 mmol) in one portion. The mixture was allowed to warm to room temperature and stirred for 2 hours. The reaction was quenched with saturated aqueous sodium chloride solution (5 ml) at 0° C. The mixture was filtered and the filtrate was extracted with ethyl acetate (3×100 ml), and the residue solid was washed with acetone (100 ml). The organic solvents were combined, dried over $Na_2SO_4$, and concentrated. The residue was purified by chromatography (heptanes/acetone 1/2) to afford [4-(4-chloro-phenyl)-1-hydroxymethyl-cyclohex-3-enyl]-methanol (4.7 g, 96%) as white solid. $^1$H NMR (400 MHz, METHANOL-$d_4$) δ ppm 1.64-1.74 (m, 2H) 2.04 (d, J=3.66 Hz, 2H) 2.37-2.46 (m, 2H) 3.50 (td, J=10.80, 8.80 Hz, 4H) 6.03-6.11 (m, 1H) 7.27 (d, J=8.40 Hz, 2H) 7.36 (d, J=8.40 Hz, 2H).

Step 4. Synthesis of [6-bromo-1-(4-chloro-phenyl)-2-oxa-bicyclo[2.2.2]oct-4-yl]-methanol

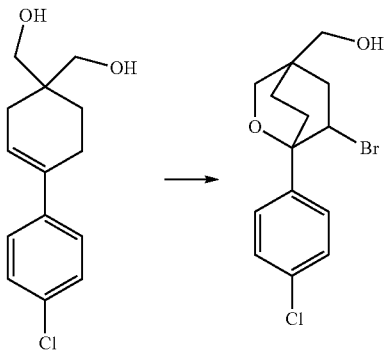 [SMILES: OCC1(CO)CC=C(c2ccc(Cl)cc2)CC1 ; OCC12CCC(c3ccc(Cl)cc3)(OC1)C(Br)C2]

To a stirred solution of [4-(4-chloro-phenyl)-1-hydroxymethyl-cyclohex-3-enyl]-methanol (4.7 g, 18.60 mmol) in tetrahydrofuran (280 ml) at 0° C., was added the solution of N-bromosuccinimde (3.48 g, 19.53 mmol) in dichloromethane (150 ml). The reaction mixture was allowed to warm to room temperature for 1 hour. The mixture was concentrated and the residue was purified by chromatography (heptanes/acetone 1/2) to afford [6-bromo-1-(4-chloro-phenyl)-2-oxa-bicyclo[2.2.2]oct-4-yl]-methanol (4.4 g, 71%) as colorless oil. $^1$H NMR (400 MHz, CHLOROFORM-d) δ ppm 1.79 (d, J=11.62 Hz, 2H) 2.07-2.25 (m, 2H) 2.59-2.71 (m, 1H) 2.82-2.95 (m, 1H) 3.42 (s, 2H) 3.91 (s, 2H) 4.33 (d, J=9.60 Hz, 1H) 7.30 (d, J=8.72 Hz, 2H) 7.42 (d, J=8.59 Hz, 2H).

Step 5. Synthesis of 6-bromo-1-(4-chloro-phenyl)-2-oxa-bicyclo[2.2.2]octane-4-carbaldehyde

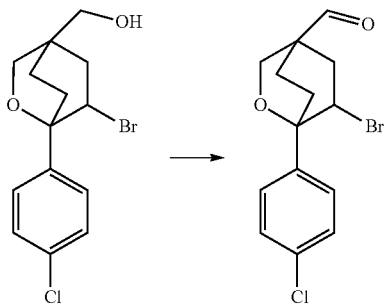 [SMILES: OCC12CCC(c3ccc(Cl)cc3)(OC1)C(Br)C2 ; O=CC12CCC(c3ccc(Cl)cc3)(OC1)C(Br)C2]

To a stirred solution of [6-bromo-1-(4-chloro-phenyl)-2-oxa-bicyclo[2.2.2]oct-4-yl]-methanol (2.47 g, 7.45 mmol) in dichloromethane (100 ml) at −78° C., was added Dess-Martin periodinane (3.32 g, 7.82 mmol). The reaction mixture was allowed to warm to 0° C. for 30 minutes and then room temperature for 60 minutes. Most of the solvent was removed by evaporation under vacuum at the room temperature and the residue was purified by flash chromatography (heptanes/acetone 1/2) to afford 6-bromo-1-(4-chloro-phenyl)-2-oxa-bicyclo[2.2.2]octane-4-carbaldehyde (2.0 g, 81%) as colorless oil. $^1$H NMR (400 MHz, CHLOROFORM-d) δ ppm 1.98-2.21 (m, 3H) 2.34-2.44 (m, 1H) 2.69-2.80 (m, 1H) 2.82-2.92 (m, 1H) 3.92-4.08 (m, 2H) 4.21-4.32 (m, 1H) 7.25 (d, J=8.60 Hz, 2H) 7.34 (d, J=8.60 Hz, 2H) 9.44 (s, 1H).

Step 6. Synthesis of 6-bromo-1-(4-chloro-phenyl)-4-(2-methoxy-vinyl)-2-oxa-bicyclo[2.2.2]octane

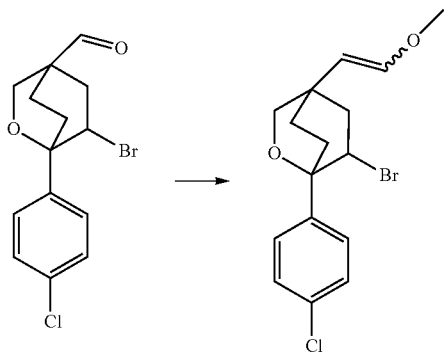 [SMILES: O=CC12CCC(c3ccc(Cl)cc3)(OC1)C(Br)C2 ; COC=CC12CCC(c3ccc(Cl)cc3)(OC1)C(Br)C2]

To a solution of triphenylphosphine methoxymethane chloride (3.51 g, 10.24 mmol) in tetrahydrofuran (20 ml) under nitrogen at room temperature, was added potassium t-butoxide (1.149 g, 10.24 mmol). The reddish solution was stirred at room temperature for 90 minutes. Then a solution of 6-bromo-1-(4-chloro-phenyl)-2-oxa-bicyclo[2.2.2]octane-4-carbaldehyde (2.25 g, 6.83 mmol) in tetrahydrofuran (6 ml) was added to the reaction mixture. The reaction mixture was stirred at room temperature for 10 minutes and then quenched with water (2 ml). The mixture was partitioned between brine (15 ml) and ethyl acetate (60 ml). The aqueous layer was extracted with ethyl acetate (2×30 ml) and the combined organic extracts were washed with brine, dried over Na$_2$SO$_4$, and concentrated. The residue was purified by flash chromatography (heptanes/acetone 2/1) to afford the cis and trans mixtures of 6-bromo-1-(4-chloro-phenyl)-4-(2-methoxy-vinyl)-2-oxa-bicyclo[2.2.2]octane (2.32 g, 95%) as colorless oil. $^1$H NMR (400 MHz, CHLOROFORM-d) δ ppm 1.74-2.99 (m, 6H) 3.54 (3.89 (m, 4H) 3.91-6.36 (m, 5H) 7.28-7.43 (m, 4H).

Step 7. Synthesis of [6-bromo-1-(4-chloro-phenyl)-2-oxa-bicyclo[2.2.2]oct-4-yl]-acetic acid methyl ester

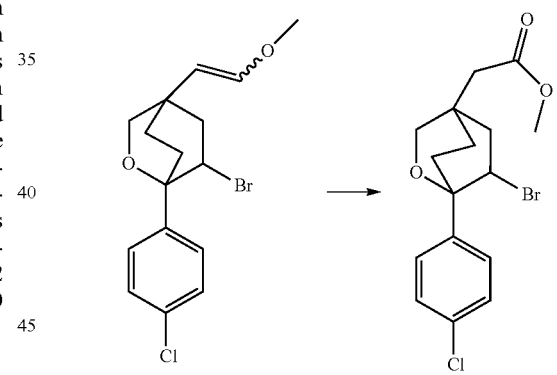

To a stirred solution of the cis and trans mixtures of 6-bromo-1-(4-chloro-phenyl)-4-(2-methoxy-vinyl)-2-oxa-bicyclo[2.2.2]octane (1.7 g, 4.75 mmol) in dichloromethane (12 ml) and tetrahydrofuran (25 ml) at room temperature, was portionally added pyridinium chlorochromate (3.07 g, 14.26 mmol). The reaction mixture was stirred at room temperature for 2 hours. More pyridinium chlorochromate (2.05 g, 9.51 mmol) was added, and the mixture was stirred for another 60 hours at room temperature. The mixture was filtrated and the filtrate was concentrated, and diluted with ethyl acetate (100 ml). The organic phase was washed with water, brine and dried over Na$_2$SO$_4$, and concentrated. The residue was purified by flash chromatography (heptanes/acetone 2/1) to afford [6-bromo-1-(4-chloro-phenyl)-2-oxa-bicyclo[2.2.2]oct-4-yl]-acetic acid methyl ester (1.08 g, 61%) as colorless oil. $^1$H NMR (400 MHz, CHLOROFORM-d) δ ppm 1.69-1.79 (m, 1H) 1.87-1.98 (m, 1H) 2.01-2.11 (m, 1H) 2.14 (s, 2H) 2.23-2.30 (m, 1H) 2.52-2.63 (m, 1H) 2.75-2.87 (m, 1H) 3.62 (s, 3H) 3.84 (dd, J=10.11, 2.65 Hz, 2H) 4.19-4.29 (m, 1H) 7.23 (d, J=8.80 Hz, 2H) 7.33 (d, J=8.80 Hz, 2H).

Step 8. Synthesis of [1-(4-chloro-phenyl)-2-oxa-bicyclo[2.2.2]oct-4-yl]acetic acid methyl ester

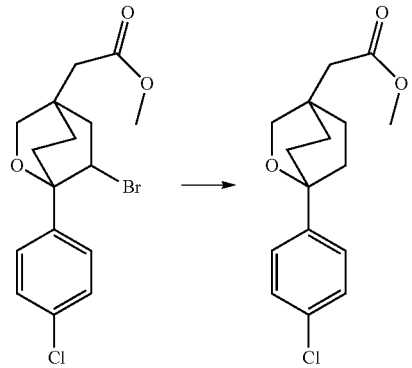 [SMILES: COC(=O)CC12CCC(c3ccc(Cl)cc3)(OC1)C(Br)C2 ; COC(=O)CC12CCC(c3ccc(Cl)cc3)(CC1)OC2]

To a stirred solution of [6-bromo-1-(4-chloro-phenyl)-2-oxa-bicyclo[2.2.2]oct-4-yl]-acetic acid methyl ester (0.75 g, 2.007 mmol) and nickel (II) chloride (0.182 g, 1.405 mmol) in methanol (30 ml), ethyl acetate (15 ml), tetrahydrofuran (15 ml) and chlorobenzene (2 ml) at −30° C., was added carefully sodium borohydride (0.228 g, 6.02 mmol). The reaction mixture was allowed to warm to room temperature for 40 minutes. The solvent was removed under vacuum at room temperature and then water (20 ml) and EtOAc (100 ml) were added. The organic phase was separated and washed with brine, dried over $Na_2SO_4$ and concentrated. The residue was purified by flash chromatography (heptanes/acetone 2/1) to afford [1-(4-chloro-phenyl)-2-oxa-bicyclo[2.2.2]oct-4-yl]-acetic acid methyl ester (0.39 g, 66%) as white solid. $^1$H NMR (400 MHz, CHLOROFORM-d) δ ppm 1.65-1.81 (m, 4H) 1.96 (t, J=8.00 Hz, 4H) 2.11 (s, 2H) 3.62 (s, 3H) 3.87 (s, 2H) 7.20 (d, J=8.60 Hz, 2H) 7.25 (d, J=8.60 Hz, 2H).

Step 9. Synthesis of {1-[4'-(5-tert-butyl-[1,3,4]oxadiazol-2-ylamino)-biphenyl-4-yl]-2-oxa-bicyclo[2.2.2]oct-4-yl}-acetic acid methyl ester

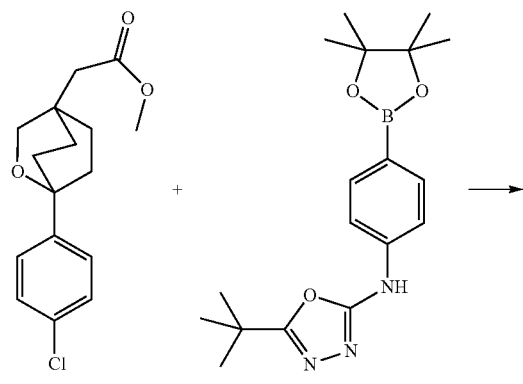

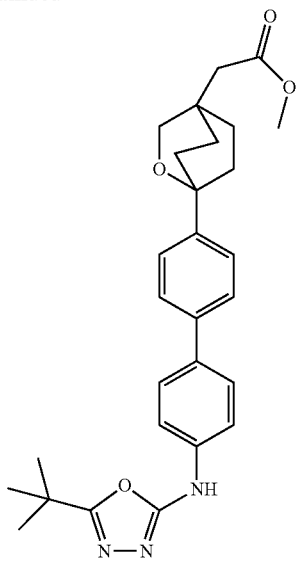

To a solution of [1-(4-chloro-phenyl)-2-oxa-bicyclo[2.2.2]oct-4-yl]-acetic acid methyl ester (0.29 g, 0.984 mmol) and (5-tert-butyl-[1,3,4]oxadiazol-2-yl)-[4-(4,4,5,5-tetramethyl-[1,3,2]dioxaborolan-2-yl)-phenyl]-amine (0.338 g, 0.984 mmol) in dioxane (8 ml) and water (0.8 ml), was added caesium fluoride (0.448 g, 2.95 mmol) and Pd(amphos)Cl$_2$ (0.070 g, 0.098 mmol). The mixture was flushed with nitrogen for three times and heated at 90° C. for 16 hours. The reaction mixture was filtered, and the solid was washed with water (10 ml) and ethyl acetate (3 ml) to afford crude {1-[4'-(5-tert-butyl-[1,3,4]oxadiazol-2-ylamino)-biphenyl-4-yl]-2-oxa-bicyclo[2.2.2]oct-4-yl}-acetic acid methyl ester (0.27 g, 58%) as white solid. [MS+1] 476.31.

Step 10. Synthesis of {1-[4'-(5-tert-butyl-[1,3,4]oxadiazol-2-ylamino)-biphenyl-4-yl]-2-oxa-bicyclo[2.2.2]oct-4-yl}-acetic acid

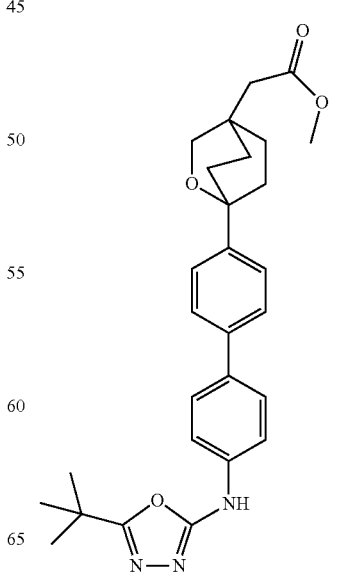

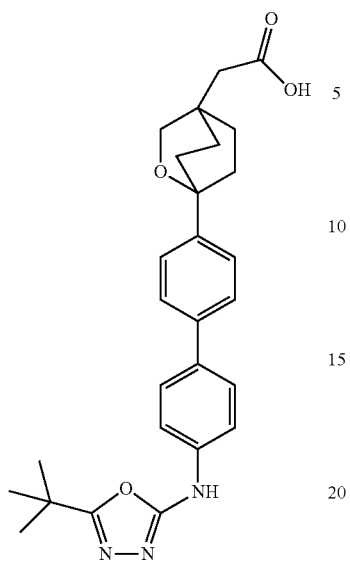

A 100 ml round bottom flask was charged with {1-[4'-(5-tert-butyl-[1,3,4]oxadiazol-2-ylamino)-biphenyl-4-yl]-2-oxa-bicyclo[2.2.2]oct-4-yl}-acetic acid methyl ester (0.27 g, 0.454 mmol), and lithium hydroxide monohydrate (0.229 g, 5.45 mmol) in tetrahydrofuran (20 ml), ethanol (10 ml) and water (8 ml) at room temperature. The mixture was heated at 50° C. for 2 hours. Most of the organic solvent was evaporated under vacuum and the mixture was acidified to PH=4 at 0° C. The solvents were then removed by lipherlizer. The mixture was added ethanol (40 ml) and heated to 70° C., and then was cooled to room temperature. The mixture was filtered and the solid was washed with ethanol (3 ml) and water (10 ml) to afford {1-[4'-(5-tert-butyl-[1,3,4]oxadiazol-2-ylamino)-biphenyl-4-yl]-2-oxa-bicyclo[2.2.2]oct-4-yl}-acetic acid (150 mg, 71%) as white solid. $^1$H NMR (400 MHz, DMSO-d$_6$) δ ppm 1.64-1.89 (m, 6H) 2.00-2.13 (m, 4H) 3.85 (s, 2H) 7.42 (d, J=8.40 Hz, 2H) 7.55 (d, J=8.50 Hz, 2H) 7.62 (s, 4H) 10.46 (br. s, 1H). LC/MS, [MS+] 461.23, RT: 2.66 (Condition M).

EXAMPLE 19

{1-[4'-(5-cyclobutyl-[1,3,4]oxadiazol-2-ylamino)-biphenyl-4-yl]-2-oxa-bicyclo[2.2.2]oct-4-yl}-acetic acid Step 1. methyl 2-(1-(4-(4,4,5,5-tetramethyl-1,3,2-dioxaborolan-2-yl)phenyl)-2-oxabicyclo[2.2.2]octan-4-yl)acetate

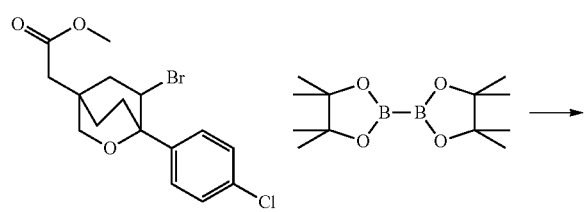

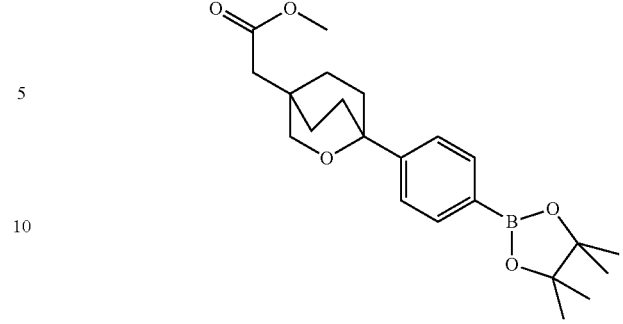

A vial was charged with [6-bromo-1-(4-chloro-phenyl)-2-oxa-bicyclo[2.2.2]oct-4-yl]-acetic acid methyl ester (80 mg, 0.214 mmol), pinoco boronate (163 mg, 0.642 mmol), potassium acetate (63.0 mg, 0.642 mmol), Pd(X-phos) (31.6 mg, 0.043 mmol) X-phos (30.6 mg, 0.064 mmol) and Dioxane (2 ml) at room temperature. The vial was sealed, flushed with nitrogen for three times and heated at 102° C. for 16 h. The mixture was cooled down and diluted with dioxane (5 ml) and EtOAc (50 ml), filtered and the filtrate was concentrated. The residue was added dioxane (30 ml) and filtered again, and the filtrate was purified by flash chromatography (heptanes/ethyl acetate 1/1) to afford methyl 2-(1-(4-(4,4,5,5-tetramethyl-1,3,2-dioxaborolan-2-yl)phenyl)-2-oxabicyclo[2.2.2]octan-4-yl)acetate (37 mg, 80% purity, 36% yield) as white solid. $^1$H NMR (400 MHz, CHLOROFORM-d) δ ppm 1.26 (s, 12H) 1.66-1.80 (m, 4H) 1.89-2.04 (m, 4H) 2.11 (s, 2H) 3.60 (s, 3H) 3.87 (s, 2H) 7.32 (d, J=8.21 Hz, 2H) 7.69 (d, J=8.08 Hz, 2H).

Step 2. Synthesis of methyl 2-(1-(4'-((5-cyclobutyl-1,3,4-oxadiazol-2-yl)amino)-[1,1'-biphenyl]-4-yl)-2-oxabicyclo[2.2.2]octan-4-yl)acetate

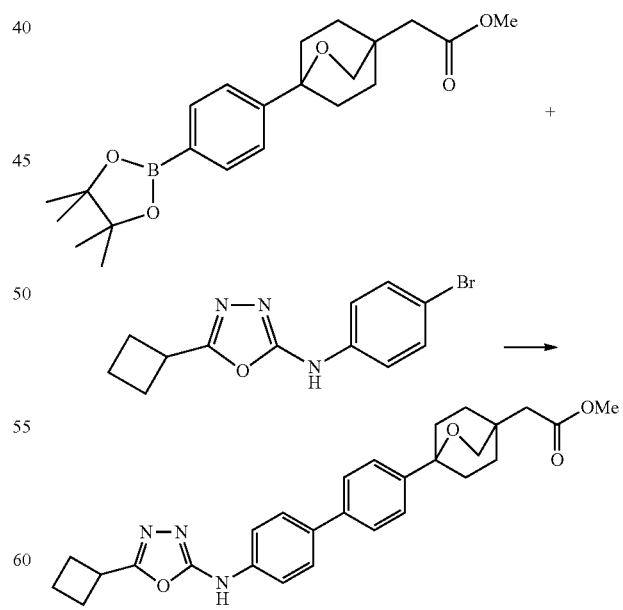

A vial was charged with methyl 2-(1-(4-(4,4,5,5-tetramethyl-1,3,2-dioxaborolan-2-yl)phenyl)-2-oxabicyclo[2.2.2]octan-4-yl)acetate (20 mg, 0.052 mmol), N-(4-bromophenyl)-5-cyclobutyl-1,3,4-oxadiazol-2-amine (30.5 mg, 0.104 mmol), PdCl₂(dppf)-CH₂Cl₂adduct (6.34 mg, 7.77 μmol), potassium phosphate (21.98 mg, 0.104 mmol), dimethoxyethane (0.6 ml), methanol (0.2 ml), and water (0.1 ml) at room temperature. The vial was sealed, flushed with nitrogen for three times and heated at 80° C. for 16 hours. The mixture was purified by flash chromatography (heptanes/acetone 1/1, washed with acetone/ethanol 1/1) to afford methyl 2-(1-(4'-((5-cyclobutyl-1,3,4-oxadiazol-2-yl)amino)-[1,1'-biphenyl]-4-yl)-2-oxabicyclo[2.2.2]octan-4-yl)acetate (40 mg, 40% purity, 65% yield) as white solid. LC/MS, ESI-MS(+) m/z 474.19, RT 1.41 (Condition E).

Step 3. Synthesis of {1-[4'-(5-cyclobutyl-[1,3,4]oxadiazol-2-ylamino)-biphenyl-4-yl]-2-oxa-bicyclo[2.2.2]oct-4-yl}-acetic acid A flask was charged with methyl 2-(1-(4'-((5-cyclobutyl-1,3,4-oxadiazol-2-yl)amino)-[1,1'-biphenyl]-4-yl)-2-oxabicyclo[2.2.2]octan-4-yl)acetate (0.040 g, 0.034 mmol), lithium hydroxide monohydrate (0.043 g, 1.040 mmol), tetrahydrofuran (1 ml), ethanol (0.3 ml) and water (0.3 ml), and stirred at 50° C. for 2 hours. The mixture was purified by HPLC (0.1% NH₄OH, 10-50% acetonitrile/water, 20 minutes run, retention time ~7 minutes) to afford {1-[4'-(5-cyclobutyl-[1,3,4]oxadiazol-2-ylamino)-biphenyl-4-yl]-2-oxa-bicyclo[2.2.2]oct-4-yl}-acetic acid (6 mg, 39%) as white solid. ¹H NMR (400 MHz, DMSO-d₆) δ ppm 1.67-1.89 (m, 5H) 1.89-2.00 (m, 1H) 2.00-2.14 (m, 5H) 2.26-2.39 (m, 5H) 3.62-3.73 (m, 1H) 3.86 (s, 2H) 7.43 (d, J=8.40 Hz, 2H) 7.55 (d, J=8.50 Hz, 2H) 7.62 (s, 4H) 10.39-10.59 (br. s, 1H). LC/MS, [MS+] 459.22, RT: 2.61 (Condition M).

EXAMPLE 20

(1-{4'-[(2-ethyl-4-methyl-oxazole-5-carbonyl)-amino]-biphenyl-4-yl}-2-oxa-bicyclo[2.2.2]oct-4-yl)-acetic acid Step 1. Synthesis of methyl 2-(1-(4'-(2-ethyl-4-methyloxazole-5-carboxamido)-[1,1'-biphenyl]-4-yl)-2-oxabicyclo[2.2.2]octan-4-yl)acetate

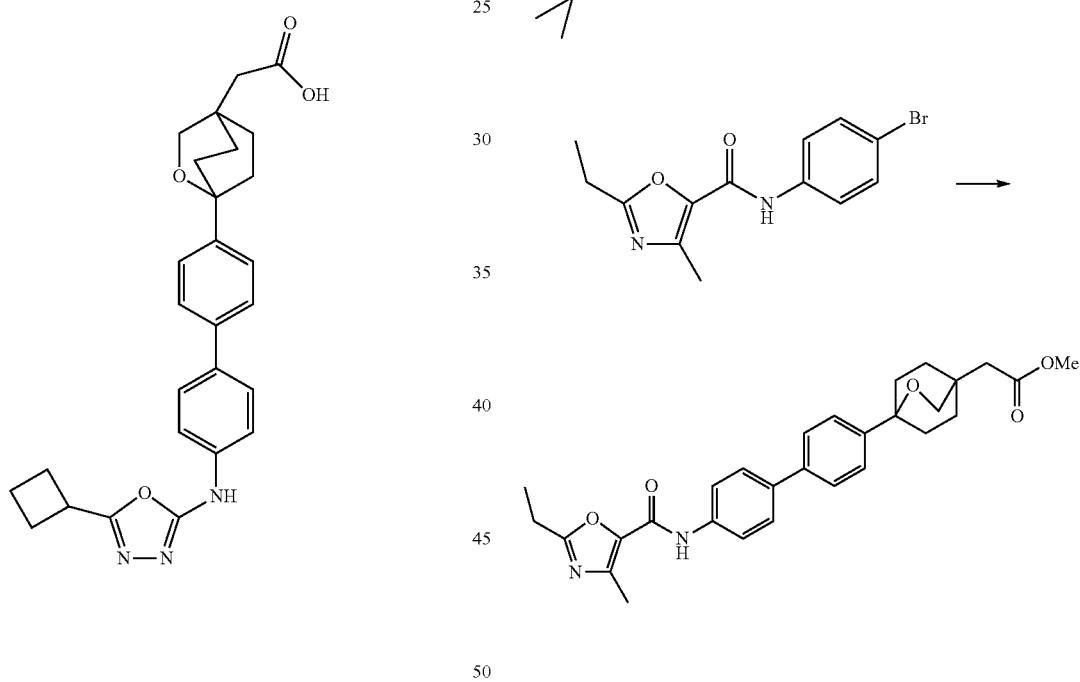

A vial was charged with methyl 2-(1-(4-(4,4,5,5-tetramethyl-1,3,2-dioxaborolan-2-yl)phenyl)-2-oxabicyclo[2.2.2]octan-4-yl)acetate (14 mg, 0.036 mmol), N-(4-bromophenyl)-2-ethyl-4-methyloxazole-5-carboxamide (22.4 mg, 0.072 mmol), PdCl₂(dppf)-CH₂Cl₂adduct (4.44 mg, 5.44 μmol), potassium phosphate (15.4 mg, 0.072 mmol), dimethoxyethane (0.6 ml), ethanol (0.2 ml), and water (0.1 ml) at room temperature. The vial was sealed, flushed with nitrogen for three times and heated at 80° C. for 16 hours. The mixture was purified by flash chromatography (heptanes/acetone 1/1, washed with acetone/ethanol 1/1) to afford methyl 2-(1-(4'-(2-ethyl-4-methyloxazole-5-carboxamido)-[1,1'-biphenyl]-4-yl)-2-oxabicyclo[2.2.2]octan-4-yl)acetate (25 mg, 40% purity, 56% yield) as white solid. LC/MS, ESI-MS(+) m/z 489.1, RT 1.53 (Condition E).

Step 2. Synthesis of (1-{4'-[(2-ethyl-4-methyl-oxazole-5-carbonyl)-amino]-biphenyl-4-yl}-2-oxabicyclo[2.2.2]oct-4-yl)-acetic acid

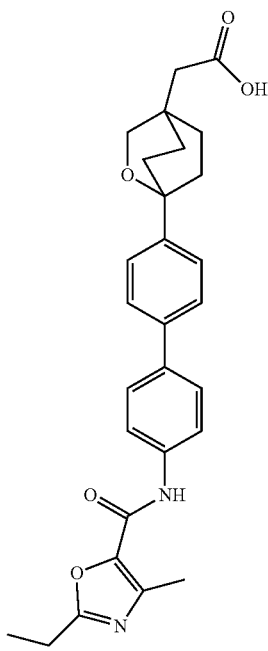 [SMILES: CCc1nc(C)c(C(=O)Nc2ccc(-c3ccc(C45CCC(CC(=O)O)(CC4)CO5)cc3)cc2)o1]

A flask was charged with methyl 2-(1-(4'-(2-ethyl-4-methyloxazole-5-carboxamido)-[1,1'-biphenyl]-4-yl)-2-oxabicyclo[2.2.2]octan-4-yl)acetate (0.025 g, 0.020 mmol), lithium hydroxide monohydrate (0.030 g, 0.716 mmol), tetrahydrofuran (1 ml), ethanol (0.3 ml) and water (0.3 ml), and stirred at 50° C. for 2 hours. The mixture was purified by HPLC (0.1% NH$_4$OH, 10-60% acetonitrile/water, 20 minutes run, retention time ~7 minutes) to afford (1-{4'-[(2-ethyl-4-methyl-oxazole-5-carbonyl)-amino]-biphenyl-4-yl}-2-oxabicyclo[2.2.2]oct-4-yl)-acetic acid (4 mg, 41%) as white solid. $^1$H NMR (400 MHz, DMSO-d$_6$) δ ppm 1.31 (t, J=7.58 Hz, 3H) 1.68-1.90 (m, 6H) 2.02-2.16 (m, 4H) 2.40 (s, 3H) 2.84 (q, J=7.58 Hz, 1H) 3.87 (s, 2H) 7.44 (d, J=8.46 Hz, 2H) 7.58 (d, J=8.59 Hz, 2H) 7.63 (d, J=8.72 Hz, 2H) 7.83 (d, J=8.72 Hz, 2H) 10.13 (s, 1H). LC/MS, [MS+] 474.22, RT: 2.65 (Condition M).

EXAMPLE 21

(1-{4-[5-(5-cyclobutyl-[1,3,4]oxadiazol-2-ylamino)-pyridin-2-yl]-phenyl}-2-oxa-bicyclo[2.2.2]oct-4-yl)-acetic acid Step 1. Synthesis of 2-(4-chlorophenyl)-5-nitropyridine

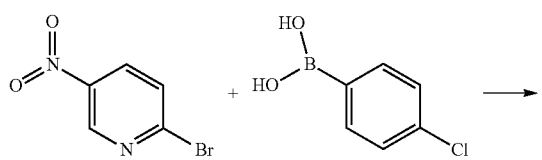

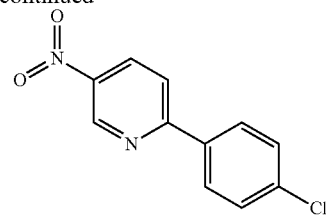

A flask was charged with 2-bromo-5-nitropyridine (4 g, 19.71 mmol), 4-chlorophenylboronic acid (4.54 g, 27.6 mmol), Pd(PPh3)4 (1.139 g, 0.985 mmol), potassium carbonate (8.16 g, 59.1 mmol), dioxane (40 ml) and water (20 ml) at room temperature. The flask was sealed, flushed with nitrogen for three times and heated at 100° C. for 3 hours. The reaction mixture was diluted with EtOAc (100 ml) and filtered. The filtrate was concentrated. The residue was washed with water by filtration. The afforded solid was dissolved in EtOAc (200 ml) and washed with saturated aqueous sodium bicarbonate solution and brine, dried over Na$_2$SO$_4$, concentrated, and dried under vacuum to afford crude 2-(4-chlorophenyl)-5-nitropyridine (4.8 g, 75% purity, 78% yield) as yellow solid. $^1$H NMR (400 MHz, DMSO-d$_6$) ppm 7.27-7.36 (m, 4H) 7.51-7.61 (m, 3H).

Step 2. Synthesis of 5-nitro-2-(4-(4,4,5,5-tetramethyl-1,3,2-dioxaborolan-2-yl)phenyl)pyridine

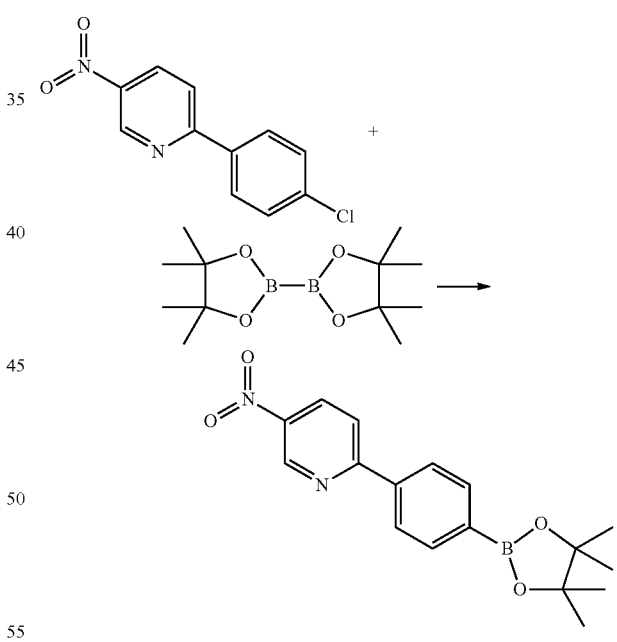

A flask was charged with 2-(4-chlorophenyl)-5-nitropyridine (4.48 g, 14.26 mmol), pinoco boronate (14.48 g, 57.0 mmol), potassium acetate (5.59 g, 57.0 mmol), Pd-(Xphos) (1.404 g, 1.900 mmol), X-phos (1.359 g, 2.85 mmol) and dioxane (50 ml) at room temperature. The flask was sealed, flushed with nitrogen for three times and heated at 115° C. for 72 hours. The mixture was cooled down to room temperature and diluted with dioxane (50 ml) and EtOAc (100 ml), filtered and the filtrate was concentrated. The residue was added dioxane (30 ml) and filtered, the filtrate was purified by flash chromatography (heptanes/acetone 1/2) to afford 5-nitro-2-

(4-(4,4,5,5-tetramethyl-1,3,2-dioxaborolan-2-yl)phenyl)pyridine (3.9 g, 84%) as yellow solid. $^1$H NMR (400 MHz, CHLOROFORM-d) ppm 1.37 (s, 9H) 7.43-8.15 (m, 7H).

Step 3. diethyl 4'-(5-nitropyridin-2-yl)-5,6-dihydro-[1,1'-biphenyl]-4,4(3H)-dicarboxylate

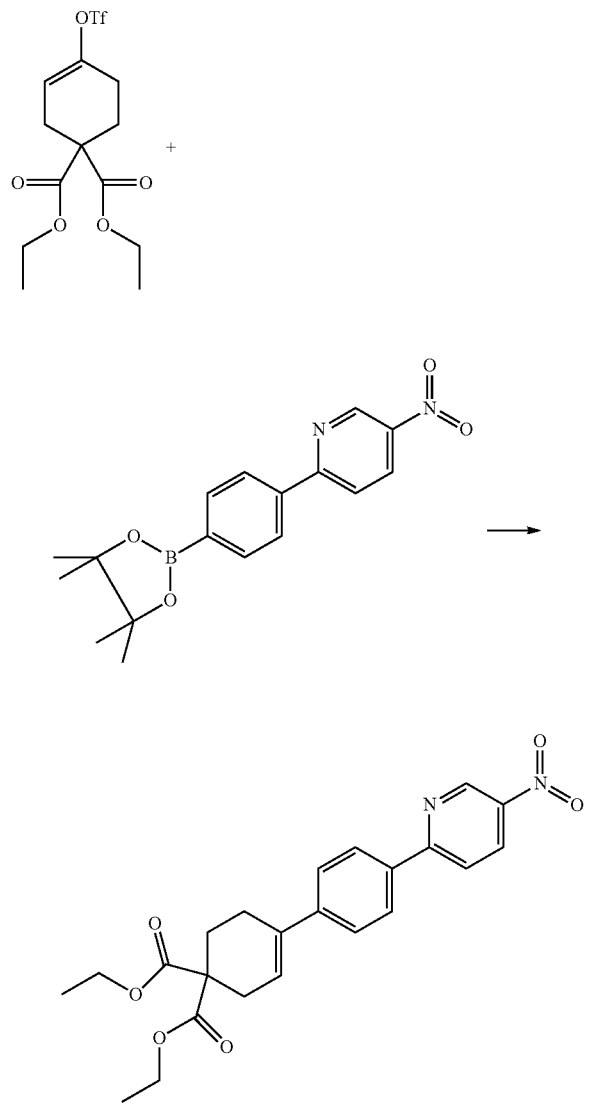

A flask was charged with 5-nitro-2-(4-(4,4,5,5-tetramethyl-1,3,2-dioxaborolan-2-yl)phenyl)pyridine (3.9 g, 10.73 mmol) and potassium carbonate (6.77 g, 48.3 mmol) in dioxane (60 ml) and Water (25 ml), and stirred at room temperature for 10 minutes under nitrogen. Then Pd(PPh$_3$)$_4$ (1.240 g, 1.073 mmol) and diethyl 4-(((trifluoromethyl)sulfonyl)oxy)cyclohex-3-ene-1,1-dicarboxylate (4.22 g, 11.27 mmol) were added to the reaction mixture. The flask was sealed, flushed with nitrogen for three times and heated at 100° C. for 1 hour. The organic solvent was evaporated under vacuum and EtOAc (3×100 ml) was used to extract and the combined organic solvent was washed by saturated aqueous sodium bicarbonate solution, brine, and dried over Na$_2$SO$_4$, then concentrated. The residue was purified by flash chromatography (heptanes/acetone 1/2) to afford diethyl 4'-(5-nitropyridin-2-yl)-5,6-dihydro-[1,1'-biphenyl]-4,4(3H)-dicarboxylate (2.8 g, 61%) as yellow solid. $^1$H NMR (400 MHz, METHANOL-d$_4$) δ ppm 1.25 (t, J=7.20 Hz, 6H) 2.30 (dt, J=6.28, 3.24 Hz, 2H) 2.53 (dd, J=4.67, 1.77 Hz, 2H) 2.76 (dd, J=3.98, 2.08 Hz, 2H) 4.20 (q, J=7.20 Hz, 4H) 6.19 (s, 1H) 7.06-8.88 (m, 7H).

Step 4. (1-(4-(5-aminopyridin-2-yl)phenyl)-6-bromo-2-oxabicyclo[2.2.2]octan-4-yl)methanol

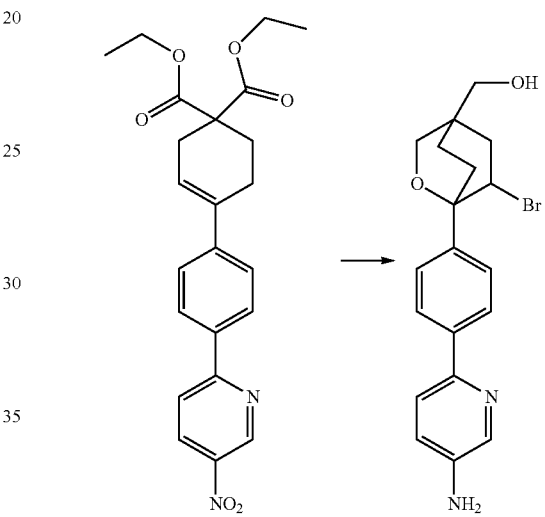

An oven-dried flask under nitrogen charged with diethyl 4'-(5-nitropyridin-2-yl)-5,6-dihydro-[1,1'-biphenyl]-4,4(3H)-dicarboxylate (1.3 g, 3.06 mmol) in tetrahydrofuran (60 ml), was added lithium alumina hydride (15.31 ml, 15.31 mmol) in one portion at 0° C. The mixture was allowed to warm to room temperature and stirred for 2 hours. The reaction was quenched with saturated aqueous sodium chloride solution at 0° C. The mixture was extracted with EtOAc (2×150 ml), and the combined organic phase was dried over Na$_2$SO$_4$, and concentrated to afford the crude intermediate, which was carried to the next step without further purification.

To a stirred solution of crude intermediate from last step in tetrahydrofuran (100 ml) at −78° C., was added N-bromosuccinimide (0.534 g, 3.00 mmol) in dichloromethane (50 ml). The reaction mixture was stirred at room temperature for overnight. The mixture was concentrated and the residue was purified by flash chromatography (heptanes/acetone 1/2) to afford (1-(4-(5-aminopyridin-2-yl)phenyl)-6-bromo-2-oxabicyclo[2.2.2]octan-4-yl)methanol (0.24 g, 21%) as yellow solid. $^1$H NMR (400 MHz, METHANOL-d$_4$) δ ppm 2.03-2.10 (m, 2H) 2.13-2.19 (m, 2H) 2.41-2.53 (m, 2H) 3.45-3.59 (m, 4H) 6.07-6.24 (m, 1H) 7.48 (d, J=8.59 Hz, 2H) 7.77 (d, J=8.72 Hz, 1H) 7.84 (d, J=8.46 Hz, 2H) 8.13 (dd, J=8.72, 2.53 Hz, 1H) 8.74 (d, J=2.27 Hz, 1H). LC/MS, not ionized; RT: 0.84; (Condition E).

Step 5. Synthesis of (1-(4-(5-aminopyridin-2-yl)phenyl)-2-oxabicyclo[2.2.2]octan-4-yl)methanol

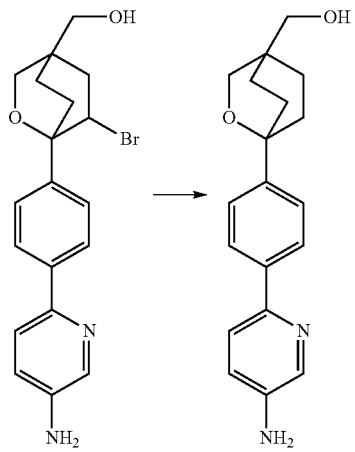 [SMILES: Nc1ccc(-c2ccc(C34CCC(CO)(CO3)CC4Br)cc2)nc1 ; Nc1ccc(-c2ccc(C34CCC(CO)(CC3)CO4)cc2)nc1]

To a stirred solution of (1-(4-(5-aminopyridin-2-yl)phenyl)-6-bromo-2-oxabicyclo[2.2.2]octan-4-yl)methanol (240 mg, 0.617 mmol) in toluene (8 ml) and tetrahydrofuran (8 ml) at 40° C. in a microwave vial under nitrogen, was added the mixture of AIBN (40.5 mg, 0.247 mmol) and Bu$_3$SnH (0.980 ml, 3.70 mmol) in toluene at 40° C. The reaction mixture was heated at 100° C. for 3 hours. Most of solvent was removed by evaporation under vacuum, and the residue was purified by chromotography (heptanes/acetone 1/2) to afford (1-(4-(5-aminopyridin-2-yl)phenyl)-2-oxabicyclo[2.2.2]octan-4-yl)methanol (60 mg, 31%) as yellow solid. LC/MS, [MS+1] 311.1, RT: 0.80; (Condition E).

Step 6. (1-(4-(5-((5-cyclobutyl-1,3,4-oxadiazol-2-yl)amino)pyridin-2-yl)phenyl)-2-oxabicyclo[2.2.2]octan-4-yl)methanol

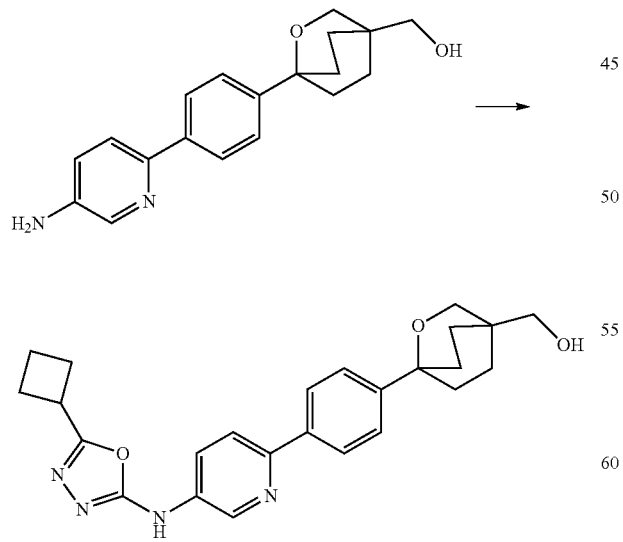

To a solution of (1-(4-(5-aminopyridin-2-yl)phenyl)-2-oxabicyclo[2.2.2]octan-4-yl)methanol (50 mg, 0.161 mmol) in dichloromethane (2 ml) and tetrahydrofuran (1 ml) at room temperature, was added 1,1'-thiocarbonyldipyridin-2(1H)-one (41.2 mg, 0.177 mmol). The mixture was stirred at room temperature for 1 hour.

Cyclobutanecarbohydrazide (0.028 g, 0.242 mmol) in dichloromethane (4 ml) was added to the reaction mixture. The mixture was stirred at room temperature for 1 hour, and EDC.HCl (0.093 g, 0.483 mmol) was added. The mixture was stirred at room temperature for 16 hours. The reaction mixture was diluted with dichloromethane (30 ml) and was filtered to give 1-(4-(5-((5-cyclobutyl-1,3,4-oxadiazol-2-yl)amino)pyridin-2-yl)phenyl)-2-oxabicyclo[2.2.2]octan-4-yl)methanol (30 mg, 43%) as white solid. $^1$H NMR (400 MHz, METHANOL-d$_4$) δ ppm 1.56-2.53 (m, 14H) 3.63-3.78 (m, 2H) 3.94 (s, 2H) 4.10 (d, J=7.07 Hz, 1H) 7.42-7.57 (m, 2H) 7.78-7.92 (m, 3H) 8.15 (dd, J=8.72, 2.78 Hz, 1H) 8.71 (dd, J=2.72, 0.57 Hz, 1H). LC/MS, [MS+1] 433.1, RT: 1.11; (Condition E).

Step 7. 1-(4-(5-((5-cyclobutyl-1,3,4-oxadiazol-2-yl)amino)pyridin-2-yl)phenyl)-2-oxabicyclo[2.2.2]octane-4-carbaldehyde

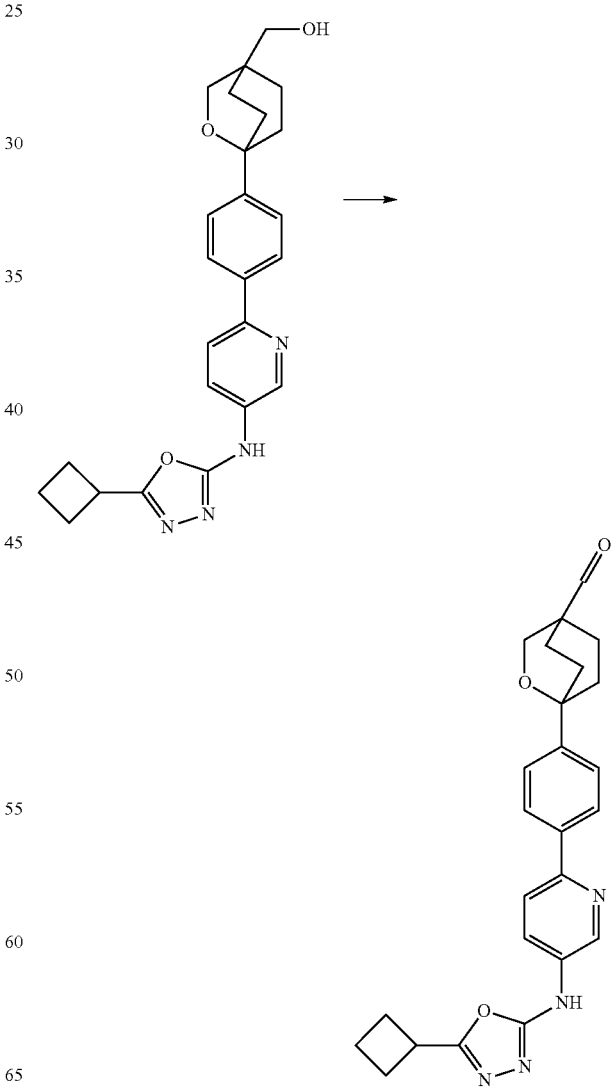

To a stirred solution of 1-(4-(5-((5-cyclobutyl-1,3,4-oxadiazol-2-yl)amino)pyridin-2-yl)phenyl)-2-oxabicyclo[2.2.2]octan-4-yl)methanol (35 mg, 0.081 mmol) in dichloromethane (1 ml) and DMSO (0.5 ml) at 0° C., was added diisopropylethylamine (0.057 ml, 0.324 mmol) and Py.SO$_3$ (25.8 mg, 0.162 mmol). The reaction mixture was stirred at room temperature for 2 hours. The reaction mixture was purified by flash chromatography (heptanes/acetone 1/1) to afford 1-(4-(5-((5-cyclobutyl-1,3,4-oxadiazol-2-yl)amino)pyridin-2-yl)phenyl)-2-oxabicyclo[2.2.2]octane-4-carbaldehyde (30 mg, 86%) as yellow solid. $^1$H NMR (400 MHz, CHLOROFORM-d) δ ppm 1.83-2.56 (m, 14H) 3.56-3.74 (m, 1H) 4.15 (s, 2H) 7.50 (d, J=8.46 Hz, 2H) 7.77 (d, J=8.59 Hz, 1H) 7.94 (d, J=8.46 Hz, 2H) 8.16-8.37 (m, 1H) 8.56-8.72 (m, 1H) 9.55 (s, 1H). LC/MS, [MS+1] 431.1, RT: 1.24; (Condition E).

Step 8. 5-cyclobutyl-N-(6-(4-(4-(2-methoxyvinyl)-2-oxabicyclo[2.2.2]octan-1-yl)phenyl)pyridin-3-yl)-1,3,4-oxadiazol-2-amine ran (1 ml) was flushed with nitrogen for three times and at 0° C., and was added LiHMDS (0.079 ml, 0.084 mmol). The reddish solution was stirred at 0° C. for 30 minutes, and then at −78° C., a solution of 1-(4-(5-((5-cyclobutyl-1,3,4-oxadiazol-2-yl)amino)pyridin-2-yl)phenyl)-2-oxabicyclo[2.2.2]octane-4-carbaldehyde (30 mg, 0.070 mmol) in tetrahydrofuran (0.7 ml) was added dropwise. The mixture was allowed to warm to 0° C. for 30 minutes. The reaction was quenched with water (2 ml), and the mixture was partitioned between brine (15 ml) and ethyl acetate (50 ml), aquous layer was extracted with ethyl acetate (2×50 ml). The combined organic extracts were washed with brine and dried over Na$_2$SO$_4$, and concentrated. The residue was purified by flash chromatography (heptanes/acetone 1/1) to afford 5-cyclobutyl-N-(6-(4-(4-(2-methoxyvinyl)-2-oxabicyclo[2.2.2]octan-1-yl)phenyl)pyridin-3-yl)-1,3,4-oxadiazol-2-amine (10 mg, 31%) as yellow solid. $^1$H NMR (400 MHz, METHANOL-d$_4$) δ ppm 1.83-2.51 (m, 14H) 3.56 (s, 3H) 3.63-3.76 (m, 1H) 4.00 (d, J=6.80 Hz, 1H) 4.06 (s, 2H) 5.87 (d, J=6.80 Hz, 1H) 7.49 (d, J=8.72 Hz, 2H) 7.78-7.93 (m, 3H) 8.17 (dd, J=24.00, 8.80 Hz, 1H) 8.71 (d, J=16.80 Hz, 1H). LC/MS, [MS+1] 459.1, RT: 1.44, 1.48; (Condition E).

Step 9. Synthesis of (1-{4-[5-(5-cyclobutyl-[1,3,4]oxadiazol-2-ylamino)-pyridin-2-yl]-phenyl}-2-oxabicyclo[2.2.2]oct-4-yl)-acetic acid

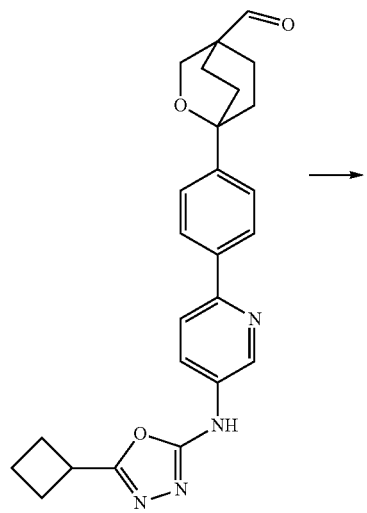

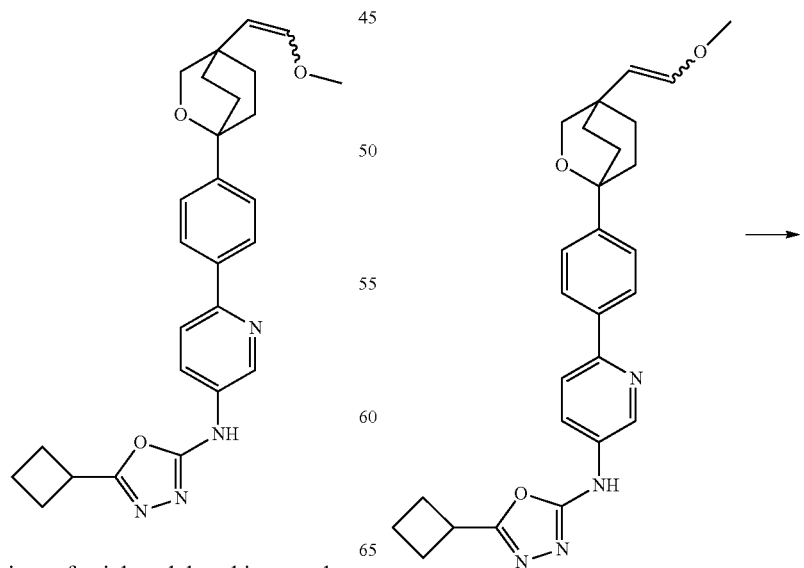

To a stirred suspension of triphenylphosphine methoxymethane chloride (28.7 mg, 0.084 mmol) in tetahydrofu- -continued

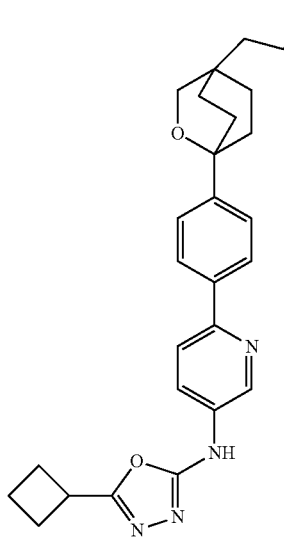

To a stirred solution of 5-cyclobutyl-N-(6-(4-(4-(2-methoxyvinyl)-2-oxabicyclo[2.2.2]octan-1-yl)phenyl)pyridin-3-yl)-1,3,4-oxadiazol-2-amine (10 mg, 0.022 mmol) in tetrahydrofuran (1 ml) at room temperature, was added 1N aqueous HCl solution (0.436 ml, 0.436 mmol). The reaction mixture was stirred for 1 h at room temperature. Most of solvent was removed by evaporation under vacuum, and the residue was purified by flash chromotography to afford 2-(1-(4-(5-((5-cyclobutyl-1,3,4-oxadiazol-2-yl)amino)pyridin-2-yl)phenyl)-2-oxabicyclo[2.2.2]octan-4-yl)acetaldehyde intermediate.

To a stirred solution of the intermediate from last step and 2-methyl-2-butene (0.112 ml, 0.225 mmol) in t-butanol (1 ml), water (0.3 ml), tetrahydrofuran (1.000 ml) cooling with ice-cold bath, was added NaClO$_2$ (3.31 mg, 0.029 mmol). The reaction mixture was stirred for 1 hour at room temperature. The mixture was filtered and the filtrate was purified by HPLC (0.1% NH$_4$OH, 15-100% acetonitrile/water) to afford (1-{4-[5-(5-cyclobutyl-[1,3,4]oxadiazol-2-ylamino)-pyridin-2-yl]-phenyl}-2-oxa-bicyclo[2.2.2]oct-4-yl)-acetic acid (5 mg, 43%) as white solid. $^1$H NMR (400 MHz, METHANOL-d$_4$) δ ppm 1.26-1.38 (m, 3H) 1.81-1.92 (m, 4H) 1.97-2.08 (m, 3H) 2.10 (s, 2H) 2.11-2.22 (m, 4H) 3.68-3.75 (m, 1H) 4.00 (s, 2H) 7.50 (d, J=8.40 Hz, 2H) 7.80-7.89 (m, 3H) 8.16 (dd, J=9.60, 2.80 Hz, 1H) 8.71 (dd, J=2.80, 0.60 Hz, 1H). LC/MS, [MS+] 460.21, RT: 2.45 (Condition M).

EXAMPLE 22

2-(4-(4'-((5-(tert-butyl)-1,3,4-oxadiazol-2-yl)amino)-[1,1'-biphenyl]-4-yl)-7-oxabicyclo[2.2.1]heptan-1-yl) acetic acid Step 1. Synthesis of 8-(4-bromophenyl)-1,4-dioxaspiro[4.5]decan-8-ol

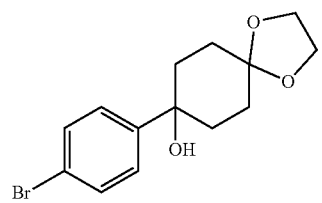 [SMILES: OC1(c2ccc(Br)cc2)CCC2(CC1)OCCO2]

To a flask charged with dry, freshly ground magnesium turnings (187 mg, 7.7 mmol) and I$_2$ (81 mg, 0.32 mmol) in THF (10 mL) was added a solution of 1,4-dibromobenzene (1.81 g, 7.7 mmol) in THF (10 mL) slowly. The resulting mixture was stirred at rt for 30 min. The resultant pale yellow Grignard solution was cooled to −78° C. and to it was added a solution of 1,4-dioxaspiro[4.5]decan-8-one (1 g, 6.4 mmol) in THF (10 mL) slowly dropwise. The reaction was stirred at −78° C. for 20 min before being allowed to stir and warm to rt for 15 hr. The reaction was quenched with a saturated aqueous NH$_4$Cl solution and extracted with methyl tert-butyl ether. The organic phase was washed with a saturated aqueous NaCl solution, dried over MgSO$_4$, filtered and concentrated by rotary evaporation in vacuo to afford 2.2 g of crude orange oil. Purification of the crude material by column chromatography (50 g silica gel, 0-50% EtOAc:Hept, monitor for 225 nm) afforded 0.99 g of the title compound as a white solid.

$^1$H NMR (400 MHz, DMSO-d$_6$): δ ppm 1.47-1.58 (m, 2H), 1.58-1.70 (m, 2H), 1.82-2.02 (m, 4H), 3.88 (s, 4H), 4.99 (s, 1H), 7.40 (d, J=8.6 Hz, 2H), 7.49 (d, J=8.6 Hz, 2H). ESI-MS m/z: not ionized [M+H]$^+$, retention time 1.29 min (condition E).

Step 2. Synthesis of 4-(4-bromophenyl)-4-hydroxycyclohexanone

To a mixture of 8-(4-bromophenyl)-1,4-dioxaspiro[4.5]decan-8-ol (0.99 g, 3.2 mmol) in acetone (10 mL) and water (5 mL) was added Ts-OH (12 mg, 0.063 mmol) and the reaction was let stir in at 75° C. oil bath for 1 hr. The resulting reaction mixture was cooled to rt and the acetone was removed by rotary evaporation in vacuo. The resulting aqueous mixture was extracted with ethyl acetate. The organic phase was dried over MgSO$_4$, filtered and concentrated by rotary evaporation in vacuo to afford 0.9 g of a crude pale yellow solid which was used without further purification. $^1$H NMR (400 MHz, DMSO-$d_6$): δ ppm 1.84-1.98 (m, 2H), 2.06-2.29 (m, 4H), 2.76 (td, J=13.8, 6.3 Hz, 2H), 5.47 (s, 1H), 7.51 (s, 4H). ESI-MS m/z: not ionized [M+H]$^+$, retention time 1.18 min (condition E).

Step 3. Synthesis of methyl 2-(4-(4-bromophenyl)-4-hydroxycyclohexylidene)acetate

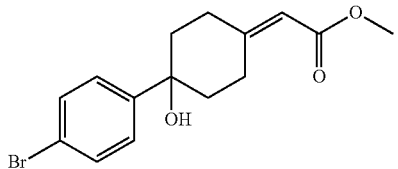 [SMILES: COC(=O)C=C1CCC(O)(c2ccc(Br)cc2)CC1]

To a solution of NaH (60% dispersion in mineral oil, 70 mg, 1.7 mmol) in methanol (6.7 mL) was added trimethylphosphonoacetate (0.23 mL, 1.6 mmol) and the reaction was let stir at rt for 30 min. To the reaction was added 4-(4-bromophenyl)-4-hydroxycyclohexanone (360 mg, 1.3 mmol) and the reaction was let stir at rt for 20 h. The resulting reaction mixture was quenched with saturated aqueous ammonium chloride solution and extracted with ethyl acetate. The organic phase was dried over MgSO$_4$, filtered and concentrated by rotary evaporation in vacuo to afford 530 mg of a crude opaque oil. Purification of the crude material by column chromatography (25 g silica gel, 0-60% EtOAc:Hept, monitor 230 nm) afforded 51 mg (12%) of methyl 2-(4-(4-bromophenyl)-7-oxabicyclo[2.2.1]heptan-1-yl)acetate as a colorless oil (ESI-MS m/z: 327.1 [M+H]$^+$, retention time 1.56 min (condition E)) and 275 mg (63%) of the title compound as a colorless oil (ESI-MS m/z: n/a [M+H]$^+$, retention time 1.42 min (condition E)). $^1$H NMR (400 MHz, DMSO-$d_6$): δ ppm 1.71-1.93 (m, 4H), 2.19 (d, J=13.1 Hz, 1H), 2.29-2.44 (m, 1H), 2.66 (td, J=12.6, 4.7 Hz, 1H), 3.56-3.69 (m, 4H), 5.24 (s, 1H), 5.72 (s, 1H), 7.41-7.52 (m, 4H). $^{13}$C NMR (100 MHz, DMSO-$d_6$): δ ppm 166.1, 162.5, 148.7, 130.6, 127.1, 119.3, 112.6, 70.8, 50.6, 38.7, 32.4, 24.5.

Step 4. Synthesis of methyl 2-(4-(4-bromophenyl)-7-oxabicyclo[2.2.1]heptan-1-yl)acetate

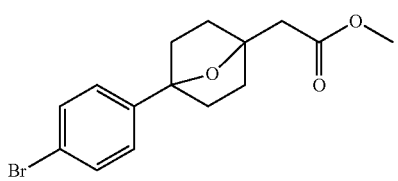 [SMILES: COC(=O)CC12CCC(c3ccc(Br)cc3)(CC1)O2]

To a solution of methyl 2-(4-(4-bromophenyl)-4-hydroxycyclohexylidene)acetate (190 mg, 0.58 mmol) in acetonitrile (7 mL) was added Cs$_2$CO$_3$ (381 mg, 1.17 mmol) and the reaction was let stir in a 50° C. oil bath for 24 h. The resulting reaction mixture was diluted with ethyl acetate and washed with water, followed by a saturated aqueous NaCl solution. The organic phase was dried over MgSO$_4$, filtered and concentrated by rotary evaporation in vacuo to afford 188 mg of crude orange film. The crude material was purified by column chromatography (24 g silica gel, 0-40% EtOAc:Hept, monitor 230 nm) to afford 64 mg (34%) of the title compound as a colorless film that solidified upon standing. $^1$H NMR (400 MHz, DMSO-$d_6$): δ ppm 1.56-1.81 (m, 4H), 1.85-1.97 (m, 2H), 2.14 (td, J=9.9, 3.9 Hz, 2H), 2.92 (s, 2H), 3.63 (s, 3H), 7.32 (d, J=8.6 Hz, 2H), 7.53 (d, J=8.6 Hz, 2H). $^{13}$C NMR (100 MHz, DMSO-$d_6$): δ ppm 170.3, 142.0, 130.9, 127.1, 119.8, 86.0, 83.2, 51.3, 37.6, 35.4 (additional signal likely hidden under DMSO solvent signal). ESI-MS m/z: 327.0 [M+H]$^+$, retention time 1.55 min (condition E).

Step 5. Synthesis of methyl 2-(4-(4'-((5-(tert-butyl)-1,3,4-oxadiazol-2-yl)amino)-[1,1'-biphenyl]-4-yl)-7-oxabicyclo[2.2.1]heptan-1-yl)acetate

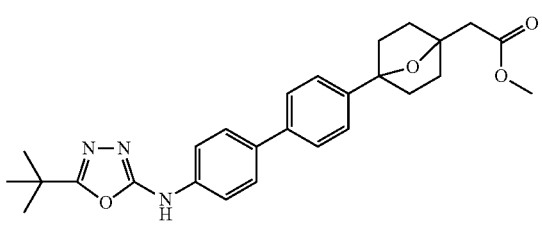 [SMILES: COC(=O)CC12CCC(c3ccc(-c4ccc(Nc5nnc(C(C)(C)C)o5)cc4)cc3)(CC1)O2]

To a flask charged with methyl 2-(4-(4-bromophenyl)-7-oxabicyclo[2.2.1]heptan-1-yl)acetate (106 mg, 0.33 mmol), 5-(tert-butyl)-N-(4-(4,4,5,5-tetramethyl-1,3,2-dioxaborolan-2-yl)phenyl)-1,3,4-oxadiazol-2-amine (117 mg, 0.34 mmol), Pd(amphos)Cl$_2$ (23 mg, 0.033 mmol) and CsF (150 mg, 0.98 mmol) under N$_2$ was added 1,4-dioxane (2.9 mL) and water (0.33 mL). The mixture was sparged with N$_2$ for 10 min and set to stir in a 90° C. oil bath for 2 hr. The reaction mixture was diluted with ethyl acetate, washed with a saturated aqueous NaHCO$_3$ solution, then water, followed by a saturated aqueous NaCl solution. The organic phase was dried over MgSO$_4$, filtered and concentrated by rotary evaporation in vacuo to afford 210 mg crude orange solid. The crude material was triturated with warm acetonitrile to afford 113 mg of the title compound as a white solid which was used without further purification. $^1$H NMR (400 MHz, DMSO-$d_6$) δ ppm 1.36 (s, 9H), 1.66-1.83 (m, 4H), 1.88-2.00 (m, 2H), 2.10-2.21 (m, 2H), 2.94 (s, 2H), 3.64 (s, 3H), 7.42 (d, J=8.6 Hz, 2H), 7.55-7.71 (m, 6H), 10.52 (s, 1H). ESI-MS m/z: 462.1 [M+H]$^+$, retention time 1.51 min (condition E).

Step 6. Synthesis of 2-(4-(4'-((5-(tert-butyl)-1,3,4-oxadiazol-2-yl)amino)-[1,1'-biphenyl]-4-yl)-7-oxabicyclo[2.2.1]heptan-1-yl)acetic acid

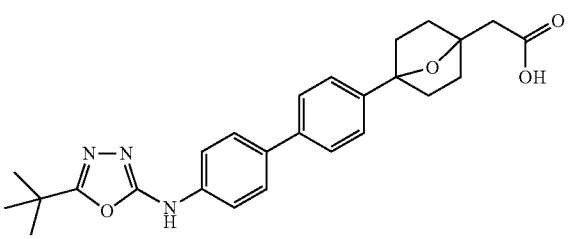 [SMILES: CC(C)(C)c1nnc(Nc2ccc(-c3ccc(C45CCC(CC(=O)O)(CC4)O5)cc3)cc2)o1]

To a solution of methyl 2-(4-(4'-((5-(tert-butyl)-1,3,4-oxadiazol-2-yl)amino)-[1,1'-biphenyl]-4-yl)-7-oxabicyclo [2.2.1]heptan-1-yl)acetate (110 mg, 0.24 mmol) in THF (4 mL) and Methanol (1 mL) was added 1N NaOH (0.72 mL, 0.72 mmol) and the reaction was let stir at rt for 2 hr. The resulting yellow reaction mixture was partially concentrated by rotary evaporation in vacuo (rt water bath). The yellow solution was diluted with MeOH, filtered and purified on preparative HPLC (10-50% MeCN:5 mM NH$_4$OH) to afford 52 mg (49%) of the title compound as a white solid. $^1$H NMR (400 MHz, DMSO-d$_6$): δ ppm 1.36 (s, 9H), 1.63-1.82 (m, 4H), 1.90-2.02 (m, 2H), 2.08-2.21 (m, 2H), 2.79 (s, 2H), 7.42 (d, J=8.3 Hz, 2H), 7.56-7.70 (m, 6H), 10.51 (br. s., 1H). ESI-MS m/z: 448.1 [M+H]$^+$, retention time 1.08 min (condition E). HR/MS [M+H]$^+$: found 448.2236. calc. 448.2218. RT: 2.27 (Condition L).

EXAMPLE 23

3-(4-(4'-((5-(tert-butyl)-1,3,4-oxadiazol-2-yl)amino)-[1,1'-biphenyl]-4-yl)-7-oxabicyclo[2.2.1]heptan-1-yl) propanoic acid

Step 1. Synthesis of 4-methylenecyclohexanone

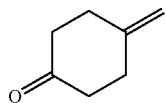

To a solution of methyl triphenylphosphonium bromide (13.7 g, 38 mmol) in 1,4-dioxane (60 mL) was added potassium tert-butoxide (4.3 g, 38 mmol). The resulting yellow mixture was cooled to 0° C. in an ice-water bath and 1,4-dioxaspiro[4.5]decan-8-one (5 g, 32 mmol) was added slowly over 15 min as a solution in 1,4-dioxane (15 mL) via dropping funnel. The reaction was let stir and warm to rt over 1 h. The resulting brown-yellow reaction mixture was partitioned between methyl tert-butyl ether and saturated aqueous NH$_4$Cl solution. The aqueous phase was extracted with methyl tert-butyl ether. The combined organic phases were washed with a saturated aqueous NaCl solution, dried over MgSO$_4$, filtered and concentrated by rotary evaporation in vacuo to ~20 mL. The resultant beige suspension was diluted with heptane and filtered. The filtrated was concentrated by rotary evaporation in vacuo to afford ~7 g of crude 8-methylene-1,4-dioxaspiro[4.5]decane as a yellow liquid containing residual heptane.

The crude liquid was taken up in acetone (15 mL) and water (15 mL) and to this was added toluenesulfonic acid (5 mg). The reaction was let stir at 50° C. for 8 h. The resulting yellow reaction mixture was concentrated to ~20 mL by rotary evaporation in vacuo and partitioned between methyl tert-butyl ether and saturated aqueous NH$_4$Cl solution. The aqueous phase was extracted with methyl tert-butyl ether. The combined organic phases were washed with a saturated aqueous NaCl solution, dried over MgSO$_4$, filtered and concentrated to ~5 mL by rotary evaporation in vacuo to afford ~5 g of yellow liquid that was used without further purification.

Step 2. Synthesis of 1-(4-bromophenyl)-4-methylenecyclohexanol

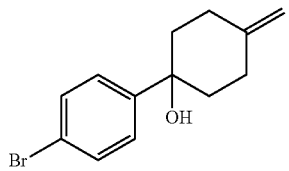

To a flask charged with dry, freshly ground magnesium turnings (1.1 g, 45 mmol) and iodine (25 mg, 0.1 mmol) in THF (50 mL) was added a solution of 1,4-dibromobenzene (10.6 g, 45.0 mmol) in THF (30 mL) slowly by dropping funnel over 30 min. The resulting mixture was stirred at rt for 1 hr. The resultant grey Grignard solution was cooled to −78° C. and to it was added a solution of 4-methylenecyclohexanone (3.3 g, 30 mmol) in THF (20 mL) slowly dropwise over 20 min. The reaction was stirred at −78° C. for 30 min before being allowed to stir and warm to rt for 3 h. The resulting reaction mixture was quenched with a saturated aqueous NH$_4$Cl solution and extracted with methyl tert-butyl ether. The combined organic phases were washed with a saturated aqueous NaCl solution, dried over MgSO$_4$, filtered and concentrated by rotary evaporation in vacuo to afford a crude yellow oil. Purification of the crude material by column chromatography (80 g silica gel, 0-50% EtOAc:Hept, monitor for 225 nm) afforded 2.94 g of a colorless oil that was used without further purification. ESI-MS m/z: not ionized [M+H]$^+$, retention time 1.50 min (condition E).

Step 3. Synthesis of 1-(4-bromophenyl)-4-(iodomethyl)-7-oxabicyclo[2.2.1]heptanes

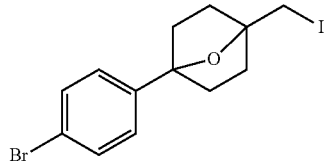 [SMILES: Brc1ccc(C23CCC(CI)(CC2)O3)cc1]

To a suspension of Na$_2$CO$_3$ (0.63 g, 6.0 mmol) in a solution of 1-(4-bromophenyl)-4-methylenecyclohexanol (1.06 g, 4.0 mmol) in acetonitrile (20 mL) was added iodine (2.0 g, 7.9 mmol) portion-wise over 20 min and the reaction was let stir at rt for 4 h. The resulting dark red reaction was diluted with EtOAc, washed sequentially with a saturate aqueous Na$_2$S$_2$O$_3$ solution, water followed by a saturated aqueous NaCl solution. The organic phase was dried over MgSO$_4$, filtered and concentrated by rotary evaporation in vacuo to afford a crude yellow residue. Purification of the crude material by column chromatography (12 g silica gel, 0-30% EtOAc:Hept, monitor 225 nm) afforded 1 g white solid that was used without further purification. $^1$H NMR (400 MHz, DMSO-d$_6$): δ ppm 1.62-1.86 (m, 4H), 1.87-1.98 (m, 2H), 2.17-2.29 (m, 2H), 3.69 (s, 2H), 7.32 (d, J=8.6 Hz, 2H), 7.54

(d, J=8.6 Hz, 2H). ESI-MS m/z: not ionized [M+H]⁺, retention time 1.73 min (condition E).

Step 4. Synthesis of dimethyl 2-((4-(4-bromophenyl)-7-oxabicyclo[2.2.1]heptan-1-yl)methyl)malonate

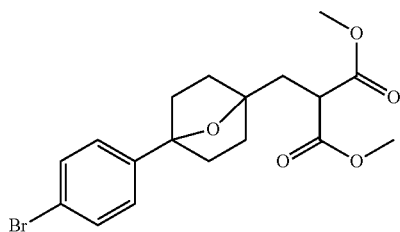 [SMILES: COC(=O)C(CC12CCC(c3ccc(Br)cc3)(CC1)O2)C(=O)OC]

To a solution of dimethyl malonate (0.47 mL, 4.1 mmol) in anhydrous dimethyl acetamide (5.6 mL) cooled in an ice-water bath was added NaH (60% dispersion in mineral oil, 163 mg, 4.1 mmol) portion-wise and the reaction was let stir at rt for 30 min until homogeneous. To this was added 1-(4-bromophenyl)-4-(iodomethyl)-7-oxabicyclo[2.2.1]heptane (440 mg, 1.12 mmol) and the reaction was stirred in a microwave reactor at 150° C. for 45 min. The resulting yellow reaction mixture was quenched with a saturated aqueous NH₄Cl solution and extracted with EtOAc. The organic phase was dried over MgSO₄, filtered and concentrated by rotary evaporation in vacuo to afford a crude yellow oil. Purification of the crude material by column chromatography (40 g silica gel, 0-30% EtOAc:Hept, monitor 225 nm) afforded 108 mg (28%) of methyl 3-(4-(4-bromophenyl)-7-oxabicyclo[2.2.1]heptan-1-yl)propanoate (decarboxylated material) as a clear yellow film and 245 mg (55%) of the title compound as a clear yellow film. ¹H NMR (400 MHz, DMSO-d₆): δ ppm 1.54-1.79 (m, 6H), 2.06-2.16 (m, 2H), 2.39 (d, J=7.1 Hz, 2H), 3.66 (s, 6H), 3.73 (t, J=7.1 Hz, 1H), 7.27 (d, J=8.6 Hz, 2H), 7.54 (d, J=8.6 Hz, 2H). ESI-MS m/z: 399.0 [M+H]⁺, retention time 1.59 min (condition E).

Step 5. Synthesis of methyl 3-(4-(4-bromophenyl)-7-oxabicyclo[2.2.1]heptan-1-yl)propanoate

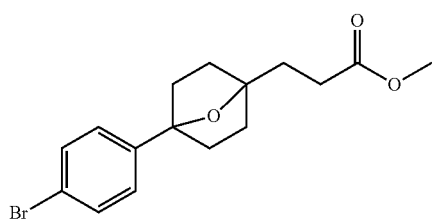 [SMILES: COC(=O)CCC12CCC(c3ccc(Br)cc3)(CC1)O2]

To a solution of dimethyl 2-((4-(4-bromophenyl)-7-oxabicyclo[2.2.1]heptan-1-yl)methyl)malonate (305 mg, 0.77 mmol) in DMSO (3.0 mL) and water (0.03 mL) was added lithium chloride (98 mg, 2.3 mmol) and the reaction was stirred in a microwave reactor at 180° C. for 20 min. The resulting yellow reaction mixture was diluted with water and extracted with EtOAc. The organic phase was dried over MgSO₄, filtered and concentrated by rotary evaporation in vacuo to afford 289 mg of a crude clear yellow film. Purification of the crude material by column chromatography (24 g silica gel, 0-30% EtOAc:Hept, monitor 230 nm) afforded 194 mg colorless film that solidified upon standing and which was used without further purification. ¹H NMR (400 MHz, DMSO-d₆): δ ppm 1.54-1.67 (m, 4H), 1.68-1.79 (m, 2H), 2.04-2.16 (m, 4H), 2.42-2.48 (m, 2H), 3.61 (s, 3H), 7.31 (d, J=8.6 Hz, 2H), 7.53 (d, J=8.6 Hz, 2H). ESI-MS m/z: 341.1 [M+H]⁺, retention time 1.59 min (condition E).

Step 6. Synthesis of methyl 3-(4-(4'-((5-(tert-butyl)-1,3,4-oxadiazol-2-yl)amino)-[1,1'-biphenyl]-4-yl)-7-oxabicyclo[2.2.1]heptan-1-yl)propanoate

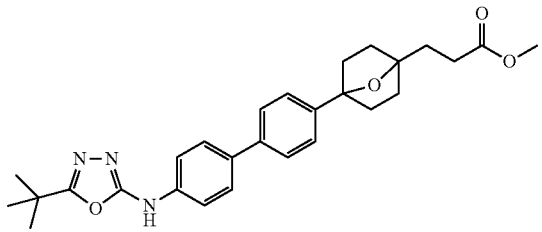 [SMILES: COC(=O)CCC12CCC(c3ccc(-c4ccc(Nc5nnc(C(C)(C)C)o5)cc4)cc3)(CC1)O2]

To a flask charged with methyl 3-(4-(4-bromophenyl)-7-oxabicyclo[2.2.1]heptan-1-yl)propanoate (103 mg, 0.30 mmol), 5-(tert-butyl)-N-(4-(4,4,5,5-tetramethyl-1,3,2-dioxaborolan-2-yl)phenyl)-1,3,4-oxadiazol-2-amine (109 mg, 0.32 mmol), Pd(amphos)Cl₂ (21 mg, 0.030 mmol) and CsF (138 mg, 0.91 mmol) under N₂ was added 1,4-dioxane (2.7 mL) and water (0.30 mL). The mixture was sparged with N₂ for 10 min and stirred in a 90° C. oil bath for 2 h. The resulting reaction mixture was diluted with dichloromethane and washed with a saturated aqueous NaHCO₃ solution. The organic layer was warmed and filtered (no product evident in filtercake). The filtrate was concentrated to afford 200 mg of crude orange solid. The crude material was washed with triturated with acetonitrile and filtered to afford 106 mg of pale orange solid which was used without further purification. ¹H NMR (400 MHz, DMSO-d₆): δ ppm 1.36 (s, 9H), 1.56-1.83 (m, 6H), 2.04-2.20 (m, 4H), 3.62 (s, 3H), 7.42 (d, J=8.6 Hz, 2H), 7.55-7.69 (m, 6H), 10.51 (s, 1H) (additional 2H signal likely hidden under DMSO solvent peak). ESI-MS m/z: 476.0 [M+H]⁺, retention time 1.55 min (condition E).

Step 7. Synthesis of 3-(4-(4'-((5-(tert-butyl)-1,3,4-oxadiazol-2-yl)amino)-[1,1'-biphenyl]-4-yl)-7-oxabicyclo[2.2.1]heptan-1-yl)propanoic acid

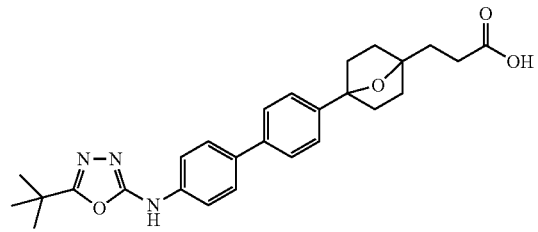 [SMILES: CC(C)(C)c1nnc(Nc2ccc(-c3ccc(C45CCC(CCC(=O)O)(CC4)O5)cc3)cc2)o1]

To a solution of methyl 3-(4-(4'-((5-(tert-butyl)-1,3,4-oxadiazol-2-yl)amino)-[1,1'-biphenyl]-4-yl)-7-oxabicyclo[2.2.1]heptan-1-yl)propanoate (100 mg, 0.21 mmol) in THF (3.4 mL) and methanol (0.85 mL) was added 1N NaOH solution (0.63 mL, 0.63 mmol) and the reaction was let stir at rt for 2 h. The resulting yellow reaction mixture was partially concentrated by rotary revaporation (rt water bath) to remove THF. The resulting yellow mixture was diluted with methanol, filtered and purified on preparative HPLC (10-50% acetonitrile:5 mM NH$_4$OH) and lyophilized to afford 83 mg (86%) of the title compound as a white solid. $^1$H NMR (400 MHz, DMSO-d$_6$): δ ppm 1.36 (s, 9H), 1.56-1.82 (m, 6H), 2.01-2.10 (m, 2H), 2.10-2.19 (m, 2H), 2.30-2.39 (m, 2H), 7.43 (d, J=8.6 Hz, 2H), 7.60 (d, J=8.6 Hz, 2H), 7.62-7.67 (m, 4H) 10.51 (br. s., 1H). $^{13}$C NMR (100 MHz, DMSO-d$_6$): δ ppm 174.5, 165.9, 159.5, 141.7, 138.3, 138.2, 133.1, 127.1, 125.8, 125.4, 117.1, 86.1, 85.5, 37.9, 34.9, 31.7, 30.2, 30.1, 27.8. ESI-MS m/z: 462.1 [M+H]$^+$, retention time 1.13 min (condition E). HR/MS [M+H]$^+$: found 462.2371. calc. 462.2393. RT: 1.96 (Condition L).

Biological Assays

The activity of compounds according to the invention can be assessed by the following inhibition assay.

DGAT1 Inhibition Assay

The enzyme preparation used in this assay is a membrane preparation from Sf9 cells overexpressing human (His)$_6$ DGAT1. During all steps samples were chilled to 4° C. Sf9 cells expressing human (His)$_6$DGAT1 were thawed at room temperature and re-suspended at a 10:1 ratio (mL buffer/g of cells) in 50 mM HEPES, 1× Complete Protease Inhibitor, pH 7.5. The re-suspended pellet was homogenized for 1 min using a Brinkman PT 10/35 homogenizer with a 20 mm generator. Cells were lysed using Avestin Emulsiflex (chilled to 4° C.) at 10000-15000 psi. Lysate was centrifuged at 100,000×g for 1 h at 4° C. Supernatant was removed and pellets were re-suspended in 50 mM HEPES, 1× Complete Protease Inhibitor, pH 7.5 at ⅙ the volume of supernatant. Re-suspended pellets were pooled and homogenized with 10 strokes of a Glas-Col motor driven teflon pestle on setting 70. The protein concentration of the membrane preparation was quantified using BCA protein assay with 1% SDS. The membrane preparation was aliquoted, frozen on dry ice, and stored at −80° C.

For 50 mL, 25 mL of 0.2 M HEPES stock buffer, 0.5 mL of 1 M MgCl$_2$ (5 mM final concentration), and 24.5 mL of milli-Q H$_2$O are added to the 55 mL Wheaton Potter-Elvehjem homogenizer. Enzyme preparation (0.1 mL) is added to buffer and the mixture is homogenized with 5 strokes on ice using the Glas-Col variable speed homogenizer system on setting 70.

For 50 mL, 0.5 mL 10 mM diolein is added to 9.5 mL of EtOH in a 50 mL Falcon screw cap conical centrifuge tube. Five mL of 10 mM sodium acetate pH 4.5 is added followed by 0.5 mL of 10 mM oleoyl-CoA. Finally, the remaining 4.5 mL of 10 mM sodium acetate pH 4.5 is added followed by 30 mL of milli-Q H20. The solution should be gently agitated by hand to induce mixing. The final concentrations of EtOH and sodium acetate are 20% and 2 mM, respectively.

Dry compounds are dissolved in the appropriate volume of DMSO to a final concentration of 10 mM. A 10-point, 3-fold dose response is used to evaluate compound potency. All dilutions are performed in DMSO in a Greiner 384-well microplate.

1. 2 μL of compound in DMSO is added to the appropriate wells. 2 μL of DMSO is added to 100% activity and 100% inhibition controls.
2. 25 μL of enzyme mix is added to all wells and plate(s) are incubated for 10 min at RT.
3. 10 μL of 20% acetic acid quench is added to 100% inhibition control wells. Plate(s) are vortexed using Troemner multi-tube vortexer (setting 7 for 10 sec).
4. 25 μL of substrate mix is added to all wells. Plate(s) are vortexed using Troemner multi-tube vortexer (setting 7 for 10 sec). Plate(s) are incubated for 30 min at RT.
5. 10 μL of 20% acetic acid quench is added to all wells. Plate(s) are vortexed using Troemner multi-tube vortexer (setting 7 for 10 sec).
6. 50 μL of 1-butanol w/ glyceryl tripalmitoleate internal standard is added to all wells.
7. Plate(s) are sealed with super pierce strong plate sealer using the thermo-sealer.
8. Plate(s) are vortexed using Troemner multi-tube vortexer (setting 10 for 5 min).
9. Plate(s) are centrifuged at 162×g (1000 rpm for GH-3.8 rotor) for 5 min using Beckman GS-6R tabletop centrifuge.

Samples were analyzed by LC/MS/MS using a Waters 1525μ LC and Quattro Micro API MS. Where indicated, tripalmitolein was used as an internal standard to control for instrument variation.

HPLC Conditions:

Column: Thermo Betabasic 4, 2.1×20 mm

Solvent: 10 mM Ammonium Formate, 0.1% Formic Acid, 2% water, 98% Methanol

Isocratic run 0.5 ml per minute

Run time 1 minute

Data is converted to % inhibition prior to curve fitting using the following equation:

$$\% \text{ Inhibition} = \frac{(\text{response compound} - \text{response 100\% inhibition control})}{(\text{response 100\% activity control} - \text{response 100\% inhibition control})} \times 100$$

Using the method described above, the compounds of the present invention were shown to possess inhibitory activity with IC$_{50}$ values ranging from 0.001 μM to 100 μM.

Cellular Assay to Measure Activity of DGAT1 Inhibitors in Mammalian Cells.

C2C12 cells are an immortal mouse skeletal muscle cell line showing an 8-fold enrichment form DGAT1 versus DGAT2. C2C12 cells were routinely cultured in 150 cm2 flasks with DMEM (25 mM glucose) containing 10% FBS, 4 m M L-glutamine, 100 U/ml penicillin and 100 μg/ml streptomycin (30 ml per flask), at 37° C., 5% CO2 and 95% humidity. All studies were performed on cells at passage 10 or less.

C2C12 cells were seeded in 96-well plates in DMEM containing 4.5 mM glucose and 10% FBS, 18 h (at 37° C.) prior to assay (all wells of the plate are used). Following 18 h incubation, seeding medium was then replaced with DMEM (5 mM glucose) containing 250 μM oleate (complexed to BSA) and compounds or DMSO, for 2 h (at 37° C.). Compounds were added at 1:3 dilution, 11 points and DMSO control, the starting concentration was usually 40 μM. Each point was dosed in quadruplicate allowing 2 compounds to be dosed per plate. The medium was removed at the end of the incubation and 200 μl/well of 1-butanol added. The 1-butanol contained an internal standard, tripalmitolein (2 μM). The plates were sealed with an adhesive plate sealer and left at room temperature for at least 30 min, then spun down at 209×g for 5 min.

Butanolic extracts were transferred to 384-well LC-MS plates (80 μl/well) and the plate heatsealed with a foil plate sealer. The 384-well plates containing sample were spun down at 209×g for 5 min prior to loading on the LC-MS.

Samples were analyzed by LC/MS using a Waters 1525μ LC and Quattro Micro API MS.

Where indicated, tripalmitolein was used as an internal standard to control for instrument variation. HPLC conditions as above.

Table 1 below shows the inhibitory activity ($IC_{50}$ values) of representative compounds to human DGAT1.

TABLE 1

Activities of compounds of the invention in the DGAT1 assay

| Example | Name | DGAT1 $IC_{50}$ (μM) | DGAT1-C2C12 $IC_{50}$ (μM) |
|---|---|---|---|
| 1 | 2-(4-(4-(5-(5-tert-butyl-1,3,4-oxadiazol-2-ylamino)pyridin-2-yl)phenyl)-2-oxabicyclo[2.2.2]octan-1-yl)acetic acid | 0.345 | 0.288 |
| 2 | 2-(4-(4-(5-((5-cyclobutyl-1,3,4-oxadiazol-2-yl)amino)pyridin-2-yl)phenyl)-2-oxabicyclo[2.2.2]octan-1-yl)acetic acid | 0.12 | 0.4125 |
| 3 | 2-(4-(4-(5-((5-cyclobutyl-1,3,4-thiadiazol-2-yl)amino)pyridin-2-yl)phenyl)-2-oxabicyclo[2.2.2]octan-1-yl)acetic acid | 0.0535 | 0.015 |
| 4 | 2-(4-(4-(2-(5-cyclobutyl-1,3,4-thiadiazol-2-ylamino)pyrimidin-5-yl)phenyl)-2-oxabicyclo[2.2.2]octan-1-yl)acetic acid | 14 | 2.5 |
| 5 | 2-(4-(4-(6-((5-cyclobutyl-1,3,4-thiadiazol-2-yl)amino)pyridin-3-yl)phenyl)-2-oxabicyclo[2.2.2]octan-1-yl)acetic acid | 0.375 | 1.24 |
| 6 | 2-(4-(4'-(5-cyclobutyl-1,3,4-thiadiazol-2-ylamino)biphenyl-4-yl)-2-oxabicyclo[2.2.2]octan-1-yl)acetic acid | 0.0125 | 0.002 |
| 7 | 2-(4-(4'-(5-cyclobutyl-1,3,4-oxadiazol-2-ylamino)biphenyl-4-yl)-2-oxabicyclo[2.2.2]octan-1-yl)acetic acid | 0.0902 | 0.016 |
| 8 | 2-(4-(4'-(5-tert-butyl-1,3,4-oxadiazol-2-ylamino)biphenyl-4-yl)-2-oxabicyclo[2.2.2]octan-1-yl)acetic acid | 0.099 | 0.009 |
| 9 | 2-(4-(4'-((5-cyclopropyl-1,3,4-oxadiazol-2-yl)amino)-[1,1'-biphenyl]-4-yl)-2-oxabicyclo[2.2.2]octan-1-yl)acetic acid | 230 | 528 |
| 10 | 2-(4-(4'-(2-ethyl-N,4-dimethyloxazole-5-carboxamido)-[1,1'-biphenyl]-4-yl)-2-oxabicyclo[2.2.2]octan-1-yl)acetic acid | 0.36 | 0.056 |
| 11 | 2-(4-(4'-(2-Ethyl-4-methyloxazole-5-carboxamido)biphenyl-4-yl)-2-oxabicyclo[2.2.2]octan-1-yl)acetic acid | 0.93 | 0.056 |
| 12 | 2-(4-(4-(5-(2-methyl-5-(trifluoromethyl)oxazole-4-carboxamido)pyridin-2-yl)phenyl)-2-oxabicyclo[2.2.2]octan-1-yl)acetic acid | 0.8775 | NA |
| 13 | 2-(4-(4-(5-(2-ethyl-4-methyloxazole-5-carboxamido)pyridin-2-yl)phenyl)-2-oxabicyclo[2.2.2]octan-1-yl)acetic acid | 0.68 | 0.098 |
| 14 | 2-(4-(4-(5-((5-(tert-butyl)oxazol-2-yl)amino)pyridin-2-yl)phenyl)-2-oxabicyclo[2.2.2]octan-1-yl)acetic acid | 0.13 | 0.108 |
| 15 | 2-(4-(4'-((5-(tert-butyl)oxazol-2-yl)amino)-[1,1'-biphenyl]-4-yl)-2-oxabicyclo[2.2.2]octan-1-yl)acetic acid | 0.044 | 0.007 |
| 16 | 2-(4-(4'-((5-isobutyl-1,3,4-oxadiazol-2-yl)amino)-[1,1'-biphenyl]-4-yl)-2-oxabicyclo[2.2.2]octan-1-yl)acetic acid | 0.06 | 0.038 |
| 17 | 2-(4-(4'-((5-neopentyl-1,3,4-oxadiazol-2-yl)amino)-[1,1'-biphenyl]-4-yl)-2-oxabicyclo[2.2.2]octan-1-yl)acetic acid | 0.053 | 0.031 |
| 18 | 2-(1-(4'-(2-ethyl-5-methyloxazole-4-carboxamido)-[1,1'-biphenyl]-4-yl)-2-oxabicyclo[2.2.2]octan-4-yl)acetic acid | 2.9 | 0.16 |
| 19 | 2-(1-(4'-((5-cyclobutyl-1,3,4-oxadiazol-2-yl)amino)-[1,1'-biphenyl]-4-yl)-2-oxabicyclo[2.2.2]octan-4-yl)acetic acid | 0.26 | 0.006 |
| 20 | 2-(1-(4'-((5-(tert-butyl)-1,3,4-oxadiazol-2-yl)amino)-[1,1'-biphenyl]-4-yl)-2-oxabicyclo[2.2.2]octan-4-yl)acetic acid | 0.12 | 0.016 |
| 21 | 2-(1-(4-(5-((5-cyclobutyl-1,3,4-oxadiazol-2-yl)amino)pyridin-2-yl)phenyl)-2-oxabicyclo[2.2.2]octan-4-yl)acetic acid | 0.36 | 0.944 |
| 22 | 2-(4-(4'-((5-(tert-butyl)-1,3,4-oxadiazol-2-yl)amino)-[1,1'-biphenyl]-4-yl)-7-oxabicyclo[2.2.1]heptan-1-yl)acetic acid | 1.7 | 0.296 |
| 23 | 3-(4-(4'-((5-(tert-butyl)-1,3,4-oxadiazol-2-yl)amino)-[1,1'-biphenyl]-4-yl)-7-oxabicyclo[2.2.1]heptan-1-yl)propanoic acid | 0.084 | 0.267 |

Conclusions

It can be seen that the compounds of the invention are useful as inhibitors of DGAT1 and therefore useful in the treatment of diseases and conditions mediated by DGAT1 such as the metabolic disorders disclosed herein.

It will be understood that the invention has been described by way of example only and modifications may be made whilst remaining within the scope and spirit of the invention.

We claim:

1. A compound according to formula (I) or a salt or solvate thereof:

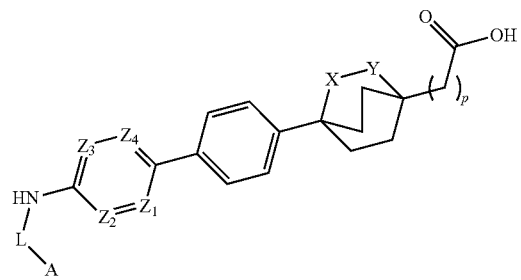

(I)

Wherein
p is 1, 2 or 3;
X is O or $CH_2$;
Y is O, $CH_2$ or absent, wherein exactly one of X and Y is O;
$Z_1$, $Z_2$, $Z_3$ and $Z_4$ are each, independently, N or CH;
L is C(O) or absent; and A is a substituted oxazole, thiazole, oxadiazole or thiadiazole substituted with at least one $C_{1-6}$alkyl, $C_{3-7}$cycloalkyl or $C_{1-6}$haloalkyl.

2. The compound according to claim 1, wherein the compound is of formula (II) or a salt or solvate thereof:

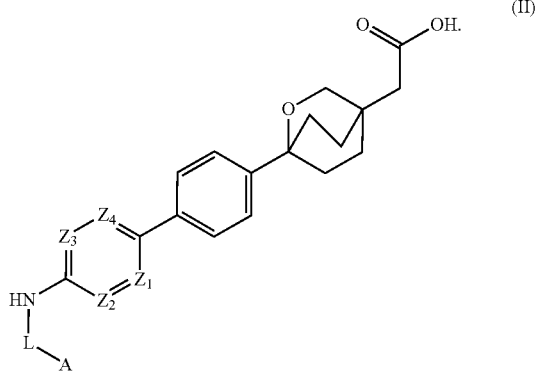

3. The compound according to claim 1, wherein the compound is of formula (III) or a salt or solvate thereof:

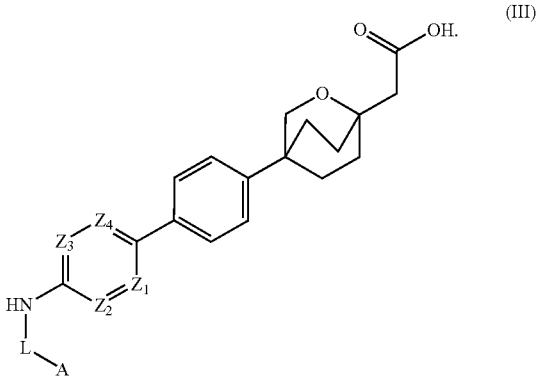

4. The compound according to claim 1, wherein the compound is of formula (IV) or a salt or solvate thereof:

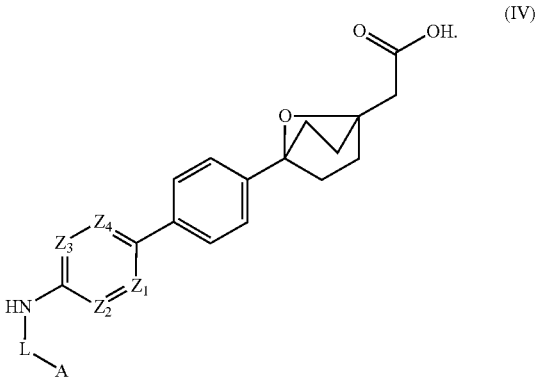

5. The compound according to claim 1, or a salt or solvate thereof, wherein p is 1.

6. The compound according to claim 1, or a salt or solvate thereof, wherein p is 2.

7. The compound according to claim 1 or a salt or solvate thereof, wherein $Z_1$, $Z_2$, $Z_3$ and $Z_4$ are all CH.

8. The compound according to claim 1, or a salt or solvate thereof, wherein $Z_1$ is N and $Z_2$, $Z_3$ and $Z_4$ are each CH.

9. The compound according to claim 1, or a salt or solvate thereof, wherein $Z_2$ is N and $Z_1$, $Z_3$ and $Z_4$ are each CH.

10. The compound according to claim 1, or a salt or solvate thereof, wherein $Z_1$ and $Z_2$ are both N and $Z_3$ and $Z_4$ are both CH.

11. The compound according to claim 1, or a salt or solvate thereof, wherein L is C(O).

12. The compound according to claim 1, or a salt or solvate thereof, wherein L is absent.

13. The compound according to claim 1, or a salt or solvate thereof, wherein A is selected from:

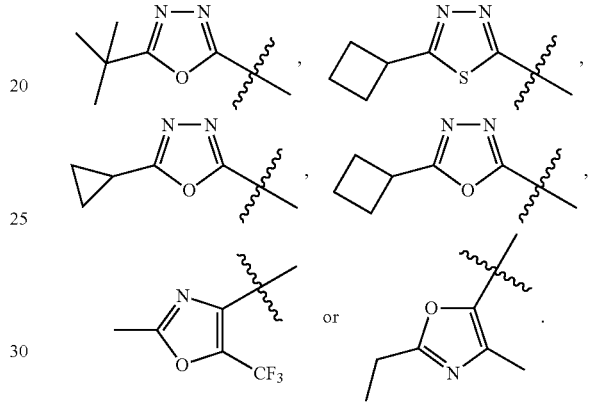

14. The compound according to claim 1, or a salt or solvate thereof, wherein A is selected from:

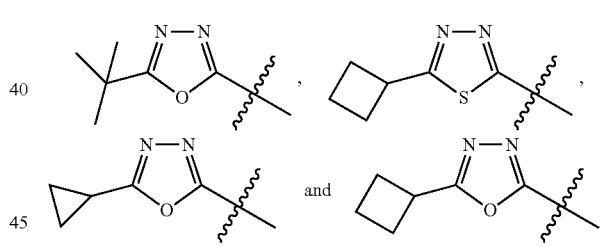

15. The compound according to claim 1, or a salt or solvate thereof, wherein A is selected from

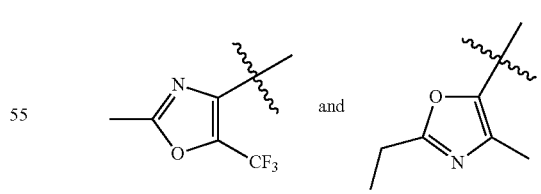

16. The compound of claim 1, or a salt or solvate thereof, which compound is selected from:

2-(4-(4'-((5-cyclobutyl-1,3,4-thiadiazol-2-yl)amino)-[1,1'-biphenyl]-4-yl)-2-oxabicyclo[2.2.2]octan-1-yl)acetic acid;

2-(4-(4'-((5-cyclobutyl-1,3,4-oxadiazol-2-yl)amino)-[1,1'-biphenyl]-4-yl)-2-oxabicyclo[2.2.2]octan-1-yl)acetic acid;

2-(4-(4-(5-(2-methyl-5-(trifluoromethyl)oxazole-4-carboxamido)pyridin-2-yl)phenyl)-2-oxabicyclo[2.2.2]octan-1-yl)acetic acid;

2-(4-(4-(5-(2-ethyl-4-methyloxazole-5-carboxamido)pyridin-2-yl)phenyl)-2-oxabicyclo[2.2.2]octan-1-yl)acetic acid;

2-(4-(4'-(2-ethyl-4-methyloxazole-5-carboxamido)-[1,1'-biphenyl]-4-yl)-2-oxabicyclo[2.2.2]octan-1-yl)acetic acid;

2-(4-(4'-((5-(tert-butyl)-1,3,4-oxadiazol-2-yl)amino)-[1,1'-biphenyl]-4-yl)-2-oxabicyclo[2.2.2]octan-1-yl)acetic acid;

2-(1-(4'-((5-cyclobutyl-1,3,4-oxadiazol-2-yl)amino)-[1,1'-biphenyl]-4-yl)-2-oxabicyclo[2.2.2]octan-4-yl)acetic acid;

2-(1-(4'-(2-methyl-5-(trifluoromethyl)oxazole-4-carboxamido)-[1,1'-biphenyl]-4-yl)-2-oxabicyclo[2.2.2]octan-4-yl)acetic acid;

2-(1-(4-(5-((5-cyclobutyl-1,3,4-oxadiazol-2-yl)amino)pyridin-2-yl)phenyl)-2-oxabicyclo[2.2.2]octan-4-yl)acetic acid;

2-(1-(4-(5-(2-methyl-5-(trifluoromethyl)oxazole-4-carboxamido)pyridin-2-yl)phenyl)-2-oxabicyclo[2.2.2]octan-4-yl)acetic acid;

2-(4-(4'-((5-cyclopropyl-1,3,4-oxadiazol-2-yl)amino)-[1,1'-biphenyl]-4-yl)-2-oxabicyclo[2.2.2]octan-1-yl)acetic acid;

3-(4-(4'-((5-(tert-butyl)-1,3,4-oxadiazol-2-yl)amino)-[1,1'-biphenyl]-4-yl)-7-oxabicyclo[2.2.1]heptan-1-yl)propanoic acid;

2-(4-(4'-((5-(tert-butyl)-1,3,4-oxadiazol-2-yl)amino)-[1,1'-biphenyl]-4-yl)-7-oxabicyclo[2.2.1]heptan-1-yl)acetic acid; or a salt or solvate thereof.

17. A pharmaceutical composition comprising one or more pharmaceutically acceptable carriers and a therapeutically effective amount of a compound of claim 1.

18. A combination, in particular a pharmaceutical combination, comprising a therapeutically effective amount of the compound according to claim 1 and a second therapeutically active agent.

* * * * *